US008785574B2

(12) United States Patent
Bando et al.

(10) Patent No.: US 8,785,574 B2
(45) Date of Patent: Jul. 22, 2014

(54) BRIDGED METALLOCENE COMPOUND, OLEFIN POLYMERIZATION CATALYST CONTAINING THE SAME, AND ETHYLENE POLYMER OBTAINED WITH THE CATALYST

(71) Applicants: Mitsui Chemicals, Inc., Tokyo (JP); Prime Polymer Co., Ltd., Tokyo (JP)

(72) Inventors: Hideki Bando, Ichihara (JP); Yasuo Satoh, Ichihara (JP); Takashi Yukita, Chiba (JP); Yasuyuki Harada, Ichihara (JP); Yoshiho Sonobe, Yokohama (JP); Yasushi Tohi, Otake (JP); Yusuke Sekioka, Otake (JP); Masao Suzuki, Ichihara (JP); Daisuke Tanifuji, Takaishi (JP)

(73) Assignees: Mitsui Chemicals, Inc., Tokyo (JP); Prime Polymer Co., Ltd., Tokyo (JP)

(*) Notice: Subject to any disclaimer, the term of this patent is extended or adjusted under 35 U.S.C. 154(b) by 0 days.

(21) Appl. No.: 14/137,531

(22) Filed: Dec. 20, 2013

(65) Prior Publication Data

US 2014/0114031 A1  Apr. 24, 2014

Related U.S. Application Data

(62) Division of application No. 12/743,544, filed as application No. PCT/JP2008/071012 on Nov. 19, 2008.

(30) Foreign Application Priority Data

Nov. 19, 2007 (JP) ................. 2007-299202
Nov. 19, 2007 (JP) ................. 2007-299203
Jan. 25, 2008 (JP) ................. 2008-015004
Jan. 25, 2008 (JP) ................. 2008-015005
Jan. 25, 2008 (JP) ................. 2008-015006

(51) Int. Cl.
C08F 4/642 (2006.01)
C08F 4/653 (2006.01)
C08F 4/6592 (2006.01)
C08F 210/02 (2006.01)
C08F 210/04 (2006.01)
C08F 210/06 (2006.01)

(52) U.S. Cl.
USPC ........... 526/113; 526/114; 526/129; 526/160; 526/165; 526/348; 526/943; 502/103; 502/113; 502/152

(58) Field of Classification Search
CPC ............ C08F 4/69504; C08F 4/65912; C08F 4/65916; C08F 4/65927; C08F 210/02; C08F 210/04; C08F 210/06
USPC ......... 526/113, 114, 129, 160, 165, 348, 943; 502/103, 113, 152
See application file for complete search history.

(56) References Cited

U.S. PATENT DOCUMENTS

| 5,017,665 | A | 5/1991 | Chang |
| 5,321,106 | A | 6/1994 | LaPointe |
| 5,374,700 | A | 12/1994 | Tsutsui et al. |
| 5,840,815 | A | 11/1998 | Tsutsui et al. |
| 5,883,205 | A | 3/1999 | Tsutsui et al. |
| 5,968,863 | A | 10/1999 | Nifant'ev et al. |
| 6,329,465 | B1 | 12/2001 | Takahashi et al. |
| 6,939,928 | B1 | 9/2005 | Kawai et al. |
| 6,960,634 | B2 | 11/2005 | Crowther et al. |
| 7,074,736 | B2 | 7/2006 | Lundquist et al. |
| 7,449,533 | B2 | 11/2008 | Kawai et al. |
| 7,629,481 | B2 | 12/2009 | Lee et al. |
| 7,858,723 | B2 | 12/2010 | Satoh et al. |
| 2008/0090983 | A1* | 4/2008 | Satoh et al. ................ 526/348.2 |

FOREIGN PATENT DOCUMENTS

| EP | 0 351 392 A2 | 1/1990 |
| EP | 0 659 773 A1 | 6/1995 |
| EP | 0 874 005 A1 | 10/1998 |
| EP | 0 955 305 A1 | 11/1999 |
| EP | 1 849 805 | * 10/2007 |
| EP | 1 849 805 A1 | 10/2007 |
| JP | 1-501950 | 7/1989 |
| JP | 1-502036 | 7/1989 |
| JP | 2-053811 | 2/1990 |
| JP | 3-179005 | 8/1991 |
| JP | 3-179006 | 8/1991 |
| JP | 3-207703 | 9/1991 |
| JP | 3-207704 | 9/1991 |
| JP | 4-069394 | 3/1992 |
| JP | 4-213306 | 8/1992 |
| JP | 4-506372 | 11/1992 |
| JP | 7-252311 | 10/1995 |
| JP | 7-278168 A | 10/1995 |
| JP | 8-502303 | 3/1996 |
| JP | 08-259582 | 10/1996 |
| JP | 9-227626 | 9/1997 |
| JP | 11-315109 | 11/1999 |
| JP | 2000-212194 | 8/2000 |
| JP | 2000-313713 A | 11/2000 |
| JP | 2002-512251 A | 4/2002 |
| JP | 2002-145923 | 5/2002 |
| JP | 2004-002310 A | 1/2004 |
| JP | 2004-168744 | 6/2004 |
| JP | 2005-200451 | 7/2005 |

(Continued)

OTHER PUBLICATIONS

Office Action for Japanese Application No. 2008-295946 dated Jul. 16, 2013.

(Continued)

Primary Examiner — Caixia Lu
(74) Attorney, Agent, or Firm — Foley & Lardner LLP

(57) ABSTRACT

According to the invention, a single or plural kinds of bridged metallocene compounds having differing cyclopentadienyl-derived groups afford macromonomers that are a source of long-chain branches and simultaneously catalyze the repolymerization of the macromonomers into olefin polymers having a large number of long-chain branches, small neck-in in the T-die extrusion, small take-up surge and superior mechanical strength. The olefin polymerization catalysts and the polymerization processes can efficiently produce the olefin polymers.

12 Claims, 6 Drawing Sheets

(56) References Cited

FOREIGN PATENT DOCUMENTS

| | | |
|---|---|---|
| JP | 2005-306989 A | 11/2005 |
| JP | 2006-002057 | 1/2006 |
| JP | 2006-233206 | 9/2006 |
| JP | 2006-233207 A | 9/2006 |
| JP | 2006-233208 | 9/2006 |
| JP | 2006-315999 A | 11/2006 |
| JP | 2007-177020 | 7/2007 |
| JP | 2008-031378 | 2/2008 |
| WO | WO-88/05792 | 8/1988 |
| WO | WO-88/05793 | 8/1988 |
| WO | WO-94/07930 | 4/1994 |
| WO | WO-99/46325 | 9/1999 |
| WO | WO-01/27124 A1 | 4/2001 |
| WO | WO-01/53362 A1 | 7/2001 |
| WO | WO-03/037938 A2 | 5/2003 |
| WO | WO-2006/033527 A1 | 3/2006 |

OTHER PUBLICATIONS

Office Action Japanese Application No. 2008-015006 dated Jun. 4, 2013.
Communication (Supplementary EP Search Report) in EP Appln No: 08851276.9 dated Aug. 5, 2011.
Kagaku no Ryouiki Zoukan (Region of chemistry, extra edition) No. 141, NMR—Sousetsu to Jikken Gaido (Review and Experimental Guide) [I], Oct. 1983, pp. 132-133.
J. W. Strauch et al., "(Butadiene)metallocene/B($C_6F_5$)$_3$ Pathway to Catalyst Systems for Stereoselective Methyl Methacrylate Polymerization: Evidence for an Anion Dependent Metallocene Catalyzed Polymerization Process," J. Am. Chem. Soc., vol. 126, No. 7, (2004), pp. 2089-2104.
N. Suzuki et al., "Structural characterization of ansa-zirconocene dichloride bearing a vicinal di-*tert*-butylcyclopentadienyl ligand and high pressure polymerization of 1-hexane catalyzed by sterically hindered zirconocene complexes," Journal of Organometallic Chemistry, vol. 560, No. 1-2, (1998), pp. 47-54.
International Search Report mailed Dec. 19, 2008 received in PCT/JP2008/071012.
"Polyethylene Gijutsu Dokuhon (Polyethylene Technology Reader)", edited by Kazuo Matsuura and Naotaka Mikami, Kogyo Chosakai Publishing, Inc., 2001, pp. 44 - 47.
Burchard, W.—Advances in Polymer Science, 1999, 143, Branched Polymers II, pp. 136-137.
Gabriel, et al. "Strain hardening of various polyolefins in uniaxial elongational flow" Journal of Rheology, May/Jun. 2003, vol. 47, Issue 3, pp. 619-630.
Grubisic, et al. "A Universal Calibration for Gel Permeation Chromatography" Polymer Letters, Sep. 1967, Part B, vol. 5, No. 9, pp. 753-759.
Heiland, et al., Macromolecular Chemistry and Physics, Mar. 1992, vol. 193, No. 3, pgs. 606-607.
Keii, et al. "Catalytic Olefin Polymerization", Studies in Surface Science and Catalysis, 1990, vol. 56, pp. 376- 377.
Koubunshi no Jumyou Yosoku to Choujumyouka Gijutsu (Lifetime Prediction of Polymers and Lifetime Extending Technology), edited by Zenjiro Osawa, et al., NTS, 2002, p. 480-481.

\* cited by examiner

BRIDGED METALLOCENE COMPOUND, OLEFIN POLYMERIZATION CATALYST CONTAINING THE SAME, AND ETHYLENE POLYMER OBTAINED WITH THE CATALYST

CROSS-REFERENCE TO RELATED APPLICATIONS

This application is a divisional of U.S. patent application Ser. No. 12/743,544, filed May 18, 2010, which is the National Phase of PCT/JP2008/071012, filed Nov. 19, 2008, which claims priority from Japanese Patent Application Nos. 2007-299202, filed Nov. 19, 2007, 2007-299203, filed Nov. 19, 2007, 2008-015004, filed Jan. 25, 2008, 2008-015005, filed Jan. 25, 2008, and 2008-015006, filed Jan. 25, 2008. The contents of these applications are hereby incorporated by reference in their entirety.

FIELD OF THE INVENTION

The present invention relates to metallocene compounds useful as olefin polymerization catalysts or catalyst components, and to olefin polymerization processes with an olefin polymerization catalyst containing the metallocene compound. In detail, the invention relates to olefin polymerization catalysts that can catalyze with high polymerization activity the production of olefin polymers having high melt tension, excellent mechanical strength and good particle properties, and relates to olefin polymerization processes using the catalysts. Further, the invention relates to ethylene polymers obtained by the polymerization processes that have good processability and particularly excellent mechanical strength compared to conventional ethylene polymers, and relates to thermoplastic resin compositions containing the ethylene polymers. In more detail, the invention is concerned with shaped articles ical strength compaor films that are obtained from the ethylene polymers or the thermoplastic resin compositions containing the ethylene polymers, or relates to laminate films including the films. Furthermore, the invention is concerned with ethylene polymers that have good processability and easy-opening properties compared to conventional ethylene polymers, and thermoplastic resin compositions containing the ethylene polymers. In more detail, the invention is concerned with shaped articles or films that are obtained from the ethylene polymers or the thermoplastic resin compositions containing the ethylene polymers, or relates to laminate films including the films.

BACKGROUND OF THE INVENTION

Olefin polymers are shaped by various methods and used in wide-ranged applications. For example, ethylene polymers are extruded into films or sheets for use in the packaging of foods, liquids or daily sundries. Olefin polymers require various properties depending on the shaping methods or use applications. In the case of T-die extrusion as an example, they require performances such as stable processability even at high speed (high-speed film-forming properties) and small neck-in.

Low density polyethylenes (LDPE) by high-pressure radical polymerization have a high melt tension because of their complicated long-chain branched structures, and show good shaping processability such as small neck-in, thereby finding various uses. However, shaped articles therefrom still have low mechanical strength properties such as tensile strength, tear strength and impact resistant strength. Further, these polymers show poor high-speed film-forming properties in T-die extrusion.

In contrast to LDPE, Ziegler-catalyzed or metallocene-catalyzed ethylene polymers possess high tensile strength, tear strength and impact resistant strength due to their molecular structures, and they are used in applications requiring mechanical strength. However, these polymers have a low melt tension and consequent poor shaping processability.

To solve these problems, [1] LDPE is blended with a Ziegler-catalyzed or metallocene-catalyzed ethylene polymer (Patent Document 1); [2] the molecular weight distribution is broadened by multistage polymerization (Patent Document 2); [3] a long-chain branched ethylene polymer is produced with a chromium catalyst; [4] a long-chain branched ethylene polymer is produced with a specific metallocene catalyst (Patent Document 3); [5] macro monomers are copolymerized with use of a specific metallocene catalyst to give a long-chain branched ethylene polymer (Patent Document 4); or [6] ethylene and diene are copolymerized with use of a specific metallocene catalyst to afford a long-chain branched ethylene polymer (Patent Documents 6 and 7). However, the method [1] greatly increases costs in the blending of the polymers, and the ethylene polymers obtained by the methods [2], [3], [4] and [5] have a small number of long-chain branches and do not have a sufficient melt tension or shaping processability. Further, the method [6] can deteriorate mechanical characteristics inherent to polymers or can result in gelation when the diene is used in large amounts.

Patent Documents 8 and 9 teach the use of two or more kinds of metallocene compounds or organometallic complexes in order to produce more long-chain branches or to increase the melt tension. However, the number of long-chain branches is still insufficient and problems remain in terms of shaping processability. Further, the catalytic activity is far below the industrial level.

As discussed above, it has been difficult to produce resins having high melt tension and excellent mechanical strength inexpensively and efficiently by means of the conventional catalyst systems or by blending resins. In other words, the development of efficient production processes for ethylene polymers having high melt tension and excellent mechanical strength is important and highly valuable in the industrial production.

When ethylene polymers are used as sealants in packaging materials, the polymers require mechanical strength such as heat seal strength or pack breakage strength to protect the contents. However, packaging materials that are easily opened (have easy openability) attract attention out of consideration for elderly people, infants and disabled people. One of the approaches for easy openability is to appropriately weaken the heat seal strength at the sealed portion. Accordingly, there is a need for ethylene polymers having appropriately low heat seal strength.

The present inventors studied diligently in view of the problems in the art as describe above. They have then found that a single or plural kinds of bridged metallocene compounds having differing cyclopentadienyl-derived groups can afford macromonomers that are a source of long-chain branches and can simultaneously catalyze the repolymerization of the macromonomers into olefin polymers having a large number of long-chain branches, small neck-in in the T-die extrusion, small take-up surge and superior mechanical strength or olefin polymers having small neck-in in the T-die extrusion, small take-up surge and easy opening properties. Such compounds as olefin polymerization catalysts and polymerization processes using the compounds have been found to be capable of efficiently producing the olefin polymers as described above. The present invention has been completed based on the findings.

Patent Document 1: WO 99/046325
Patent Document 2: JP-A-H02-53811
Patent Document 3: JP-A-H04-213306
Patent Document 4: JP-A-H08-502303
Patent Document 5: JP-A-H04-213306
Patent Document 6: JP-A-H09-227626
Patent Document 7: JP-A-H04-506372
Patent Document 8: JP-A-H07-252311
Patent Document 9: JP-A-2006-2057

SUMMARY OF THE INVENTION

The present invention has been made in view of the background art as discussed above. It is therefore an object of the invention to provide bridged metallocene compounds for olefin polymerization that can afford with high polymerization activity a relatively low molecular weight olefin polymer (macromonomer) having a higher proportion of terminal double bonds than produced by conventional metallocene compounds. It is another object to provide olefin polymerization catalysts containing the bridged metallocene compounds, in detail olefin polymerization catalysts that can catalyze with high polymerization activity the production of olefin polymers having high melt tension, excellent mechanical strength and good particle properties, and to provide polymerization processes using the catalysts. It is a further object of the invention to provide ethylene homopolymers or copolymers that have good processability and particularly excellent mechanical strength compared to conventional ethylene polymers, and to provide thermoplastic resin compositions containing the polymers. It is a still further object to provide shaped articles or films that are obtained from the polymers or the thermoplastic resin compositions, or to provide laminate films including the films. Furthermore, the invention has an object of providing ethylene homopolymers or copolymers that have good processability and easy-opening properties compared to conventional ethylene polymers, and thermoplastic resin compositions containing the ethylene polymers. It is a still further object of the invention to provide shaped articles or films that are obtained from the polymers or the thermoplastic resin compositions, or to provide laminate films including the films.

A bridged metallocene compound according to the present invention is represented by Formula [1] below:

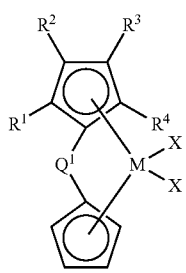

[1]

wherein $R^1$, $R^2$, $R^3$ and $R^4$ are selected from a hydrogen atom, hydrocarbon groups, silicon-containing groups, heteroatom-containing groups and halogen-containing groups and are the same or different from one another; $R^1$, $R^2$, $R^3$ and $R^4$ are not all hydrogen atoms and at least one of these groups is an ethyl group or a group represented by any of Formulae [2] to [7] below; neighboring substituent groups among $R^1$ to $R^4$ may be linked together to form an aliphatic ring; $Q^1$ is selected from C1-20 hydrocarbon groups, halogen-containing groups, silicon-containing groups, germanium-containing groups and tin-containing groups; X independently at each occurrence is a group selected from a hydrogen atom, halogen atoms, hydrocarbon groups, halogen-containing groups, silicon-containing groups, oxygen-containing groups, sulfur-containing groups, nitrogen-containing groups and phosphorus-containing groups; and M is a titanium atom, a zirconium atom or a hafnium atom;

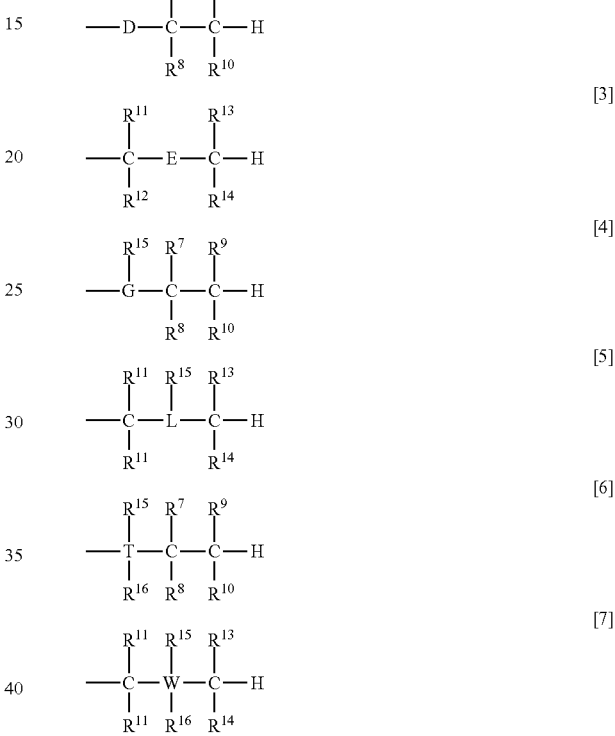

wherein $R^7$ to $R^{16}$ are selected from a hydrogen atom, hydrocarbon groups, silicon-containing groups, heteroatom-containing groups and halogen-containing groups and are the same or different from one another, but they are not aryl groups; D and E are each a divalent heteroatom; G and L are each a trivalent heteroatom; and T and W are each a tetravalent heteroatom or a carbon atom.

An olefin polymerization catalyst (a) according to the present invention comprises the following components (A) and (C):

Component (A): the bridged metallocene compound represented by Formula (1) above;

Component (C): at least one compound selected from the group consisting of:

(c-1) organometallic compounds represented by Formulae [11], [12] and [13] below;
(c-2) organoaluminum oxy-compounds; and
(c-3) compounds that react with the component (A) to form an ion pair;

$$R^a{}_m Al(OR^b)_n H_p X_q \quad [11]$$

wherein $R^a$ and $R^b$ are each a C1-15 hydrocarbon group and are the same or different from each other; X is a halogen atom; 0<m≤3, 0≤n<3, 0≤p<3, 0≤q<3 and m+n+p+q=3;

$$M^a AlR^a{}_4 \quad [12]$$

wherein $M^a$ is Li, Na or K; and $R^a$ is a C1-15 hydrocarbon group;

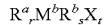  [13]

wherein $R^a$ and $R^b$ are each a C1-15 hydrocarbon group and are the same or different from each other; $M^b$ is selected from Mg, Zn and Cd; X is a halogen atom; $0<r\leq2$, $0\leq s\leq1$, $0\leq t\leq1$ and $r+s+t=2$.

An olefin polymerization catalyst (b) according to the present invention comprises the following components (A), (B) and (C):

Component (A): the bridged metallocene compound represented by Formula [1] above;

Component (B): a bridged metallocene compound represented by Formula [14] below;

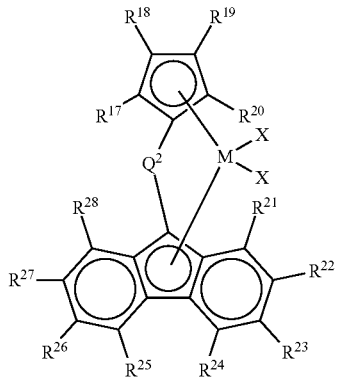  [14]

wherein $R^{17}$ to $R^{20}$, and $R^{21}$ to $R^{28}$ are selected from a hydrogen atom, hydrocarbon groups, halogen-containing groups, oxygen-containing groups, nitrogen-containing groups, boron-containing groups, sulfur-containing groups, phosphorus-containing groups, silicon-containing groups, germanium-containing groups and tin-containing groups and are the same or different from one another; neighboring substituent groups among these groups may be linked together to form a ring; $Q^2$ is selected from C1-20 hydrocarbon groups, halogen-containing groups, silicon-containing groups, germanium-containing groups and tin-containing groups; M is selected from a titanium atom, a zirconium atom and a hafnium atom; and X independently at each occurrence is a group selected from a hydrogen atom, halogen atoms, hydrocarbon groups, halogen-containing groups, silicon-containing groups, oxygen-containing groups, sulfur-containing groups, nitrogen-containing groups and phosphorus-containing groups;

Component (C): at least one compound selected from the group consisting of:

(c-1) organometallic compounds represented by Formulae [18], [19] and [20] below;

(c-2) organoaluminum oxy-compounds; and (c-4) compounds that react with the components (A) and (B) to form an ion pair;

$R^a_m Al(OR^b)_n H_p X_q$  [18]

wherein $R^a$ and $R^b$ are each a C1-15 hydrocarbon group and are the same or different from each other; X is a halogen atom; $0<m\leq3$, $0\leq n<3$, $0\leq p<3$, $0\leq q<3$ and $m+n+p+q=3$;

$M^a AlR^a_4$  [19]

wherein $M^a$ is Li, Na or K; and $R^a$ is a C1-15 hydrocarbon group;

  [20]

wherein $R^a$ and $R^b$ are each a C1-15 hydrocarbon group and are the same or different from each other; $M^b$ is selected from Mg, Zn and Cd; X is a halogen atom; $0<r\leq2$, $0\leq s\leq1$, $0\leq t\leq1$ and $r+s+t=2$.

The olefin polymerization catalyst (b) may further contain a solid carrier (S). In an embodiment, such olefin polymerization catalyst may comprise a solid catalyst component (K1) comprising the solid carrier (S), the component (C) and the component (A), and a solid catalyst component (K2) comprising the solid carrier (S), the component (C) and the component (B). In another embodiment, such olefin polymerization catalyst may comprise a solid catalyst component (K3) comprising the solid carrier (S), the component (A), the component (B) and the component (C).

In Formula (1), at least one of $R^1$, $R^2$, $R^3$ and $R^4$ is preferably a hydrocarbon group. The component (C) is preferably an organoaluminum oxy-compound. The solid carrier (S) is preferably a porous oxide.

A process for producing ethylene polymers according to the present invention comprises homopolymerizing ethylene or polymerizing ethylene and a C3-20 olefin in the presence of any of the olefin polymerization catalysts described above.

An ethylene polymer (i) according to the present invention is obtained by homopolymerizing ethylene or copolymerizing ethylene and a C4-10 α-olefin in the presence of the olefin polymerization catalyst (b) and satisfies the following requirements [1] to [5] at the same time:

[1] the melt flow rate (MFR) as measured at 190° C. under a load of 2.16 kg is in the range of 0.1 to 100 g/10 min;

[2] the density (d) is in the range of 875 to 970 kg/m$^3$;

[3] the ratio [MT/η*(g/P)] is in the range of $1.50\times10^{-4}$ to $9.00\times10^{-4}$ wherein [MT (g)] is the melt tension at 190° C. and [η*(P)] is the shear viscosity at 200° C. and an angular velocity of 1.0 rad/sec;

[4] per 1000 carbon atoms, the total of methyl branches [A(/1000 C)] and ethyl branches [B(/1000 C)], [(A+B)(/1000 C)], is not more than 1.8 according to $^{13}$C-NMR;

[5] the zero-shear viscosity at 200° C. [η$_0$ (P)] and the weight average molecular weight (Mw) measured by GPC-viscometry (GPC-VISCO) satisfy Equation (Eq-1) below:

$$0.01\times10^{-13}\times Mw^{3.4} \leq \eta_0 \leq 4.5\times10^{-13}\times Mw^{3.4} \qquad \text{(Eq-1)}$$

An ethylene polymer (ii) according to the present invention is obtained by homopolymerizing ethylene or copolymerizing ethylene and a C4-10 α-olefin in the presence of the olefin polymerization catalyst (b) and satisfies the following requirements [1] to [6] at the same time:

[1] the melt flow rate (MFR) as measured at 190° C. under a load of 2.16 kg is in the range of 0.1 to 100 g/10 min;

[2] the density (d) is in the range of 875 to 970 kg/m$^3$;

[3] the ratio [MT/η*(g/P)] is in the range of $2.50\times10^{-4}$ to $9.00\times10^{-4}$ wherein [MT (g)] is the melt tension at 190° C. and [η*(P)] is the shear viscosity at 200° C. and an angular velocity of 1.0 rad/sec;

[4] per 1000 carbon atoms, the total of methyl branches [A(/1000 C)] and ethyl branches [B(/1000 C)], [(A+B)(/1000 C)], is not more than 1.8 according to $^{13}$C-NMR;

[5] the zero-shear viscosity at 200° C. [η$_0$ (P)] and the weight average molecular weight (Mw) measured by GPC-viscometry (GPC-VISCO) satisfy Equation (Eq-1) below:

$$0.01\times10^{-13}\times Mw^{3.4} \leq \eta_0 \leq 4.50\times10^{-13}\times Mw^{3.4} \qquad \text{(Eq-1)}$$

[6] a molecular weight distribution curve obtained by GPC shows a molecular weight at a maximum weight fraction (peak top M) in the range of $1.0\times10^{4.30}$ to $1.0\times10^{4.50}$.

An ethylene polymer (iii) according to the present invention is obtained by homopolymerizing ethylene or copolymerizing ethylene and a C4-10 α-olefin in the presence of the olefin polymerization catalyst (b) and satisfies the following requirements [1] to [6] at the same time:

[1] the melt flow rate (MFR) as measured at 190° C. under a load of 2.16 kg is in the range of 0.1 to 100 g/10 min;

[2] the density (d) is in the range of 875 to 936 kg/m³;

[3] the ratio [MT/η*(g/P)] is in the range of $2.50 \times 10^{-4}$ to $9.00 \times 10^{-4}$ wherein [MT (g)] is the melt tension at 190° C. and [η*(P)] is the shear viscosity at 200° C. and an angular velocity of 1.0 rad/sec;

[4] per 1000 carbon atoms, the total of methyl branches [A(/1000 C)] and ethyl branches [B(/1000 C)], [(A+B)(/1000 C)], is not more than 1.8 according to $^{13}$C-NMR;

[5] the zero-shear viscosity at 200° C. [η₀ (P)] and the weight average molecular weight (Mw) measured by GPC-viscometry (GPC-VISCO) satisfy Equation (Eq-1) below:

$$0.01 \times 10^{-13} \times Mw^{3.4} \leq \eta_0 \leq 4.50 \times 10^{-13} \times Mw^{3.4} \quad \text{(Eq-1)}$$

[6] a molecular weight distribution curve obtained by GPC shows a molecular weight at a maximum weight fraction (peak top M) in the range of $1.0 \times 10^{4.20}$ to $1.0 \times 10^{4.50}$.

An ethylene polymer (iv) according to the present invention is obtained by homopolymerizing ethylene or copolymerizing ethylene and a C3-10 α-olefin in the presence of the olefin polymerization catalyst (b) and satisfies the following requirements [1] to [5] at the same time:

[1] the ratio [$M_{3-4}/M_{3-10}$] is in the range of 0.30 to 1.00 wherein [$M_{3-4}$ (mol %)] is the content of C3-4 α-olefins and [$M_{3-10}$ (mol %)] is the content of C3-10 α-olefins according to $^{13}$C-NMR;

[2] the melt flow rate (MFR) as measured at 190° C. under a load of 2.16 kg is in the range of 0.1 to 100 g/10 min;

[3] the density (d) is in the range of 875 to 970 kg/m³;

[4] the ratio [MT/η*(g/P)] is in the range of $1.50 \times 10^{-4}$ to $9.00 \times 10^{-4}$ wherein [MT (g)] is the melt tension at 190° C. and [η*(P)] is the shear viscosity at 200° C. and an angular velocity of 1.0 rad/sec;

[5] the zero-shear viscosity at 200° C. [η₀ (P)] and the weight average molecular weight (Mw) measured by GPC-viscometry (GPC-VISCO) satisfy Equation (Eq-1) below:

$$0.01 \times 10^{-13} \times Mw^{3.4} \leq \eta_0 \leq 4.5 \times 10^{-13} \times Mw^{3.4} \quad \text{(Eq-1)}$$

The ethylene polymers (i to iii) may be blended with other thermoplastic resins to give thermoplastic resin compositions having excellent processability and superior mechanical strength. The ethylene polymers (i to iii) and the resin compositions containing the ethylene polymers (i to iii) may be processed with good processability into shaped articles having excellent mechanical strength, which are preferably films, and more preferably laminate films containing the films.

The ethylene polymers (iv) may be blended with other thermoplastic resins to give thermoplastic resin compositions having excellent processability and easy opening properties. The ethylene polymers (iv) and the resin compositions containing the ethylene polymers (iv) may be processed with good processability into shaped articles having easy opening properties, which are preferably films, and more preferably laminate films containing the films.

ADVANTAGEOUS EFFECTS OF THE INVENTION

The olefin polymerization catalysts (a) containing the bridged metallocene compound of the invention can catalyze olefin homopolymerization or copolymerization to provide low molecular weight olefin homopolymers or copolymers having an increased number of terminal double bonds.

According to the present invention, macromonomers can be produced efficiently by polymerizing one or more monomers selected from ethylene and α-olefins wherein at least one of the monomers is ethylene or propylene, in the presence of the olefin polymerization catalyst (a) containing the bridged metallocene compound.

The olefin polymerization catalysts (b) containing the bridged metallocene compound of the invention can catalyze olefin homopolymerization or copolymerization to provide ethylene polymers having excellent shaping processability and a large number of long-chain branches. The processes of the invention can efficiently produce such polymers.

The ethylene polymers (i to iii) and the thermoplastic resin compositions containing the polymers can favorably give shaped articles, films or laminate films containing the films which have small neck-in in the T-die extrusion, small take-up surge and superior mechanical strength. The ethylene polymers (iv) and the thermoplastic resin compositions containing the polymers show excellent processability and can favorably give shaped articles, films or laminate films containing the films which have easy opening properties.

PREFERRED EMBODIMENTS FOR CARRYING OUT THE INVENTION

Figure 1:
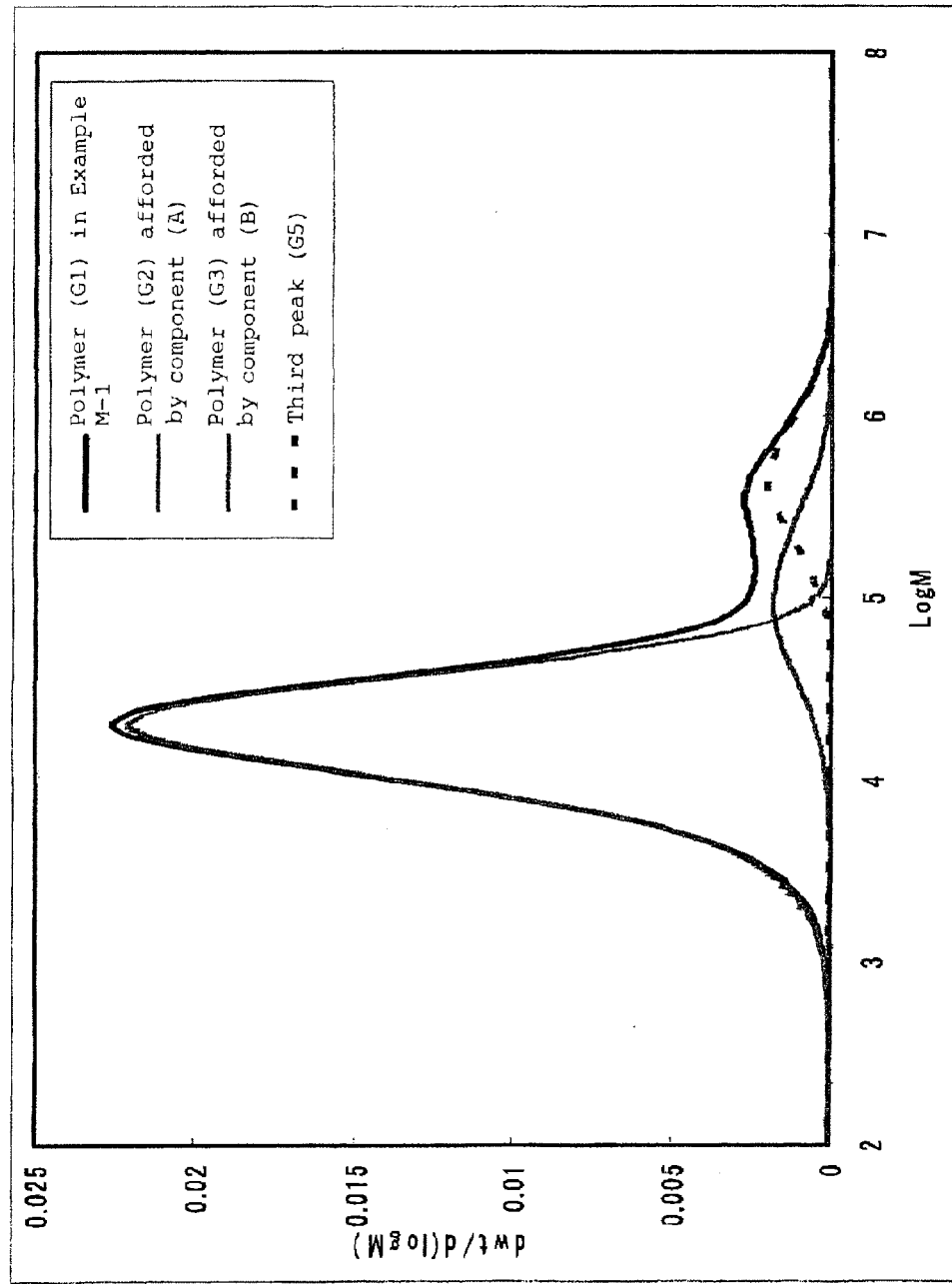
FIG. 1 is a GPC chart of a polymer obtained in Example M-1.

There will be described in detail hereinbelow the bridged metallocene compounds of Formula [1], the olefin polymerization catalysts (a) containing the bridged metallocene compounds, the olefin polymerization catalysts (b) containing the bridged metallocene compounds of Formula [1] and the bridged metallocene compounds of Formula [14], the olefin polymerization processes using the olefin polymerization catalysts (a) or (b), and the ethylene polymers (i to iv) obtained by homopolymerizing or copolymerizing ethylene in the presence of the olefin polymerization catalysts (b).

In the invention, the term polymerization comprehends not only homopolymerization but copolymerization, and the term polymer comprehends not only homopolymer but copolymer.

Bridged Metallocene Compounds

Bridged metallocene compounds of the invention are represented by Formula [1] below:

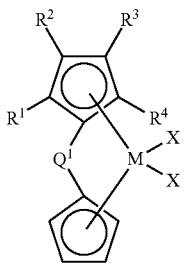

[1]

In Formula [1], M is a Group IV transition metal atom in the periodic table, specifically titanium, zirconium or hafnium, and preferably zirconium.

In Formula [1], $R^1$, $R^2$, $R^3$ and $R^4$ are selected from a hydrogen atom, hydrocarbon groups, silicon-containing groups, heteroatom-containing groups and halogen-containing groups and are the same or different from one another; $R^1$, $R^2$, $R^3$ and $R^4$ are not all hydrogen atoms and at least one of these groups is an ethyl group or a group represented by any of Formulae [2] to [7] below; and neighboring substituent groups among $R^1$ to $R^4$ may be linked together to form an aliphatic ring.

Examples of the hydrocarbon groups include C1-20 alkyl groups, C3-20 cycloalkyl groups and C7-20 aralkyl groups (for example, benzyl group). Specific examples include methyl group, ethyl group, n-propyl group, isopropyl group, allyl group, n-butyl group, t-butyl group, amyl group, n-pentyl group, n-hexyl group, n-heptyl group, n-octyl group, n-nonyl group, n-decanyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group, 1-methyl-1-isopropyl-2-methylpropyl group, cyclopentyl group, cyclohexyl group, cycloheptyl group, cyclooctyl group, norbornyl group, adamantyl group and benzyl group.

Examples of the silicon-containing groups include hydrocarbon-substituted silyl groups such as trimethylsilyl group, triethylsilyl group, diphenylmethylsilyl group and dimethylphenylsilyl group.

Examples of the heteroatom-containing groups include alkoxy groups, aryloxy groups and amino groups such as methoxy group, ethoxy group, phenoxy group, N-methylamino group, N,N-dimethylamino group and N-phenylamino group.

Examples of the halogen-containing groups include halogen atoms and halogen-substituted alkyl groups such as fluoro group, chloro group, bromo group, iodo group, trifluoromethyl group, trifluoroethyl group, trifluoropropyl group, trifluorobutyl group and trichlorobutyl group.

Neighboring substituent groups among $R^1$ to $R^4$ may be linked together to form an aliphatic ring. Such substituted cyclopentadienyl groups include tetrahydroindenyl, 2-methyltetrahydroindenyl, 2,2,4-trimethyltetrahydroindenyl, 4-phenyltetrahydroindenyl, 2-methyl-4-phenyltetrahydroindenyl, and a substituted cyclopentadienyl group in which $R^3$ and $R^4$ are tetramethylene groups linking together to form a ring and $R^1$ and $R^2$ are tetramethylene groups linking together to form a ring.

In Formulae [2] to [7] below, $R^7$ to $R^{16}$ are selected from a hydrogen atom, hydrocarbon groups, silicon-containing groups, heteroatom-containing groups and halogen-containing groups and are the same or different from one another, but they are not aryl groups. Examples of the hydrocarbon groups, the silicon-containing groups, the heteroatom-containing groups and the halogen-containing groups are as described above.

D and E are selected from divalent heteroatoms. Exemplary divalent heteroatoms are an oxygen atom and a sulfur atom. G and L are selected from trivalent heteroatoms. Exemplary trivalent heteroatoms are a nitrogen atom and a phosphorus atom. T and W are selected from tetravalent heteroatoms and a carbon atom. An exemplary tetravalent heteroatom is a silicon atom.

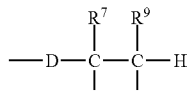

[2]

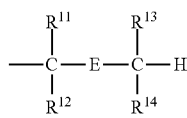

[3]

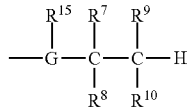

[4]

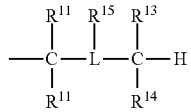

[5]

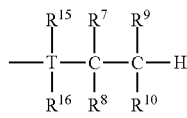

[6]

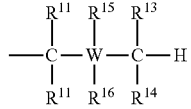

[7]

Examples of the groups represented by Formula [2] include ethoxy group, n-propoxy group, n-butoxy group, isobutoxy group, t-butoxy group, n-pentyloxy group, 2-neopentyloxy group, n-hexyloxy group, n-heptyloxy group, n-octyloxy group, n-nonyloxy group, n-decanyloxy group, 3,3,3-trifluoropropoxy group, 4-phenylbutoxy group, ethylsulfanyl group, n-propylsulfanyl group, n-butylsulfanyl group, isobutylsulfanyl group, t-butylsulfanyl group, n-pentylsulfanyl group, 2-neopentylsulfanyl group, n-hexylsulfanyl group, n-heptylsulfanyl group, n-octylsulfanyl group, n-nonylsulfanyl group, n-decanylsulfanyl group, 3,3,3-trifluoropropylsulfanyl group and 4-phenylbutylsulfanyl group.

Examples of the groups represented by Formula [3] include methoxymethyl group, ethoxymethyl group, n-propoxymethyl group, n-butoxymethyl group, isobutoxymethyl group, t-butoxymethyl group, n-pentyloxymethyl group, 2-neopentyloxymethyl group, n-hexyloxymethyl group, n-heptyloxymethyl group, n-octyloxymethyl group, n-nonyloxymethyl group, n-decanyloxymethyl group, 3,3,3-trifluoropropoxymethyl group, 4-phenylbutoxymethyl group, methylsulfanylmethyl group, ethylsulfanylmethyl group, n-butylsulfanylmethyl group, isobutylsulfanylmethyl group, t-butylsulfanylmethyl group, n-pentylsulfanylmethyl group, 2-neopentylsulfanylmethyl group, n-hexylsulfanylmethyl group, n-heptylsulfanylmethyl group, n-octylsulfanylmethyl group, n-nonylsulfanylmethyl group, n-decanylsulfanylmethyl group, 3,3,3-trifluoropropylsulfanylmethyl group and 4-phenylbutylsulfanylmethyl group.

Examples of the groups represented by Formula [4] include N-ethyl-N-methylamino group, N-(n-propyl)-N-methylamino group, (ethyl)(methyl)phosphinomethyl group, N-(n-butyl)-N-methylamino group, N-(isobutyl)-N-methylamino group, N-(t-butyl)-N-methylamino group, N-(n-pentyl)-N-methylamino group, N-(2-neopentyl)-N-methylamino group, N-(n-hexyl)-N-methylamino group, N-(n-heptyl)-N-methylamino group, N-(n-octyl)-N-methylamino group, N-(n-nonyl)-N-methylamino group, N-(n-decanyl)-N-methylamino group, N-(3,3,3-trifluoropropyl)-N-methylamino group, N-(4-phenylbutyl)-N-methylamino group, (ethyl)(methyl)phosphino group, diethylphosphino group, (n-propyl)(methyl)phosphino group, (n-butyl)(methyl)phosphino group, (n-propyl)(methyl)phosphino group, (n-butyl)(methyl)phosphino group, (isobutyl)(methyl)phosphino group, (t-butyl)(methyl)phosphino group, (n-pentyl)(methyl)phosphino group, (2-neopentyl)(methyl)phosphino group, (n-hexyl)(methyl)phosphino group, (n-heptyl)(methyl) phosphino group, (n-octyl)(methyl) phosphino group, (n-nonyl)(methyl) phosphino group, (n-decanyl)(methyl) phosphino group, (3,3,3-trifluoropropyl)(methyl) phosphino group and (4-phenylbutyl)(methyl) phosphino group.

Examples of the groups represented by Formula [5] include N,N-dimethylaminomethyl group, N-ethyl-N-methylaminomethyl group, N-(n-propyl)-N-methylaminomethyl group, (ethyl)(methyl) phosphinomethyl group, N-(n-butyl)-N-methylaminomethyl group, N-(isobutyl)-N-methylaminomethyl group, N-(t-butyl)-N-methylaminomethyl group, N-(n-pentyl)-N-methylaminomethyl group, N-(2-neopentyl)-N-methylaminomethyl group, N-(n-hexyl)-N-methylaminomethyl group, N-(n-heptyl)-N-methylaminomethyl group, N-(n-octyl)-N-methylaminomethyl group, N-(n-nonyl)-N-methylaminomethyl group, N-(n-decanyl)-N-methylaminomethyl group, N-(3,3,3-trifluoropropyl)-N-methylaminomethyl group, N-(4-phenylbutyl)-N-methylaminomethyl group, (ethyl)(methyl)phosphinomethyl group, diethylphosphinomethyl group, (n-propyl)(methyl) phosphinomethyl group, (n-butyl)(methyl)phosphinomethyl group, (n-propyl)(methyl)phosphinomethyl group, (n-butyl)(methyl)phosphinomethyl group, (isobutyl)(methyl)phosphinomethyl group, (t-butyl)(methyl)phosphinomethyl group, (n-pentyl)(methyl)phosphinomethyl group, (2-neopentyl)(methyl)phosphinomethyl group, (n-hexyl)(methyl)phosphinomethyl group, (n-heptyl)(methyl)phosphinomethyl group, (n-octyl)(methyl)phosphinomethyl group, (n-nonyl)(methyl)phosphinomethyl group, (n-decanyl)(methyl)phosphinomethyl group, (3,3,3-trifluoropropyl)(methyl)phosphinomethyl group and (4-phenylbutyl)(methyl)phosphinomethyl group.

Examples of the groups represented by Formula [6] include n-propyl group, n-butyl group, isobutyl group, t-butyl group, n-pentyl group, 2-neopentyl group, n-hexyl group, n-heptyl group, n-octyl group, n-nonyl group, n-decanyl group, 4,4,4-trifluorobutyl group, 4-phenylbutyl group, ethyldimethylsilyl group, n-propyldimethylsilyl group, n-butyldimethylsilyl group, isobutyldimethylsilyl group, t-butyldimethylsilyl group, n-pentyldimethylsilyl group, 2-neopentyldimethylsilyl group, n-hexyldimethylsilyl group, n-heptyldimethylsilyl group, n-octyldimethylsilyl group, n-nonyldimethylsilyl group, n-decanyldimethylsilyl group, 3,3,3-trifluoropropyldimethylsilyl group and 4-phenylbutyldimethylsilyl group.

Examples of the groups represented by Formula [7] include n-propyl group, n-butyl group, isobutyl group, t-butyl group, n-pentyl group, 2-neopentyl group, n-hexyl group, n-heptyl group, n-octyl group, n-nonyl group, n-decanyl group, 4,4,4-trifluorobutyl group, 4-phenylbutyl group, ethyldimethylsilylmethyl group, n-propyldimethylsilylethyl group, n-butyldimethylsilylethyl group, isobutyldimethylsilylethyl group, t-butyldimethylsilylethyl group, n-pentyldimethylsilylethyl group, 2-neopentyldimethylsilylethyl group, n-hexyldimethylsilylethyl group, n-heptyldimethylsilylethyl group, n-octyldimethylsilylethyl group, n-nonyldimethylsilylethyl group, n-decanyldimethylsilylethyl group, 3,3,3-trifluoropropyldimethylsilylethyl group and 4-phenylbutyldimethylsilylethyl group.

In a preferred embodiment, $R^1$ to $R^4$ are selected from a hydrogen atom, hydrocarbon groups and halogen-containing groups, and at least one of $R^1$ to $R^4$ is a hydrocarbon group. In a more preferred embodiment, $R^1$ to $R^4$ are each a hydrogen atom or a C1-15 hydrocarbon group. In a still more preferred embodiment, three substituent groups of $R^1$ to $R^4$ are hydrogen atoms and the other is a C1-15 hydrocarbon group. In a particularly preferred embodiment, three substituent groups of $R^1$ to $R^4$ are hydrogen atoms and the other is a C3-15 hydrocarbon group.

In Formula (1), $Q^1$ is a divalent group linking the two ligands and is selected from C1-20 hydrocarbon groups such as alkylene groups, substituted alkylene groups and alkylidene groups; halogen-containing groups; silicon-containing groups; germanium-containing groups; and tin-containing groups.

Examples of the alkylene groups, substituted alkylene groups and alkylidene groups each having 1 to 20 carbon atoms include alkylene groups such as methylene, ethylene, propylene and butylene; substituted alkylene groups such as isopropylidene, diethylmethylene, dipropylmethylene, diisopropylmethylene, dibutylmethylene, methylethylmethylene, methylbutylmethylene, methyl-t-butylmethylene, dihexylmethylene, dicyclohexylmethylene, methylcyclohexylmethylene, methylphenylmethylene, diphenylmethylene, ditolylmethylene, methylnaphthylmethylene, dinaphthylmethylene, 1-methylethylene, 1,2-dimethylethylene and 1-ethyl-2-methylethylene; cycloalkylidene groups such as cyclopropylidene, cyclobutylidene, cyclopentylidene, cyclohexylidene, cycloheptylidene, bicyclo[3.3.1]nonylidene, norbornylidene, adamantylidene, tetrahydronaphthylidene and dihydroindanylidene; and alkylidene groups such as ethylidene, propylidene and butylidene.

Examples of the halogen-containing groups include groups corresponding to the above alkylene groups, substituted alkylene groups and alkylidene groups or silicon-containing groups except that at least one hydrogen atom is substituted with an appropriate halogen atom. Specific examples include bis(trifluoromethyl)methylene, 4,4,4-trifluorobutylmethylmethylene, bis(trifluoromethyl)silylene and 4,4,4-trifluorobutylmethylsilylene.

Examples of the silicon-containing groups include silylene, methylsilylene, dimethylsilylene, diisopropylsilylene, dibutylsilylene, methylbutylsilylene, methyl-t-butylsilylene, dicyclohexylsilylene, methylcyclohexylsilylene, methylphenylsilylene, diphenylsilylene, ditolylsilylene, methylnaphthylsilylene, dinaphthylsilylene, cyclodimethylenesilylene, cyclotrimethylenesilylene, cyclotetramethylenesilylene, cyclopentamethylenesilylene, cyclohexamethylenesilylene and cycloheptamethylenesilylene. Examples of the germanium- or tin-containing groups include groups corresponding to the above silicon-containing groups except that the silicon is replaced by germanium or tin.

Alternatively, $Q^1$ may have a structure represented by Formula [8] or [9] below:

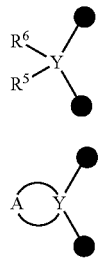

[8]

[9]

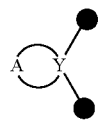

In the above formulae, Y is selected from a carbon atom, a silicon atom, a germanium atom and a tin atom; $R^5$ and $R^6$ are selected from a hydrogen atom, hydrocarbon groups, silicon-containing groups, heteroatom-containing groups and halogen-containing groups and are the same or different from each other; A indicates a C2-20 divalent hydrocarbon group which may have an unsaturated bond; A may have two or more ring structures inclusive of the ring formed by A and Y; and the black dots (•) indicate bonding points with the substituted cyclopentadienyl group and the cyclopentadienyl group.

In Formulae [8] and [9], Y is preferably a carbon atom or a silicon atom, and is particularly preferably a silicon atom.

Examples of the hydrocarbon groups, the silicon-containing groups, the heteroatom-containing groups and the halogen-containing groups indicated by $R^5$ and $R^6$ in Formula [8] include similar groups as represented by $R^1$, $R^2$, $R^3$ and $R^4$. Of the hydrocarbon groups, methyl group, chloromethyl group, ethyl group, n-propyl group, isopropyl group, n-butyl group, isobutyl group, t-butyl group, n-pentyl group, cyclopentyl group, cyclohexyl group, cycloheptyl group, phenyl group, m-tolyl group and p-tolyl group are preferable, and methyl group, chloromethyl group, n-butyl group, n-pentyl group and phenyl group are particularly preferred.

In Formula [9], A is a C2-20 divalent hydrocarbon group which may have an unsaturated bond, and Y and A together form a ring such as 1-silacyclopentylidene group. In the specification, the 1-silacyclopentylidene group is represented by Formula [10] below:

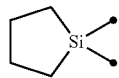

[10]

In Formula [10], the black dots (•) are as described in Formula [9].

The group A may have two or more ring structures inclusive of the ring formed by A and Y.

Preferred groups indicated by $Q^1$ include alkylene groups, substituted alkylene groups, alkylidene groups, halogen-containing alkylene groups, halogen-containing substituted alkylene groups, halogen-containing alkylidene groups, silicon-containing groups and halogen-containing silicon-containing groups each having 1 to 20 carbon atoms, with silicon-containing groups and halogen-containing silicon-containing groups being particularly preferable.

In Formula (1), X independently at each occurrence is an atom or a group selected from a hydrogen atom, halogen atoms, hydrocarbon groups, anionic ligands and neutral ligands capable of coordination through lone-pair electrons, and the plurality of X may be the same or different from each other.

Examples of the halogens include fluorine, chlorine, bromine and iodine. Specific examples of the hydrocarbon groups are as described hereinabove.

Specific examples of the anionic ligands include alkoxy groups and aryloxy groups such as methoxy, t-butoxy and phenoxy; carboxylate groups such as acetate and benzoate; and sulfonate groups such as mesylate and tosylate.

Specific examples of the neutral ligands capable of coordination through lone-pair electrons include organophosphorus compounds such as trimethylphosphine, triethylphosphine, triphenylphosphine and diphenylmethylphosphine; and ethers such as tetrahydrofuran, diethyl ether, dioxane and 1,2-dimethoxyethane. Preferably, at least one X is a halogen atom or an alkyl group.

In a preferred embodiment, at least one of $R^1$, $R^2$, $R^3$ and $R^4$ in Formula [1] is selected from the ethyl group, the groups represented by Formula [6] and the groups represented by Formula [7]. In a more preferred embodiment, one of $R^1$, $R^2$, $R^3$ and $R^4$ is selected from the ethyl group, the groups of Formula [6] and the groups of Formula [7], and more preferably $R^2$ or $R^3$ is selected from the ethyl group, the groups represented by Formula [6] and the groups represented by Formula [7]. In a particularly preferred embodiment, $R^3$ is selected from the ethyl group, the groups of Formula [6] and the groups of Formula [7], and $R^1$, $R^2$ and $R^4$ are all hydrogen atoms.

Specific examples of the transition metal compounds as the components (A) represented by Formula [1] are given below.

Specific examples include bridged asymmetric metallocene compounds having an alkylene group as the bridging group, such as ethylene(cyclopentadienyl)(2-methylcyclopentadienyl) zirconium dichloride, ethylene(cyclopentadienyl) (3-methylcyclopentadienyl)zirconium dichloride, ethylene(cyclopentadienyl)(2-ethylcyclopentadienyl) zirconium dichloride, ethylene(cyclopentadienyl) (3-ethylcyclopentadienyl) zirconium dichloride, ethylene(cyclopentadienyl)(2-n-propylcyclopentadienyl) zirconium dichloride, ethylene(cyclopentadienyl) (2-n-butylcyclopentadienyl)zirconium dichloride, ethylene(cyclopentadienyl)(3-n-propylcyclopentadienyl) zirconium dichloride, ethylene(cyclopentadienyl) (3-n-butylcyclopentadienyl)zirconium dichloride, ethylene(cyclopentadienyl)(3-n-pentylcyclopentadienyl) zirconium dichloride, ethylene(cyclopentadienyl) (3-n-hexylcyclopentadienyl)zirconium dichloride, ethylene(cyclopentadienyl)(3-n-octylcyclopentadienyl) zirconium dichloride, ethylene(cyclopentadienyl) (3-n-decylcyclopentadienyl)zirconium dichloride, ethylene(cyclopentadienyl)(2,3-dimethylcyclopentadienyl) zirconium dichloride, ethylene(cyclopentadienyl) (2,4-dimethylcyclopentadienyl)zirconium dichloride, ethylene(cyclopentadienyl)(2,5-dimethylcyclopentadienyl) zirconium dichloride, ethylene(cyclopentadienyl) (3,4-dimethylcyclopentadienyl)zirconium dichloride, ethylene(cyclopentadienyl) (3,4-di-n-propylcyclopentadienyl)zirconium dichloride, ethylene(cyclopentadienyl)(3,4-di-n-butylcyclopentadienyl) zirconium dichloride, ethylene (cyclopentadienyl) (2,3-ethylmethylcyclopentadienyl) zirconium dichloride, ethylene(cyclopentadienyl) (2,4-ethylmethylcyclopentadienyl)zirconium dichloride, ethylene (cyclopentadienyl) (2,5-ethylmethylcyclopentadienyl)

zirconium dichloride, ethylene(cyclopentadienyl) (3-methyl-4-n-propylcyclopentadienyl)zirconium dichloride, ethylene (cyclopentadienyl) (3-methyl-4-n-butylcyclopentadienyl)zirconium dichloride, ethylene(cyclopentadienyl) (2,3,4-trimethylcyclopentadienyl)zirconium dichloride, ethylene (cyclopentadienyl) (2,3,5-trimethylcyclopentadienyl) zirconium dichloride, ethylene(cyclopentadienyl) (2,5-dimethyl-3-n-propylcyclopentadienyl)zirconium dichloride, ethylene(cyclopentadienyl) (2,5-dimethyl-3-n-butylcyclopentadienyl)zirconium dichloride, ethylene(cyclopentadienyl) (tetramethylcyclopentadienyl)zirconium dichloride, ethylene(cyclopentadienyl) (2,5-dimethyl-3,4-di-n-propylcyclopentadienyl)zirconium dichloride and ethylene(cyclopentadienyl) (2,5-dimethyl-3,4-di-n-butylcyclopentadienyl)zirconium dichloride;

bridged asymmetric metallocene compounds having a substituted alkylene group as the bridging group, such as isopropylidene(cyclopentadienyl)(2-methylcyclopentadienyl) zirconium dichloride, isopropylidene(cyclopentadienyl) (3-methylcyclopentadienyl)zirconium dichloride, isopropylidene(cyclopentadienyl)(2-ethylcyclopentadienyl) zirconium dichloride, isopropylidene(cyclopentadienyl) (3-ethylcyclopentadienyl) zirconium dichloride, isopropylidene (cyclopentadienyl) (2-n-propylcyclopentadienyl)zirconium dichloride, isopropylidene(cyclopentadienyl) (2-n-butylcyclopentadienyl)zirconium dichloride, isopropylidene(cyclopentadienyl) (3-n-propylcyclopentadienyl)zirconium dichloride, isopropylidene(cyclopentadienyl) (3-n-butylcyclopentadienyl)zirconium dichloride, isopropylidene (cyclopentadienyl) (3-n-pentylcyclopentadienyl)zirconium dichloride, isopropylidene(cyclopentadienyl) (3-n-hexylcyclopentadienyl)zirconium dichloride, isopropylidene(cyclopentadienyl) (3-n-octylcyclopentadienyl)zirconium dichloride, isopropylidene(cyclopentadienyl) (3-n-decylcyclopentadienyl)zirconium dichloride, isopropylidene (cyclopentadienyl) (2,3-dimethylcyclopentadienyl) zirconium dichloride, isopropylidene(cyclopentadienyl) (2,4-dimethylcyclopentadienyl)zirconium dichloride, isopropylidene(cyclopentadienyl) (2,5-dimethylcyclopentadienyl)zirconium dichloride, isopropylidene(cyclopentadienyl) (3,4-dimethylcyclopentadienyl)zirconium dichloride, isopropylidene(cyclopentadienyl) (3,4-di-n-propylcyclopentadienyl)zirconium dichloride, isopropylidene(cyclopentadienyl) (3,4-di-n-butylcyclopentadienyl)zirconium dichloride, isopropylidene(cyclopentadienyl) (2,3-ethylmethylcyclopentadienyl)zirconium dichloride, isopropylidene(cyclopentadienyl) (2,4-ethylmethylcyclopentadienyl)zirconium dichloride, isopropylidene(cyclopentadienyl) (2,5-ethylmethylcyclopentadienyl)zirconium dichloride, isopropylidene (cyclopentadienyl) (3-methyl-4-n-propylcyclopentadienyl) zirconium dichloride, isopropylidene(cyclopentadienyl) (3-methyl-4-n-butylcyclopentadienyl)zirconium dichloride, isopropylidene(cyclopentadienyl) (2,3,4-trimethylcyclopentadienyl)zirconium dichloride, isopropylidene(cyclopentadienyl) (2,3,5-trimethylcyclopentadienyl)zirconium dichloride, isopropylidene(cyclopentadienyl) (2,5-dimethyl-3-n-propylcyclopentadienyl)zirconium dichloride, isopropylidene(cyclopentadienyl) (2,5-dimethyl-3-n-butyl-cyclopentadienyl)zirconium dichloride, isopropylidene(cyclopentadienyl) (tetramethylcyclopentadienyl)zirconium dichloride, isopropylidene(cyclopentadienyl) (2,5-dimethyl-3,4-di-n-propylcyclopentadienyl)zirconium dichloride and isopropylidene(cyclopentadienyl) (2,5-dimethyl-3,4-di-n-butylcyclopentadienyl)zirconium dichloride; and bridged asymmetric metallocene compounds having a silicon-containing group as the bridging group, such as dimethylsilylene(cyclopentadienyl) (2-methylcyclopentadienyl)zirconium dichloride, dimethylsilylene(cyclopentadienyl) (3-methylcyclopentadienyl)zirconium dichloride, dimethylsilylene(cyclopentadienyl) (2-ethylcyclopentadienyl)zirconium dichloride, dimethylsilylene(cyclopentadienyl) (3-ethylcyclopentadienyl)zirconium dichloride, dimethylsilylene (cyclopentadienyl) (2-n-propylcyclopentadienyl)zirconium dichloride, dimethylsilylene(cyclopentadienyl) (2-n-butyl-cyclopentadienyl)zirconium dichloride, dimethylsilylene (cyclopentadienyl) (3-n-propylcyclopentadienyl)zirconium dichloride, dimethylsilylene(cyclopentadienyl) (3-n-butyl-cyclopentadienyl)zirconium dichloride, dimethylsilylene (cyclopentadienyl) (3-n-pentylcyclopentadienyl)zirconium dichloride, dimethylsilylene(cyclopentadienyl) (3-n-hexyl-cyclopentadienyl)zirconium dichloride, dimethylsilylene (cyclopentadienyl) (3-n-octylcyclopentadienyl)zirconium dichloride, dimethylsilylene(cyclopentadienyl) (3-n-decyl-cyclopentadienyl)zirconium dichloride, dimethylsilylene (cyclopentadienyl) (2,3-dimethylcyclopentadienyl)zirconium dichloride, dimethylsilylene(cyclopentadienyl) (2,4-dimethylcyclopentadienyl)zirconium dichloride, dimethylsilylene(cyclopentadienyl) (2,5-dimethylcyclopentadienyl)zirconium dichloride, dimethylsilylene(cyclopentadienyl) (3,4-dimethylcyclopentadienyl)zirconium dichloride, dimethylsilylene(cyclopentadienyl) (3,4-di-n-propylcyclopentadienyl)zirconium dichloride, dimethylsilylene(cyclopentadienyl) (3,4-di-n-butylcyclopentadienyl)zirconium dichloride, dimethylsilylene(cyclopentadienyl) (2,3-ethylmethylcyclopentadienyl)zirconium dichloride, dimethylsilylene(cyclopentadienyl) (2,4-ethylmethylcyclopentadienyl)zirconium dichloride, dimethylsilylene(cyclopentadienyl) (2,5-ethylmethylcyclopentadienyl)zirconium dichloride, dimethylsilylene(cyclopentadienyl) (3-methyl-4-n-propylcyclopentadienyl)zirconium dichloride, dimethylsilylene(cyclopentadienyl) (3-methyl-4-n-butylcyclopentadienyl)zirconium dichloride, dimethylsilylene (cyclopentadienyl) (2,3,4-trimethylcyclopentadienyl) zirconium dichloride, dimethylsilylene(cyclopentadienyl) (2,3,5-trimethylcyclopentadienyl)zirconium dichloride, dimethylsilylene(cyclopentadienyl) (2,5-dimethyl-3-n-propylcyclopentadienyl)zirconium dichloride, dimethylsilylene (cyclopentadienyl) (2,5-dimethyl-3-n-butylcyclopentadienyl)zirconium dichloride, dimethylsilylene (cyclopentadienyl) (tetramethylcyclopentadienyl)zirconium dichloride, dimethylsilylene(cyclopentadienyl) (2,5-dimethyl-3,4-di-n-propylcyclopentadienyl)zirconium dichloride and dimethylsilylene(cyclopentadienyl) (2,5-dimethyl-3,4-di-n-butylcyclopentadienyl)zirconium dichloride.

Examples further include bridged asymmetric metallocene compounds corresponding to the aforesaid compounds except that the isopropylidene bridging group of the substituted alkylene group is altered to a di-n-butylmethylene bridging group; bridged asymmetric metallocene compounds corresponding to the aforesaid compounds except that the dimethylsilylene bridging group of the silicon-containing group is altered to a di-n-butylsilylene bridging group; bridged asymmetric metallocene compounds corresponding to the aforesaid compounds except that at least one of the hydrogen atoms of the bridging group is replaced by a halogen atom; and bridged asymmetric metallocene compounds corresponding to the aforesaid compounds except that at least one of the hydrogen atoms of the substituent groups bonded to the cyclopentadienyl ring is replaced by a halogen atom. Examples further include bridged metallocene compounds as described above in which the central metal is titanium or hafnium. The compounds described above are not restrictive.

Of the compounds described above, bridged asymmetric metallocene compounds in which the bridge has a silicon-containing group such as a dimethylsilylene group are preferable, and particularly preferred examples of such compounds include dimethylsilylene(cyclopentadienyl) (3-ethylcyclopentadienyl)zirconium dichloride, dimethylsilylene(cyclopentadienyl) (3-n-propylcyclopentadienyl)zirconium dichloride, dimethylsilylene(cyclopentadienyl) (3-n-butylcyclopentadienyl)zirconium dichloride, dimethylsilylene(cyclopentadienyl) (3-n-octylcyclopentadienyl)zirconium dichloride, dibutylsilylene(cyclopentadienyl) (3-n-propylcyclopentadienyl)zirconium dichloride, dimethylsilylene(cyclopentadienyl) (3-n-butylcyclopentadienyl)zirconium dichloride, dimethylsilylene(cyclopentadienyl) (3-n-octylcyclopentadienyl)zirconium dichloride, trifluoromethylbutylsilylene (cyclopentadienyl) (3-n-propylcyclopentadienyl) zirconium dichloride, trifluoromethylbutylsilylene (cyclopentadienyl) (3-n-butylcyclopentadienyl) zirconium dichloride and trifluoromethylbutylsilylene (cyclopentadienyl) (3-n-octylcyclopentadienyl) zirconium dichloride. In the invention, there may be used two or more kinds of the metallocene compounds of Formula [1] differing in structure from each other, or a mixture of optical isomers (a meso isomer/racemic isomer mixture). The bridged metallocene compounds of the present invention are not limited to the compounds described above and include any other compounds that meet the requirements set forth in the claims of the invention.

Processes for Producing Bridged Metallocene Compounds

The bridged metallocene compounds of the invention may be produced by any methods without limitation. For example, reference may be made to WO 01/027124. As an example, a compound represented by Formula [1] in which Q1 is a structure of Formula [8] or [9] may be manufactured by the following steps.

First, a precursor compound (10) or (19) for Formula [1] may be produced by a process [A] or [C].

When Y is carbon, a precursor compound (10) or (19) for Formula [1] may be produced by a process [B] or [D].

[A]

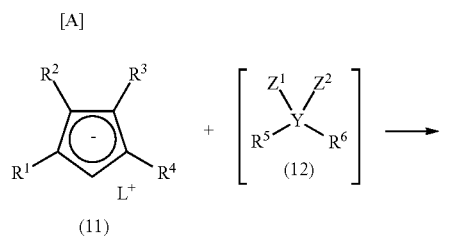

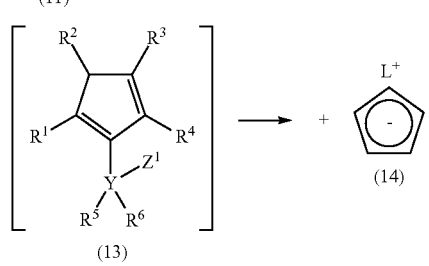

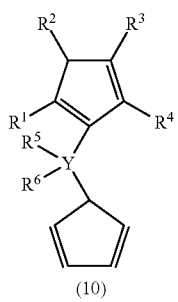

[B]

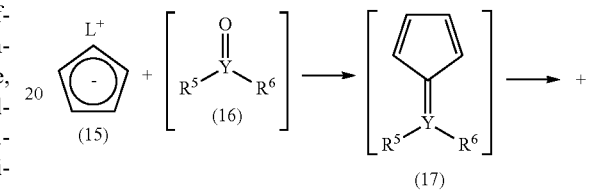

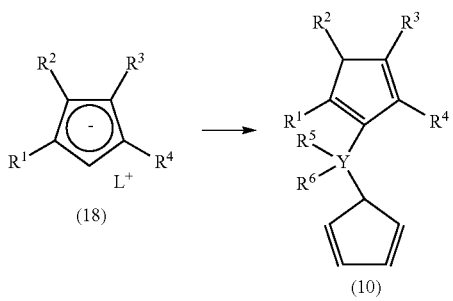

[C]

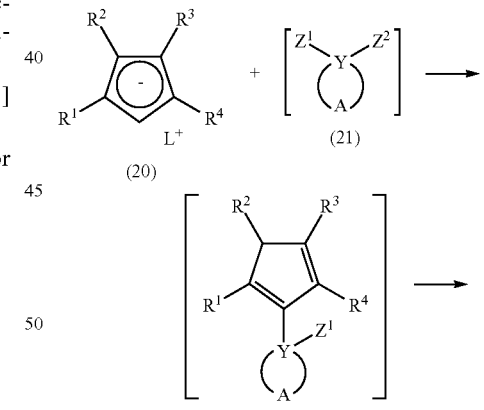

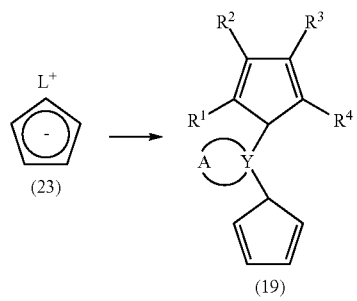

[D]

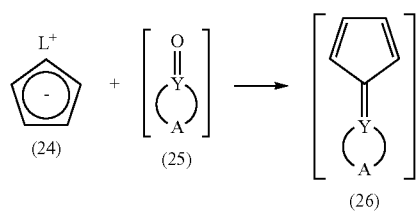

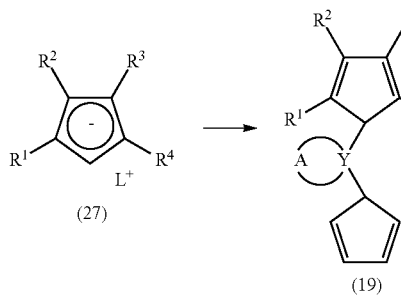

In the formulae above, $R^1$ to $R^6$ and Y are the same as described in Formulae [8] and [9]; L is an alkali metal or an alkaline earth metal; $Z^1$ and $Z^2$ are each a halogen or an anionic ligand and may be the same or different from each other; and the compounds (10) and (19) have isomers differing in the position of the double bonds in the cyclopentadienyl rings, and although the above formulae show only one kind of such isomers, other isomers differing in the position of the double bonds in the cyclopentadienyl rings or mixtures of such isomers may be used.

Examples of the alkali metals used in the reactions [A] to [D] include lithium, sodium and potassium, and examples of the alkaline earth metals include magnesium and calcium. Examples of the halogens include fluorine, chlorine, bromine and iodine. Examples of the anionic ligands include alkoxy groups such as methoxy, tert-butoxy and phenoxy; carboxylate groups such as acetate and benzoate; and sulfonate groups such as mesylate and tosylate.

The metallocene compounds may be produced from the precursor compounds (10) or (19) as illustrated in Formula [E] or [F]. These processes do not limit the scope of the invention, and the metallocene compounds may be synthesized by any other known methods.

[E]

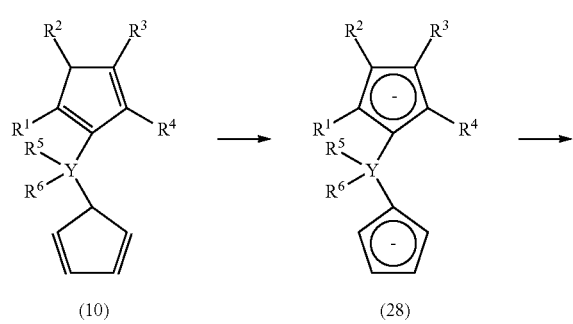

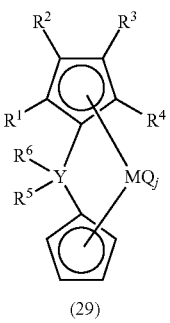

[F]

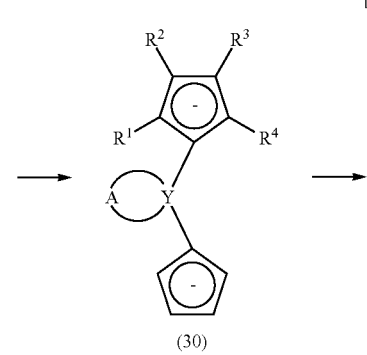

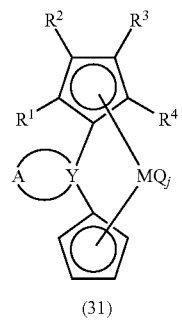

The precursor compound (10) or (19) obtained by any of the reactions [A] to [D] is brought into contact with an alkali metal, an alkali metal hydride or an organic alkali metal in an organic solvent at a reaction temperature of −80 to 200° C. to give a dialkali metal salt.

The organic solvents used in the above reaction include aliphatic hydrocarbons such as pentane, hexane, heptane, cyclohexane and decalin; aromatic hydrocarbons such as benzene, toluene and xylene; ethers such as THF, di-n-butyl ether, cyclopentylmethyl ether, dioxane and 1,2-dimethoxyethane; and halogenated hydrocarbons such as dichloromethane and chloroform.

The alkali metals used in the above reaction include lithium, sodium and potassium. The alkali metal hydrides include sodium hydride and potassium hydride. The organic alkali metals include methyllithium, butyllithium and phenyllithium.

Next, the dialkali metal salt (28) or (30) is subjected to the subsequent reaction, preferably after purification. The purification may be performed with solvents such as aliphatic hydrocarbons such as pentane, hexane, heptane, cyclohexane and decalin; aromatic hydrocarbons such as benzene, toluene and xylene; ethers such as THF, di-n-butyl ether, dioxane and 1,2-dimethoxyethane; and halogenated hydrocarbons such as dichloromethane and chloroform. Of these solvents, the aliphatic hydrocarbons such as pentane, hexane, heptane, cyclohexane and decalin are more preferable.

In the subsequent reaction, the dialkali metal salt (28) or (30) is reacted in an organic solvent with a compound represented by Formula (32):

$$MX_k \quad (32)$$

wherein M is a metal selected from titanium, zirconium and hafnium; a plurality of X are halogens, anionic ligands and neutral ligands capable of coordination through lone-pair electrons and may be the same or different from one another; and k is an integer of 3 to 6. The reaction results in a bridged metallocene compound of Formula [1]. To prevent the formation of by-products, preferred organic solvents are aliphatic hydrocarbons such as pentane, hexane, heptane, cyclohexane and decalin, and mixed solvents containing aliphatic hydrocarbons at not less than 50 wt % and ethers. The aliphatic hydrocarbons such as pentane, hexane, heptane, cyclohexane and decalin are particularly preferred.

Preferred examples of the compounds represented by Formula (32) are trivalent or tetravalent titanium fluoride, chloride, bromide and iodide; tetravalent zirconium fluoride, chloride, bromide and iodide; tetravalent hafnium fluoride, chloride, bromide and iodide; and complexes of these halides with ethers such as THF, di-n-butyl ether, dioxane and 1,2-dimethoxyethane.

The organic solvents used herein are similar to those described hereinabove. The dialkali metal salt and the compound of Formula (32) are preferably reacted in equimolar amounts in the organic solvent at a reaction temperature of −80 to 200° C.

The metallocene compound from the reaction may be isolated and purified by methods such as extraction, recrystallization and sublimation. The bridged metallocene compounds according to the invention obtained by the above processes may be identified by techniques such as proton nuclear magnetic resonance spectroscopy, $^{13}C$ nuclear magnetic resonance spectroscopy, mass spectrometry and elemental analysis.

Olefin Polymerization Catalysts (a)

The olefin polymerization catalysts (a) contain the components (A) and (C).

Component (A): the bridged metallocene compound represented by Formula [1] above.

Component (C): at least one compound selected from the group consisting of:

(c-1) organometallic compounds represented by Formulae [11], [12] and [13] below;
(c-2) organoaluminum oxy-compounds; and
(c-3) compounds that react with the component (A) to form an ion pair;

$$R^a{}_m Al(OR^b)_n H_p X_q \quad [11]$$

wherein $R^a$ and $R^b$ are each a C1-15 hydrocarbon group and are the same or different from each other; X is a halogen atom; $0 < m \leq 3$, $0 \leq n < 3$, $0 \leq p < 3$, $0 \leq q < 3$ and $m+n+p+q=3$;

$$M^a AlR^a{}_4 \quad [12]$$

wherein $M^a$ is Li, Na or K; and $R^a$ is a C1-15 hydrocarbon group;

$$R^a{}_r M^b R^b{}_s X_t \quad [13]$$

wherein $R^a$ and $R^b$ are each a C1-15 hydrocarbon group and are the same or different from each other; $M^b$ is selected from Mg, Zn and Cd; X is a halogen atom; $0 < r \leq 2$, $0 \leq s \leq 1$, $0 \leq t \leq 1$ and $r+s+t=2$.

The olefin polymerization catalysts may further contain a solid carrier (S) as required.

The component (C) and the solid carrier (S) will be described in detail below.

Components (C)

The compounds (c-1) may be those compounds disclosed in JP-A-H11-315109 and EP0874005A filed by the present applicant.

Of the organometallic compounds (c-1) represented by Formulae [11], [12] and [13], those having Formula [11] are preferable. Specific examples thereof include trialkylaluminums such as trimethylaluminum, triethylaluminum, triisopropylaluminum, triisobutylaluminum, trihexylaluminum, trioctylaluminum and tri-2-ethylhexylaluminum; dialkylaluminum halides such as dimethylaluminum chloride, diethylaluminum chloride, diisopropylaluminum chloride, diisobutylaluminum chloride and dimethylaluminum bromide; alkylaluminum sesquihalides such as methylaluminum sesquichloride, ethylaluminum sesquichloride, isopropylaluminum sesquichloride, butylaluminum sesquichloride and ethylaluminum sesquibromide; alkylaluminum dihalides such as methylaluminum dichloride, ethylaluminum dichloride, isopropylaluminum dichloride and ethylaluminum dibromide; alkylaluminum hydrides such as dimethylaluminum hydride, diethylaluminum hydride, dihydrophenylaluminum hydride, diisopropylaluminum hydride, di-n-butylaluminum hydride, diisobutylaluminum hydride, diisohexylaluminum hydride, diphenylaluminum hydride, dicyclohexylaluminum hydride, di-sec-heptylaluminum hydride and di-sec-nonylaluminum hydride; and dialkylaluminum alkoxides such as dimethylaluminum ethoxide, diethylaluminum ethoxide, diisopropylaluminum methoxide and diisobutylaluminum ethoxide.

These compounds may be used singly, or two or more kinds may be used in combination.

Preferred organoaluminum oxy-compounds (c-2) are aluminoxanes prepared from trialkylaluminums or tricycloalkylaluminums. In particular, organoaluminum oxy-compounds prepared from trimethylaluminum or triisobutylaluminum are preferable. The organoaluminum oxy-compounds may be used singly, or two or more kinds may be used in combination.

Examples of the compounds (c-3) capable of reacting with the component (A) to form an ion pair include Lewis acids, ionic compounds, borane compounds and carborane compounds as described in JP-A-H01-501950, JP-A-H01-502036, JP-A-H03-179005, JP-A-H03-179006, JP-A-H03-207703, JP-A-H03-207704, and U.S. Pat. No. 5,321,106. Heteropoly compounds and isopoly compounds may also be employed. These compounds may be used without limitation.

When the olefin polymerization catalyst of the invention is used together with an organoaluminum oxy-compound such as methylaluminoxane as a cocatalyst component, the catalyst shows very high polymerization activity for olefin compounds. Further, an organoaluminum oxy-compound reacts with the active hydrogen in the solid carrier, and a solid carrier component containing the cocatalyst component may be prepared easily. In view of these advantages, it is preferable to use the organoaluminum oxy-compound (c-2) as component (C).

Solid Carriers (S)

The solid carriers (S) will be described next. The solid carriers (S) may be simply referred to as the components (S).

The solid carrier (S) optionally used in the invention is an inorganic or organic compound in the form of granular or fine particulate solid. The components described hereinabove are supported on the solid carrier.

Examples of the inorganic compounds include porous oxides, inorganic halides, clays, clay minerals and ion-exchange layered compounds. Preferably, porous oxides or inorganic halides described below are used.

Examples of the porous oxides include $SiO_2$, $Al_2O_3$, MgO, ZrO, $TiO_2$, $B_2O_3$, CaO, ZnO, BaO, $ThO_2$, and complexes and mixtures containing these oxides, such as natural or synthetic zeolites, $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Of these, those containing $SiO_2$ as the major component are preferable.

The inorganic oxides may contain small amounts of carbonate, sulfate, nitrate or oxide components such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$.

Although these porous oxides have various properties depending on the type and preparation process thereof, the carrier suitable for use in the invention has a particle diameter of 0.2 to 300 μm, preferably 1 to 200 μm, a specific surface area of 50 to 1200 $m^2/g$, preferably 100 to 1000 $m^2/g$, and a pore volume of 0.3 to 30 $cm^3/g$. Where necessary, the carrier may be calcined at 100 to 1000° C., and preferably 150 to 700° C. before use.

Examples of the inorganic halides include $MgCl_2$, $MgBr_2$, $MnCl_2$ and $MnBr_2$. The inorganic halides may be used as they are or after pulverized by a ball mill, a vibration mill or the like. Alternatively, the inorganic halides may be dissolved in a solvent such as an alcohol and then precipitated by a precipitating agent to be used in the form of fine particles.

The clays are generally comprised of a clay mineral as the major component. The ion-exchange layered compounds have a crystal structure in which planes formed by ionic bonding or the like pile on one another in parallel with a weak bond strength, and they contain exchangeable ions. Most clay minerals are ion-exchange layered compounds. The clays, the clay minerals and the ion-exchange layered compounds are not limited to naturally occurring materials and may be synthetic.

Examples of such clays, clay minerals and ion-exchange layered compounds include clays, clay minerals, and ion crystalline compounds having such a layered crystal structure as a hexagonal closest packing type, an antimony type, a $CdCl_2$ type or a $CdI_2$ type.

Specific examples of the clays and the clay minerals include kaolin, bentonite, kibushi clay, potter's clay, allophane, hisingerite, pyrophyllite, mica group, montmorillonite group, vermiculite, chlorite group, palygorskite, kaolinite, nacrite, dickite and halloysite. Specific examples of the ion-exchange layered compounds include crystalline acid salts of polyvalent metals, such as α-$Zr(HAsO_4)_2.H_2O$, α-$Zr(HPO_4)_2$, α-$Zr(KPO_4)_2.3H_2O$, α-$Ti(HPO_4)_2$, α-$Ti(HAsO_4)_2.H_2O$, α-$Sn(HPO_4)_2.H_2O$, γ-$Zr(HPO_4)_2$, γ-$Ti(HPO_4)_2$ and γ-$Ti(NH_4PO_4)_2.H_2O$.

The clays, the clay minerals and the ion-exchange layered compounds preferably have a pore volume, as measured on pores having a radius of not less than 20 Å by a mercury penetration method, of 0.1 cc/g or more, particularly from 0.3 to 5 cc/g. The pore volume is measured on the pores having a radius of 20 to $3 \times 10^4$ Å by a mercury penetration method using a mercury porosimeter.

When the carrier used has a pore volume of less than 0.1 cc/g as measured on pores having a radius of 20 Å or more, it tends to be difficult to obtain high polymerization activity.

It is preferable that the clays and the clay minerals are chemically treated. Any chemical treatment may be used herein, for example a surface treatment to remove impurities attached to the surface or a treatment to affect the crystal structure of the clay. Specific examples of such chemical treatments include acid treatment, alkali treatment, salt treatment and organic matter treatment. The acid treatment removes impurities from the surface and increases the surface area by dissolving cations such as of Al, Fe and Mg from the crystal structure. The alkali treatment destroys the crystal structure of the clay to bring about change in clay structure. The salt treatment and the organic matter treatment produce an ionic complex, a molecular complex or an organic derivative to cause change in surface area or interlayer distance.

The ion-exchange layered compound may be enlarged in interlayer distance by changing the exchangeable ions between layers with other larger and bulkier ions by means of ion exchange properties. The bulky ions play a pillar-like roll to support the layered structure and are called pillars. Introduction of other substances between layers of a layered compound is called intercalation. Examples of the guest compounds to be intercalated include cationic inorganic compounds such as $TiCl_4$ and $ZrCl_4$; metal alkoxides such as $Ti(OR)_4$, $Zr(OR)_4$, $PO(OR)_3$ and $B(OR)_3$ (wherein R is a hydrocarbon group or the like); and metal hydroxide ions such as $[Al_{13}O_4(OH)_{24}]^{7+}$, $[Zr_4(OH)_{14}]^{2+}$ and $[Fe_3O(OCOCH_3)_6]^+$. These compounds may be used singly or in combination of two or more kinds. Intercalation of these compounds can be carried out in the presence of polymers obtained by hydrolysis of metal alkoxides such as $Si(OR)_4$, $Al(OR)_3$ and $Ge(OR)_4$ (wherein R is a hydrocarbon group or the like) or in the presence of colloidal inorganic compounds such as $SiO_2$. Examples of the pillars include oxides resulting from thermal dehydration of the above-mentioned metal hydroxide ions intercalated between layers.

The clays, the clay minerals and the ion-exchange layered compounds mentioned above may be used as they are or after treated by, for example, ball milling or sieving. They may be used after subjected to water adsorption or thermal dehydration. The clays, the clay minerals and the ion-exchange layered compounds may be used singly or in combination of two or more kinds.

The organic compound is, for example, a granular or fine particulate solid ranging in particle diameter from 10 to 300 μm. Specific examples thereof include (co)polymers mainly composed of a C2-14 olefin such as ethylene, propylene, 1-butene or 4-methyl-1-pentene, (co)polymers or reaction products formed mainly of vinylcyclohexane, styrene or divinylbenzene, and modified products of these compounds.

The olefin polymerization catalysts of the invention contain the bridged metallocene compound (A), at least one compound (C) selected from the organometallic compounds (c-1) of Formulae [11], [12] and [13], the organoaluminum oxy-compounds (c-2) and the ionized ionic compounds (c-3), and optionally the components (S) as required.

In carrying out the polymerization, the components may be used and added by any method or in any order. Some exemplary processes are given below:

(1) The component (A) alone is added to a polymerizer.

(2) The component (A) and the component (C) are added to a polymerizer in an arbitrary order.

(3) A catalyst component in which the component (A) is supported on the component (S), and the component (C) are added to a polymerizer in an arbitrary order.

(4) A catalyst component in which the component (C) is supported on the component (S), and the component (A) are added to a polymerizer in an arbitrary order.

(5) A catalyst component in which the components (A) and (C) are supported on the component (S) is added to a polymerizer.

In the processes (2) to (5), at least two of the catalyst components may be contacted with each other beforehand.

In the processes (4) and (5) in which the component (C) is supported on the carrier, other unsupported component (C)

may be added at an arbitrary stage as required. In this case, these components (C) may be the same or different from each other.

The solid catalyst component wherein the component (A) alone or the components (A) and (C) are supported on the component (S) may be prepolymerized with an olefin. Further, an additional catalyst component may be supported on the prepolymerized solid catalyst component.

In general, when a metallocene compound having substituent groups on both the cyclopentadienyl rings forms an ion pair with the component (C), the resultant olefin polymerization catalyst gives with high catalytic activity polymers having high molecular weight and less terminal double bonds.

The mechanism of this catalytic action is probably explained as follows. A number of substituent groups on the cyclopentadienyl rings produce steric hindrance which causes an appropriate distance between the central metal (cation) and the component (C) (anion) and consequently the acidity of the central metal is increased. As a result, the coordination and insertion of monomers are facilitated but at the same time the steric hindrance by the substituent groups inhibits chain transfer reactions which control the molecular weight such as a chain transfer reaction of monomers or a transfer of hydrogen at the β-position of the polymer chain to the central metal.

In contrast, the olefin polymerization catalysts (a) containing the bridged metallocene compound of Formula [1] have substituent groups on only one cyclopentadienyl ring. As a result, an appropriate distance is ensured between the central metal and the component (C) while ensuring an appropriate space to permit chain transfer reactions. The olefin polymerization catalysts of the present invention can thus achieve high polymerization activity and afford polymers having a low molecular weight and many double bonds at terminals.

Olefin Polymerization Catalysts (b)

The olefin polymerization catalysts (b) of the invention contain the component (A), the component (B) and the component (C).

Component (A): the bridged metallocene compound represented by Formula [1] above;

Component (B): a bridged metallocene compound represented by Formula [14] below:

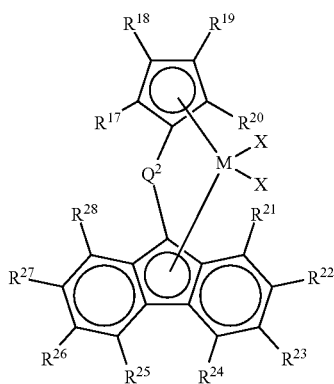

[14]

wherein $R^{17}$ to $R^{20}$, and $R^{21}$ to $R^{28}$ are selected from a hydrogen atom, hydrocarbon groups, halogen-containing groups, oxygen-containing groups, nitrogen-containing groups, boron-containing groups, sulfur-containing groups, phosphorus-containing groups, silicon-containing groups, germanium-containing groups and tin-containing groups and are the same or different from one another; neighboring substituent groups among these groups may be linked together to form a ring; $Q^2$ is selected from C1-20 hydrocarbon groups, halogen-containing groups, silicon-containing groups, germanium-containing groups and tin-containing groups; M is selected from a titanium atom, a zirconium atom and a hafnium atom; and X independently at each occurrence is a group selected from a hydrogen atom, halogen atoms, hydrocarbon groups, halogen-containing groups, silicon-containing groups, oxygen-containing groups, sulfur-containing groups, nitrogen-containing groups and phosphorus-containing groups;

Component (C): at least one compound selected from the group consisting of:

(c-1) organometallic compounds represented by Formulae [18], [19] and [20] below;

(c-2) organoaluminum oxy-compounds; and (c-4) compounds that react with the components (A) and (B) to form an ion pair;

$$R^a{}_m Al(OR^b)_n H_p X_q \quad [18]$$

wherein $R^a$ and $R^b$ are each a C1-15 hydrocarbon group and are the same or different from each other; X is a halogen atom; 0<m≤3, 0≤n<3, 0≤p<3, 0≤q<3 and m+n+p+q=3;

$$M^a AlR^a{}_4 \quad [19]$$

wherein $M^a$ is Li, Na or K; and $R^a$ is a C1-15 hydrocarbon group;

$$R^a{}_r M^b R^b{}_s X_t \quad [20]$$

wherein $R^a$ and $R^b$ are each a C1-15 hydrocarbon group and are the same or different from each other; $M^b$ is selected from Mg, Zn and Cd; X is a halogen atom; 0<r≤2, 0≤s≤1, 0≤t≤1 and r+s+t=2.

The olefin polymerization catalysts may further contain a solid carrier (S) as required.

The component (B), the component (C) and the solid carrier (S) will be described in detail below.

Component (B)

The bridged metallocene compounds as the components (B) are metallocene compounds of Group IV metal represented by Formula [14] below.

The metallocene compounds of Group IV metal represented by Formula [14] will be described in detail.

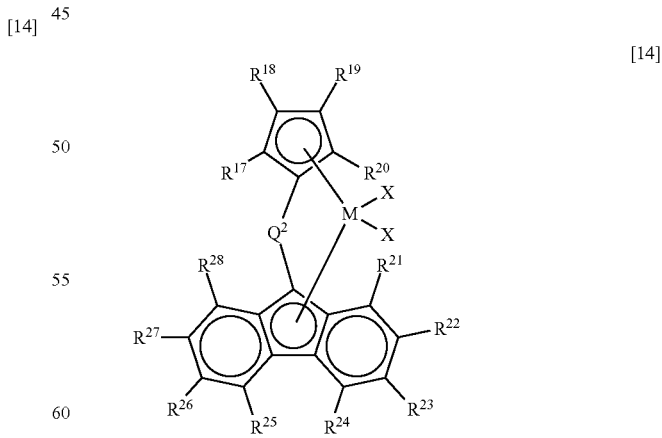

[14]

In Formula [14], M is a transition metal selected from titanium, zirconium and hafnium, and is preferably zirconium.

$R^{17}$ to $R^{20}$, and $R^{21}$ to $R^{28}$ are selected from a hydrogen atom, hydrocarbon groups, halogen-containing groups, oxygen-containing groups, nitrogen-containing groups, boron-containing groups, sulfur-containing groups, phosphorus-containing groups, silicon-containing groups, germanium-containing groups and tin-containing groups and are the same or different from one another. Neighboring two substituent groups among these groups may be linked together to form a ring.

$Q^2$ is a divalent group linking the two ligands and is selected from C1-20 hydrocarbon groups such as alkylene groups, substituted alkylene groups and alkylidene groups; halogen-containing groups; silicon-containing groups; germanium-containing groups; and tin-containing groups. Examples of these groups are as described for $Q^1$.

Preferred groups indicated by $Q^2$ include alkylene groups, substituted alkylene groups, alkylidene groups, halogen-containing alkylene groups, halogen-containing substituted alkylene groups and halogen-containing alkylidene groups each having 1 to 20 carbon atoms, and silicon-containing groups and halogen-containing silicon-containing groups. Of these, alkylene groups, substituted alkylene groups, alkylidene groups and silicon-containing groups each having 1 to 20 carbon atoms are particularly preferable.

Alternatively, $Q^2$ may have a structure represented by Formula [15] or [16] below:

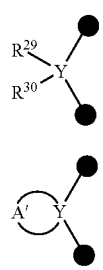

[15]

[16]

In the above formulae, Y is selected from a carbon atom, a silicon atom, a germanium atom and a tin atom; $R^{29}$ and $R^{30}$ are selected from a hydrogen atom, hydrocarbon groups, silicon-containing groups, heteroatom-containing groups and halogen-containing groups and are the same or different from each other; A' indicates a C2-20 divalent hydrocarbon group which may have an unsaturated bond; A' may have two or more ring structures inclusive of the ring formed by A' and Y; and the black dots (•) indicate bonding points with the substituted cyclopentadienyl group and the substituted fluorenyl group.

In Formulae [15] and [16], Y is preferably a carbon atom or a silicon atom, and is particularly preferably a carbon atom.

Examples of the hydrocarbon groups, the silicon-containing groups, the heteroatom-containing groups and the halogen-containing groups indicated by $R^{29}$ and $R^{30}$ in Formula [15] include similar groups as represented by $R^{17}$ to $R^{20}$, and $R^{21}$ to $R^{28}$. Of the hydrocarbon groups, methyl group, chloromethyl group, ethyl group, n-propyl group, isopropyl group, n-butyl group, isobutyl group, t-butyl group, n-pentyl group, cyclopentyl group, cyclohexyl group, cycloheptyl group, phenyl group, m-tolyl group and p-tolyl group are preferable, and methyl group, chloromethyl group, n-butyl group, n-pentyl group and phenyl group are particularly preferred.

In Formula [16], A' is a C2-20 divalent hydrocarbon group which may have an unsaturated bond, and Y and A' together form a ring such as 1-silacyclopentylidene group. In the specification, the 1-silacyclopentylidene group is represented by Formula [17] below:

[17]

In Formula [17], the black dots (•) are as described in Formula [16].

A' may have two or more ring structures inclusive of the ring formed by A' and Y.

Preferred groups indicated by $Q^2$ include alkylene groups, substituted alkylene groups, alkylidene groups, halogen-containing alkylene groups, halogen-containing substituted alkylene groups and halogen-containing alkylidene groups each having 1 to 20 carbon atoms, and silicon-containing groups and halogen-containing silicon-containing groups, with carbon-containing groups and halogen-containing carbon groups being particularly preferable.

The letter X independently at each occurrence is a group selected from a hydrogen atom, halogen atoms, hydrocarbon groups, halogen-containing hydrocarbon groups, silicon-containing groups, oxygen-containing groups, sulfur-containing groups, nitrogen-containing groups and phosphorus-containing groups. Of these, halogen atoms and hydrocarbon groups are preferable. Examples of the halogen atoms include fluorine, chlorine, bromine and iodine. Examples of the hydrocarbon groups, the halogen-containing hydrocarbon groups, the silicon-containing groups, the oxygen-containing groups, the sulfur-containing groups, the nitrogen-containing groups and the phosphorus-containing groups are as described above.

The hydrogen atom, the hydrocarbon groups, the halogen-containing groups, the oxygen-containing groups, the nitrogen-containing groups, the boron-containing groups, the sulfur-containing groups, the phosphorus-containing groups, the silicon-containing groups, the germanium-containing groups and the tin-containing groups indicated by $R^{17}$ to $R^{20}$, and $R^{21}$ to $R^{28}$ may be similar to those represented by $R^1$ to $R^4$ in Formula [1] without limitation. The atoms and the groups indicated by X may be similar to those represented by X in Formula [1] without limitation. In an embodiment, at least one pair of neighboring groups among $R^{17}$ to $R^{20}$ on the cyclopentadienyl ring may be linked together to form a ring, and consequently a ring structure such as an indenyl group, a substituted indenyl group, a fluorenyl group or a substituted fluorenyl group may be formed. In another embodiment, at least one pair of neighboring groups among $R^{21}$ to $R^{28}$ on the fluorenyl ring may be linked together to form a ring, and consequently a ring structure such as a benzofluorenyl group, a dibenzofluorenyl group, an octahydrodibenzofluorenyl group or an octamethyloctahydrodibenzofluorenyl group may be formed.

In a preferred embodiment of the above substituent groups, $R^{17}$ to $R^{20}$ are hydrogen atoms, $R^{21}$ to $R^{28}$ are selected from the hydrogen atom and the hydrocarbon groups, and at least one pair of neighboring hydrocarbon groups may be linked together to form an octahydrodibenzofluorenyl group or an octamethyloctahydrodibenzofluorenyl group. In a preferred embodiment, $Q^2$ is selected from the alkylene groups, substituted alkylene groups and alkylidene groups having 1 to 20 carbon atoms, and silicon-containing groups. When the bridged metallocene compound has these substituent groups and the bridging group, the obtainable catalyst relatively prevents an increase in molecular weight and permits reducing the amount of hydrogen required for molecular weight control, whereby it is expected that the component (A) affords an increased amount of macromonomers and the number of long-chain branches is increased.

Specific examples of the Group IV metallocene compounds represented by Formula [14] are given below but are not limited thereto:

isopropylidene(cyclopentadienyl)(fluorenyl)zirconium dichloride, isopropylidene(cyclopentadienyl) (2,7-di-tert-butylfluorenyl)zirconium dichloride, isopropylidene(cyclopentadienyl) (3,6-di-tert-butylfluorenyl)zirconium dichloride, isopropylidene(cyclopentadienyl) (octamethyloctahydridodibenzofluorenyl)zirconium dichloride, dibutylmethylene(cyclopentadienyl)(fluorenyl)zirconium dichloride, dibutylmethylene(cyclopentadienyl) (2,7-di-tert-butylfluorenyl)zirconium dichloride, dibutylmethylene(cyclopentadienyl) (3,6-di-tert-butylfluorenyl)zirconium dichloride, dibutylmethylene(cyclopentadienyl) (octamethyloctahydridodibenzofluorenyl)zirconium dichloride, diphenylmethylene(cyclopentadienyl)(fluorenyl)zirconium dichloride, diphenylmethylene(cyclopentadienyl) (2,7-di-tert-butylfluorenyl)zirconium dichloride, diphenylmethylene(cyclopentadienyl) (3,6-di-tert-butylfluorenyl)zirconium dichloride, diphenylmethylene(cyclopentadienyl) (octamethyloctahydridodibenzofluorenyl)zirconium dichloride, cyclohexylidene(cyclopentadienyl)(fluorenyl)zirconium dichloride, cyclohexylidene(cyclopentadienyl) (2,7-di-tert-butylfluorenyl)zirconium dichloride, cyclohexylidene(cyclopentadienyl) (3,6-di-tert-butylfluorenyl)zirconium dichloride, cyclohexylidene(cyclopentadienyl) (octamethyloctahydridodibenzofluorenyl)zirconium dichloride, phenylmethylmethylene(cyclopentadienyl)(fluorenyl) zirconium dichloride, phenylmethylmethylene(cyclopentadienyl) (2,7-di-tert-butylfluorenyl)zirconium dichloride, phenylmethylmethylene(cyclopentadienyl) (3,6-di-tert-butylfluorenyl)zirconium dichloride, phenylmethylmethylene(cyclopentadienyl) (octamethyloctahydridodibenzofluorenyl)zirconium dichloride, dimethylsilyl(cyclopentadienyl)(fluorenyl)zirconium dichloride, dimethylsilyl(cyclopentadienyl) (2,7-di-tert-butylfluorenyl)zirconium dichloride, dimethylsilyl(cyclopentadienyl) (3,6-di-tert-butylfluorenyl)zirconium dichloride, dimethylsilyl(cyclopentadienyl) (octamethyloctahydridodibenzofluorenyl)zirconium dichloride, isopropylidene(3-tert-butylcyclopentadienyl)(fluorenyl) zirconium dichloride, isopropylidene(3-tert-butylcyclopentadienyl) (2,7-di-tert-butylfluorenyl)zirconium dichloride, isopropylidene(3-tert-butylcyclopentadienyl) (3,6-di-tert-butylfluorenyl)zirconium dichloride, isopropylidene(3-tert-butylcyclopentadienyl) (octamethyloctahydridodibenzofluorenyl)zirconium dichloride, diphenylmethylene(3-tert-butylcyclopentadienyl) (fluorenyl)zirconium dichloride, diphenylmethylene(3-tert-butylcyclopentadienyl) (2,7-di-tert-butylfluorenyl)zirconium dichloride, diphenylmethylene(3-tert-butylcyclopentadienyl) (3,6-di-tert-butylfluorenyl)zirconium dichloride, diphenylmethylene(3-tert-butylcyclopentadienyl) (octamethyloctahydridodibenzofluorenyl)zirconium dichloride, cyclohexylidene(3-tert-butylcyclopentadienyl) (fluorenyl) zirconium dichloride, cyclohexylidene(3-tert-butylcyclopentadienyl) (2,7-di-tert-butylfluorenyl)zirconium dichloride, cyclohexylidene(3-tert-butylcyclopentadienyl) (3,6-di-tert-butylfluorenyl)zirconium dichloride, cyclohexylidene(3-tert-butylcyclopentadienyl) (octamethyloctahydridodibenzofluorenyl)zirconium dichloride, phenylmethylmethylene(3-tert-butylcyclopentadienyl) (fluorenyl)zirconium dichloride, phenylmethylmethylene(3-tert-butylcyclopentadienyl) (2,7-di-tert-butylfluorenyl)zirconium dichloride, phenylmethylmethylene(3-tert-butylcyclopentadienyl) (3,6-di-tert-butylfluorenyl)zirconium dichloride, phenylmethylmethylene(3-tert-butylcyclopentadienyl) (octamethyloctahydridodibenzofluorenyl)zirconium dichloride, isopropylidene(3-tert-butyl-5-methylcyclopentadienyl) (fluorenyl)zirconium dichloride, isopropylidene(3-tert-butyl-5-methylcyclopentadienyl) (2,7-di-tert-butylfluorenyl)zirconium dichloride, isopropylidene(3-tert-butyl-5-methylcyclopentadienyl) (3,6-di-tert-butylfluorenyl)zirconium dichloride, isopropylidene(3-tert-butyl-5-methylcyclopentadienyl) (octamethyloctahydridodibenzofluorenyl)zirconium dichloride, diphenylmethylene(3-tert-butyl-5-methylcyclopentadienyl) (fluorenyl)zirconium dichloride, diphenylmethylene(3-tert-butyl-5-methylcyclopentadienyl) (2,7-di-tert-butylfluorenyl)zirconium dichloride, diphenylmethylene(3-tert-butyl-5-methylcyclopentadienyl) (3,6-di-tert-butylfluorenyl)zirconium dichloride, diphenylmethylene(3-tert-butyl-5-methylcyclopentadienyl) (octamethyloctahydridodibenzofluorenyl)zirconium dichloride, cyclohexylidene(3-tert-butyl-5-methylcyclopentadienyl) (fluorenyl)zirconium dichloride, cyclohexylidene(3-tert-butyl-5-methylcyclopentadienyl) (2,7-di-tert-butylfluorenyl)zirconium dichloride, cyclohexylidene(3-tert-butyl-5-methylcyclopentadienyl) (3,6-di-tert-butylfluorenyl)zirconium dichloride, cyclohexylidene(3-tert-butyl-5-methylcyclopentadienyl) (octamethyloctahydridodibenzofluorenyl)zirconium dichloride, phenylmethylmethylene (3-tert-butyl-5-methylcyclopentadienyl)(fluorenyl) zirconium dichloride, phenylmethylmethylene (3-tert-butyl-5-methylcyclopentadienyl) (2,7-di-tert-butylfluorenyl)zirconium dichloride, phenylmethylmethylene (3-tert-butyl-5-methylcyclopentadienyl) (3,6-di-tert-butylfluorenyl)zirconium dichloride, phenylmethylmethylene (3-tert-butyl-5-methylcyclopentadienyl) (octamethyloctahydridodibenzofluorenyl)zirconium dichloride, and dibromide compounds, dialkyl compounds, diaralkyl compounds, disilyl compounds, dialkoxy compounds, dithiol compounds, disulfonic acid compounds, diamino compounds and diphosphine compounds of the above metallocene compounds, and compounds corresponding to the above metallocene compounds except that the central metal is replaced by titanium or hafnium.

Of the above metallocene compounds, preferred are isopropylidene(cyclopentadienyl)(fluorenyl)zirconium dichloride, isopropylidene(cyclopentadienyl) (2,7-di-tert-butylfluorenyl)zirconium dichloride, isopropylidene (cyclopentadienyl) (3,6-di-tert-butylfluorenyl)zirconium dichloride, isopropylidene(cyclopentadienyl) (octamethyloctahydridodibenzofluorenyl)zirconium dichloride, dibutylmethylene(cyclopentadienyl)(fluorenyl)zirconium dichloride, dibutylmethylene(cyclopentadienyl) (2,7-di-tert-butylfluorenyl)zirconium dichloride, dibutylmethylene (cyclopentadienyl) (3,6-di-tert-butylfluorenyl)zirconium dichloride, dibutylmethylene(cyclopentadienyl) (octamethyloctahydridodibenzofluorenyl)zirconium dichloride, cyclohexylidene(cyclopentadienyl)(fluorenyl)zirconium dichloride, cyclohexylidene(cyclopentadienyl) (2,7-di-tert-butylfluorenyl)zirconium dichloride, cyclohexylidene (cyclopentadienyl) (3,6-di-tert-butylfluorenyl)zirconium dichloride, cyclohexylidene(cyclopentadienyl) (octamethyloctahydridodibenzofluorenyl)zirconium dichloride, dimethylsilyl(cyclopentadienyl)(fluorenyl)zirconium dichloride, dimethylsilyl(cyclopentadienyl) (2,7-di-tert-butylfluorenyl)

zirconium dichloride, dimethylsilyl(cyclopentadienyl) (3,6-di-tert-butylfluorenyl)zirconium dichloride and dimethylsilyl(cyclopentadienyl) (octamethyloctahydridodibenzofluorenyl)zirconium dichloride.

Specific examples of the metallocene compounds in which neighboring groups among $R^{17}$ to $R^{20}$ on the cyclopentadienyl ring are linked together to form an indenyl ring or a substituted indenyl ring include isopropylidene(indenyl) (fluorenyl) zirconium dichloride, isopropylidene(indenyl) (2,7-di-tert-butylfluorenyl)zirconium dichloride, isopropylidene(indenyl)(3,6-di-tert-butylfluorenyl) zirconium dichloride, isopropylidene(indenyl) (octamethyloctahydridodibenzofluorenyl)zirconium dichloride, cyclohexylidene(indenyl) (fluorenyl)zirconium dichloride, cyclohexylidene(indenyl). (2,7-di-tert-butylfluorenyl)zirconium dichloride, isopropylidene(indenyl)(3,6-di-tert-butylfluorenyl) zirconium dichloride, isopropylidene(indenyl) (octamethyloctahydridodibenzofluorenyl)zirconium dichloride, cyclohexylidene(indenyl) (fluorenyl)zirconium dichloride, cyclohexylidene(indenyl) (2,7-di-tert-butylfluorenyl)zirconium dichloride, cyclohexylidene(indenyl)(3,6-di-tert-butylfluorenyl) zirconium dichloride, cyclohexylidene(indenyl) (octamethyloctahydridodibenzofluorenyl)zirconium dichloride, dimethylsilyl (indenyl)(fluorenyl)zirconium dichloride, dimethylsilyl (indenyl) (2,7-di-tert-butylfluorenyl)zirconium dichloride, dimethylsilyl(indenyl)(3,6-di-tert-butylfluorenyl) zirconium dichloride and dimethylsilyl(indenyl) (octamethyloctahydridodibenzofluorenyl)zirconium dichloride. In the invention, two or more differing kinds of the metallocene compounds represented by Formula [14] may be used without limitation.

The bridged metallocene compounds represented by Formula [14] are disclosed in WO 01/27124.

Components (C)

(c-1) Organometallic compounds represented by Formulae [18], [19] and [20];

(c-2) organoaluminum oxy-compounds; and (c-4) compounds that react with the components (A) and (B) to form an ion pair.

The compounds (c-1) may be those compounds disclosed in JP-A-H11-315109 and EP0874005A filed by the present applicant.

Of the organometallic compounds (c-1) represented by Formulae [18], [19] and [20], those having Formula [18] are preferable. Specific examples of such compounds include trialkylaluminums such as trimethylaluminum, triethylaluminum, triisopropylaluminum, triisobutylaluminum, trihexylaluminum, trioctylaluminum and tri-2-ethylhexylaluminum; dialkylaluminum halides such as dimethylaluminum chloride, diethylaluminum chloride, diisopropylaluminum chloride, diisobutylaluminum chloride and dimethylaluminum bromide; alkylaluminum sesquihalides such as methylaluminum sesquichloride, ethylaluminum sesquichloride, isopropylaluminum sesquichloride, butylaluminum sesquichloride and ethylaluminum sesquibromide; alkylaluminum dihalides such as methylaluminum dichloride, ethylaluminum dichloride, isopropylaluminum dichloride and ethylaluminum dibromide; alkylaluminum hydrides such as dimethylaluminum hydride, diethylaluminum hydride, dihydrophenylaluminum hydride, diisopropylaluminum hydride, di-n-butylaluminum hydride, diisobutylaluminum hydride, diisohexylaluminum hydride, diphenylaluminum hydride, dicyclohexylaluminum hydride, di-sec-heptylaluminum hydride and di-sec-nonylaluminum hydride; and dialkylaluminum alkoxides such as dimethylaluminum ethoxide, diethylaluminum ethoxide, diisopropylaluminum methoxide and diisobutylaluminum ethoxide.

These compounds may be used singly, or two or more kinds may be used in combination.

Preferred organoaluminum oxy-compounds (c-2) are aluminoxanes prepared from trialkylaluminums or tricycloalkylaluminums. In particular, organoaluminum oxy-compounds prepared from trimethylaluminum or triisobutylaluminum are preferable. The organoaluminum oxy-compounds may be used singly, or two or more kinds may be used in combination.

Examples of the compounds (c-4) capable of reacting with the component (A) and the component (B) to form an ion pair include Lewis acids, ionic compounds, borane compounds and carborane compounds as described in JP-A-H01-501950, JP-A-H01-502036, JP-A-H03-179005, JP-A-H03-179006, JP-A-H03-207703, JP-A-H03-207704, and U.S. Pat. No. 5,321,106. Heteropoly compounds and isopoly compounds may also be employed. These compounds may be used without limitation.

When the olefin polymerization catalyst of the invention is used together with an organoaluminum oxy-compound such as methylaluminoxane as a cocatalyst component, the catalyst shows very high polymerization activity for olefin compounds. Further, an organoaluminum oxy-compound reacts with the active hydrogen in the solid carrier, and a solid carrier component containing the cocatalyst component may be prepared easily. In view of these advantages, it is preferable to use the organoaluminum oxy-compound (c-2) as component (C).

Solid Carriers (S)

The solid carriers (S) will be described next. The solid carriers (S) may be simply referred to as the components (S).

The solid carrier (S) optionally used in the invention is an inorganic or organic compound in the form of granular or fine particulate solid. The components described hereinabove are supported on the solid carrier.

Examples of the inorganic compounds and the organic compounds are as described hereinabove, with the porous oxides and the inorganic halides such as inorganic chlorides being preferable.

The olefin polymerization catalysts of the invention may be prepared as described below.

In a first embodiment, the olefin polymerization catalysts of the invention may be prepared by adding the components (A), (B) and (C) to an inert hydrocarbon or a polymerization system containing an inert hydrocarbon.

The components may be added in any order, but are preferably added in exemplary orders as described below.

i) The components are added to a polymerization system in the order of the component (C), the component (A) and the component (B).

ii) The components are added to a polymerization system in the order of the component (C), the component (B) and the component (A).

iii) The component (A) and the component (C) are mixed and contacted together. The contact product is added to a polymerization system and thereafter the component (B) is added to the polymerization system.

iv) The component (B) and the component (C) are mixed and contacted together. The contact product is added to a polymerization system and thereafter the component (A) is added to the polymerization system.

v) The component (C) is added to a polymerization system. The component (A) and the component (B) are mixed and contacted together, and the contact product is added to the polymerization system.

vi) The components are added to a polymerization system in the order of the component (C), the component (A) and the component (B). The component (C) is thereafter added again to the polymerization system.

vii) The components are added to a polymerization system in the order of the component (C), the component (B) and the component (A). The component (C) is thereafter added again to the polymerization system.

viii) The component (A) and the component (C) are mixed and contacted together, and the contact product is added to a polymerization system. The component (B) is thereafter added to the polymerization system, and the component (C) is added again to the polymerization system.

ix) The component (B) and the component (C) are mixed and contacted together, and the contact product is added to a polymerization system. The component (A) is thereafter added to the polymerization system, and the component (C) is added again to the polymerization system.

x) The component (C) is added to a polymerization system. The component (A) and the component (B) are mixed and contacted together, and the contact product is added to the polymerization system. The component (C) is added again to the polymerization system.

Of these, the addition sequences i), ii) and v) are particularly preferred.

In a second embodiment, the olefin polymerization catalysts of the invention may be prepared by adding a solid catalyst component (K1) formed of the solid carrier (S) and the components (C) and (A), and a solid catalyst component (K2) formed of the solid carrier (S) and the components (C) and (B) to an inert hydrocarbon or a polymerization system containing an inert hydrocarbon.

The components may be brought into contact in any order, but are preferably contacted in exemplary orders as described below.

xi) The component (C) is contacted with the component (S) and then with the component (A) to form a solid catalyst component (K1). Separately, the component (C) is contacted with the component (S) and then with the component (B) to form a solid catalyst component (K2). These catalyst components are used in polymerization.

xii) The component (A) is contacted with the component (C) and then with the component (S) to form a solid catalyst component (K1). Separately, the component (B) is contacted with the component (C) and then with the component (S) to form a solid catalyst component (K2). These catalyst components are used in polymerization.

xiii) The component (C) is contacted with the component (S) and then with a contact product between the component (A) and the component (C) to form a solid catalyst component (K1). Separately, the component (C) is contacted with the component (S) and then with a contact product between the component (B) and the component (C) to form a solid catalyst component (K2). These catalyst components are used in polymerization.

xiv) The component (C) is contacted with the component (S), then with the component (A) and thereafter again with the component (C) to form a solid catalyst component (K1). Separately, the component (C) is contacted with the component (S), then with the component (B) and thereafter again with the component (C) to form a solid catalyst component (K2). These catalyst components are used in polymerization.

Of these, the contact sequences xi) and xiii) are particularly preferred.

In a third embodiment, the olefin polymerization catalysts (K3) of the invention may be prepared by contacting the component (A), the component (B), the component (C) and the solid carrier (S) in an inert hydrocarbon.

The components may be brought into contact in any order, but are preferably contacted in exemplary orders as described below.

xv) The component (S) is mixed and contacted with the component (C). The contact mixture is brought into contact with the component (A) and then with the component (B).

xvi) The component (S) is mixed and contacted with the component (C). The contact mixture is brought into contact with the component (B) and then with the component (A).

xvii) The component (S) is mixed and contacted with the component (C). The contact mixture is brought into contact with a contact mixture of the components (A) and (B).

xviii) The component (A) is mixed and contacted with the component (B). The contact mixture is brought into contact with the component (C) and then with the component (S).

xix) The component (S) is contacted with the component (C). The contact product is brought into contact with the component (C), then with the component (A) and the component (B).

xx) The component (S) is contacted with the component (C). The contact product is brought into contact with the component (C), then with the component (B) and the component (A).

xxi) The component (S) is contacted with the component (C). The contact product is brought into contact with the component (C) and then with a contact mixture of the components (A) and (B).

xxii) The component (S) is mixed and contacted with the component (C). The contact mixture is brought into contact with a contact mixture of the components (A), (B) and (C).

xxiii) The component (S) is mixed and contacted with the component (C). The contact mixture is brought into contact with a contact mixture of the components (A) and (C) and then with the component (B).

xxiv) The component (S) is mixed and contacted with the component (C). The contact mixture is brought into contact with a contact mixture of the components (B) and (C) and then with the component (A).

xxv) The component (S) is contacted with the component (C). The contact product is brought into contact with the component (C), then with a contact mixture of the components (A) and (C) and with a contact mixture of the components (B) and (C).

xxvi) The component (S) is contacted with the component (C). The contact product is brought into contact with the component (C), then with a contact mixture of the components (B) and (C) and with a contact mixture of the components (A) and (C).

xxvii) The component (S) is contacted with the component (C). The contact product is brought into contact with the component (C) and with a contact mixture of the components (A), (B) and (C).

xxviii) A mixture of the components (A) and (C) and a mixture of the components (B) and (C) are mixed together. The mixture is then brought into contact with a contact product of the components (S) and (C).

xxix) A mixture of the components (A) and (C) and a mixture of the components (B) and (C) are mixed together. The mixture is then brought into contact with a contact product obtained by contacting the component (S) and the component (C) and contacting the resultant contact product with the component (C).

When a plurality of the components (C) are used, the components (C) may be the same or different from one another. Of these contact sequences, the sequences xv), xvi), xvii), xxii), xxiii) and xxiv) are preferable, and the sequences xvii) and xxii) are more preferable.

In the exemplary contact sequences described above, the step (P1) which includes contacting the components (S) and (C), the step (P2) which includes contacting the components (S) and (A), the step (P3) which includes contacting the components (S) and (B), and the step which includes contacting the components (S), (A) and (B) may be performed in the presence of at least one component (G) selected from polyalkylene oxide blocks (g-1), higher aliphatic amides (g-2), polyalkylene oxides (g-3), polyalkylene oxide alkyl ethers (g-4), alkyl diethanol amines (g-5) and polyoxyalkylene alkylamines (g-6). The presence of the components (G) inhibits the fouling during the polymerization and improves particle properties of the obtainable polymers. Of the components (G), (g-1), (g-2), (g-3) and (g-4) are preferable, and (g-1) and (g-2) are particularly preferable.

The solvents used in the preparation of the solid catalyst components include inert hydrocarbon solvents, and in detail aliphatic hydrocarbons such as propane, butane, pentane, hexane, heptane, octane, decane, dodecane and kerosine; alicyclic hydrocarbons such as cyclopentane, cyclohexane and methylcyclopentane; aromatic hydrocarbons such as benzene, toluene and xylene; halogenated hydrocarbons such as ethylene chloride, chlorobenzene and dichloromethane; and mixtures of these hydrocarbons.

When the component (C) and the component (S) are brought into contact together, the reaction site in the component (C) and the reaction site in the component (S) react with each other to form a chemical bond, resulting in a contact product between the component (C) and the component (S). The time of contact of the component (C) and the component (S) is usually in the range of 0 to 20 hours, and preferably 0 to 10 hours. The contact temperature is usually in the range of −50 to 200° C., and preferably −20 to 120° C. If the initial contact between the components (C) and (S) takes place precipitously, the reaction heat or reaction energy breaks the component (S) to cause a deteriorated morphology of the obtainable solid catalyst component. The use of such component in polymerization will result in difficult continuous operation due to bad morphology of the polymer. Thus, the initial contact of the components (C) and (S) is preferably performed at a low temperature of −20 to 30° C. to avoid the generation of reaction heat. In another preferred embodiment, the reaction is carried out at a rate which permits maintaining the initial contact temperature while controlling the reaction heat. These preferred embodiments also apply to cases where the components (C) and (S) are contacted together and the contact product is then contacted with the component (C). The molar ratio in contacting the components (C) and (S), (component (C)/component (S)), may be selected appropriately. The higher the molar ratio, the larger the amounts of the components (A) and (B) that can be contacted with the contact product, resulting in improved activity of the solid catalyst component.

The molar ratio of the component (C) to the component (S) [=molar amount of component (C)/molar amount of component (S)] is preferably in the range of 0.2 to 2.0, and particularly preferably 0.4 to 2.0.

The contact of the contact product of the components (C) and (S) with the component (A) and the component (B) is usually carried out for 0 to 5 hours, preferably 0 to 2 hours, and at −50 to 200° C., preferably −50 to 100° C. The contact amounts of the components (A) and (B) are greatly dependent on the kind and amount of the component (C). In the case of the component (c-1), the components are used in amounts such that the molar ratio [(c-1)/M] of the component (c-1) to all the transition metal atoms (M) in the component (A) and the component (B) is generally in the range of 0.01 to 100,000, and preferably 0.05 to 50,000. In the case of the component (c-2), the components are used in amounts such that the molar ratio [(c-2)/M] of the aluminum atoms in the component (c-2) to all the transition metal atoms (M) in the component (A) and the component (B) is generally in the range of 10 to 500,000, and preferably 20 to 100,000. In the case of the component (c-3), the components are used in amounts such that the molar ratio [(c-3)/M] of the component (c-3) to all the transition metal atoms (M) in the component (A) and the component (B) is generally in the range of 1 to 10, and preferably 1 to 5. The ratio of the component (C) to all the transition metal atoms (M) in the component (A) and the component (B) may be determined by inductively coupled plasma (ICP) optical emission spectrometry.

The quantitative ratio of the component (A) and the component (B) may be determined appropriately depending on the desired molecular weight and molecular weight distribution of the polyolefin. In a preferred embodiment, the ratio of a polymer afforded by the component (A) and a polymer by the component (B) [=amount of polymer afforded by component (A)/amount of polymer afforded by component (B)] is in the range of 40/60 to 95/5, preferably 50/50 to 95/5, and particularly preferably 60/40 to 95/5. Herein, it is preferable that the amount of polymers afforded by the component (A) is larger, because the component (A) gives macromonomers and a larger amount of such macromonomers is more advantageous in the formation of long-chain branches. The molar ratio of the components (A) and (B) in terms of the transition metal compound is not limited as long as the above ratio of polymer amounts is satisfied. The ratio may be selected appropriately depending on the ratio of activities exhibited by each of the solid catalyst components obtained by bringing the contact product of the components (S) and (C) into contact with the component (A) or the component (B). The proportions of polymers afforded by the components (A) and (B) may be determined based on the peak separation as will be described later.

Olefin Polymerization Processes Using Olefin Polymerization Catalysts (a) or Olefin Polymerization Catalysts (b)

The solid catalyst components as described hereinabove may be used directly to catalyze (co) polymerization of olefins. Alternatively, an olefin may be prepolymerized with the solid catalyst component to give a prepolymerized solid catalyst component.

The prepolymerized solid catalyst component may be prepared by prepolymerizing an olefin in the presence of the solid catalyst component, usually in an inert hydrocarbon solvent. The prepolymerization may be performed by any processes such as batch processes, semicontinuous processes or continuous processes, under any pressure conditions such as reduced pressure, normal pressure or increased pressure. In a preferred embodiment of the prepolymerization, the prepolymerized solid catalyst component is formed in an amount of 0.01 to 1000 g, preferably 0.1 to 800 g, and more preferably 0.2 to 500 g per 1 g of the solid catalyst component.

In an embodiment, the prepolymerized solid catalyst component formed in the inert hydrocarbon solvent may be separated from the suspension and resuspended in an inert hydrocarbon solvent, and an olefin may be fed to the suspension obtained or may be fed after the suspension is dried.

The prepolymerization temperature may be in the range of −20 to 80° C., preferably 0 to 60° C., and the prepolymerization time may range from about 0.5 to 100 hours, preferably about 1 to 50 hours. The olefin used in the prepolymerization is similar to an olefin to be used in the polymerization as will be described later. Preferably, the olefin used in the prepolymerization is an olefin based on ethylene.

The solid catalyst components described hereinabove may be used in the prepolymerization without limitation. Where necessary, the component (C) may be used, and in particular an organoaluminum compound (c-1) represented by Formula (11) may be preferably used. When the component (C) is used, the molar ratio of the aluminum atoms (Al—C) in the component (C) to the transition metal compound, (component (C)/transition metal compound), may be in the range of 0.1 to 10,000, and preferably 0.5 to 5,000.

The concentration of the solid catalyst components in the prepolymerization system, namely, the solid catalyst components/liter of polymerization volume, is usually in the range of 1 to 1000 g/L, and desirably 10 to 500 g/L. The prepolymerization may be carried out in the presence of the component (G) to inhibit fouling or to improve particle properties.

The component (G) may be generally mixed and contacted with the solid catalyst components at a temperature similar to the prepolymerization temperature. The amount thereof based on 100 parts by weight of the solid catalyst components is in the range of 0.1 to 20 parts by weight, preferably 0.3 to 10 parts by weight, and more preferably 0.4 to 5 parts by weight.

In order to improve flowability of the prepolymerized catalyst components or to inhibit the occurrence of heat spot, sheeting or polymer bulk during the polymerization, the prepolymerized catalyst components produced by the prepolymerization may be contacted with the component (G). In this case, the component (G) is preferably (g-1), (g-2), (g-3) or (g-4), and is particularly preferably (g-1) or (g-2).

The above mixing/contact with the component (G) is usually carried out at −50 to 50° C., preferably −20 to 50° C., and for 1 to 1000 minutes, preferably 5 to 600 minutes.

When the solid catalyst components are mixed and contacted with the component (G), the component (G) is used in an amount of 0.1 to 20 parts by weight, preferably 0.3 to 10 parts by weight, and more preferably 0.4 to 5 parts by weight based on 100 parts by weight of the solid catalyst components.

The solid catalyst components and the component (G) may be mixed and contacted together in an inert hydrocarbon solvent. Examples of the inert hydrocarbon solvents are as described hereinabove.

The prepolymerized catalyst components may be dried to afford dried prepolymerized catalyst components, which may be used as an olefin polymerization catalyst in the invention. The prepolymerized catalyst component is usually dried after the prepolymerized catalyst component is separated from the hydrocarbon dispersion medium by, for example, filtering the suspension.

The prepolymerized catalyst components may be dried under a stream of an inert gas at a temperature of not more than 70° C., and preferably in the range of 20 to 50° C. The dried prepolymerized catalyst component preferably has a volatile component content of not more than 2.0 wt o, and preferably not more than 1.0 wt %. A lower volatile component content in the dried prepolymerized catalyst component is more preferable. The lower limit thereof is not particularly limited, but is practically 0.001 wt %. The drying time depends on the drying temperature or the like, but is usually in the range of 3 to 8 hours.

If the volatile component content in the dried prepolymerized catalyst component exceeds 2.0 wt %, the dried prepolymerized catalyst component shows lower flowability and may not be supplied stably to a polymerization reactor. The angle of repose of the dried prepolymerized catalyst component is not more than 50°, preferably in the range of 5 to 47°, and more preferably 10 to 45°. If the angle of repose of the dried prepolymerized catalyst component is in excess of 50°, the flowability of the dried prepolymerized catalyst component is low and the component may not be supplied stably to a polymerization reactor.

The volatile component content in the dried prepolymerized catalyst component may be determined by a weight loss method or gas chromatography.

In a weight loss method, the dried prepolymerized catalyst component is heated at 110° C. for 1 hour in an inert gas atmosphere and the resultant weight loss is obtained in percentage relative to the weight of the dried prepolymerized catalyst component before the heating.

In a gas chromatography method, volatile components such as hydrocarbons are extracted from the dried prepolymerized catalyst component, a calibration curve is drawn according to an internal standard method, and the volatile component content is determined in wt % from the GC area.

In the determination of the volatile component content of the dried prepolymerized catalyst component, a weight loss method is adopted when the volatile component content in the dried prepolymerized catalyst component is approximately 1 wt % or more, and a gas chromatography method is adopted when the volatile component content in the dried prepolymerized catalyst component is approximately 1 wt % or less.

Examples of the inert gases used for the drying of the prepolymerized catalyst components include nitrogen gas, argon gas and neon gas. In the inert gases, it is desirable that the oxygen concentration is not more than 20 ppm, preferably not more than 10 ppm, more preferably not more than 5 ppm, and the water content is not more than 20 ppm, preferably not more than 10 ppm, more preferably not more than 5 ppm. If the oxygen concentration and the water content in the inert gas exceed the above ranges, the olefin polymerization activity of the dried prepolymerized catalyst components may be greatly deteriorated.

The dried prepolymerized catalyst components for olefin polymerization according to the invention have excellent flowability and can be stably supplied to a polymerization reactor. Since the solvent used to suspend the catalyst component has been removed and is not allowed in a gas phase polymerization system, the polymerization may be performed stably.

Next, processes for producing the ethylene polymers according to the present invention will be described. The ethylene polymers of the invention are obtained by polymerizing or copolymerizing olefins in the presence of the olefin polymerization catalyst described hereinabove. The ethylene polymers in the invention contain ethylene at not less than 10 mol % in the polymer.

In the invention, the polymerization may be carried out by any of liquid phase polymerization processes such as solution polymerization and suspension polymerization, and gas phase polymerization processes. The polymerization catalyzed by the olefin polymerization catalyst of the first embodiment of the invention is preferably performed by a solution polymerization process. The polymerization in the presence of the solid catalyst components according to the second or third embodiment of the invention is preferably carried out by a suspension polymerization process or a gas phase polymerization process.

The liquid phase polymerization process may use an inert hydrocarbon solvent. Examples thereof include aliphatic hydrocarbons such as propane, butane, pentane, hexane, heptane, octane, decane, dodecane and kerosine; alicyclic hydrocarbons such as cyclopentane, cyclohexane and methylcyclopentane; aromatic hydrocarbons such as benzene, toluene and xylene; halogenated hydrocarbons such as ethylene chloride, chlorobenzene and dichloromethane; and mixtures of these hydrocarbons. The olefin itself may be used as a solvent.

In the polymerization of olefins with the olefin polymerization catalyst, the component (A) and the component (B) are each used in an amount of 10-12 to 10-1 mol, and preferably 10-8 to 10-2 mol per liter of the reaction volume. As the component (C), an organoaluminum compound (c-1) represented by Formula (11) may be particularly preferably used.

In the polymerization of olefins using the solid catalyst components, the polymerization temperature is usually in the range of −50 to +200° C., preferably 0 to 170° C., particularly preferably 60 to 170° C., and the polymerization pressure is generally in the range of atmospheric pressure to 100 kg/cm², preferably atmospheric pressure to 50 kg/cm². The polymerization may be carried out batchwise, semi-continuously or continuously. It is also possible to carry out the polymerization in two or more stages under differing reaction conditions.

The molecular weight of the obtainable ethylene polymer may be controlled by the presence of hydrogen in the polymerization system or by changing the polymerization temperature. In the polymerization, the component (G) may be used to inhibit fouling or to improve particle properties.

For the polymerization, one or more olefin monomers are selected from ethylene and C3-20 olefins. In a preferred embodiment, at least one of the monomers is ethylene or propylene. In a particularly preferred embodiment of the olefin polymerization, ethylene is homopolymerized or ethylene and a C3-20 olefin are copolymerized. Examples of the C3-20 olefins include α-olefins such as propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene; and cyclic olefins such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene. Examples further include styrene, vinylcyclohexane, diene, acrylic acid, methacrylic acid, fumaric acid, maleic anhydride; and polar monomers such as methyl acrylate, ethyl acrylate, methyl methacrylate, ethyl methacrylate and methacrylic acid.

In general, olefin polymerization catalysts increase activity for ethylene polymers as the molecular weight of ethylene polymers is lower or the proportion of terminal double bonds is higher, thereby affording a large number of long-chain branches. The component (A) in the invention can afford polymers having a relatively low molecular weight and a large number of terminal double bonds. Such polymers are effectively combined together by the component (B) to give polymers having a larger number of long-chain branches compared to conventional polymers. Further, the polymerization activity of the component (A) provides high productivity in the production of the polymers having a larger number of long-chain branches.

General Characteristics of Polymers (Macromonomers) Afforded by Olefin Polymerization Catalysts (a)

Polymers (macromonomers) afforded by the olefin polymerization catalysts (a) of the invention have unsaturated bond sites such as vinyl groups at molecular terminals, and have a number average molecular weight (Mn) by GPC in the range of 5,000 to 20,000, preferably 5,000 to 15,000, and more preferably 5,000 to 14,000.

The number of terminal vinyl bonds in the polymers (macromonomers) may be determined by known methods such as $^1$H-NMR, $^{13}$C-NMR and FT-IR. In the invention, $^1$H-NMR or FT-IR is used.

The terminal vinyl percentage (%) is calculated from:

terminal vinyl percentage (%)=α/14000×Mn×100

(wherein α is a number of vinyl terminals per 1000 methylene carbons in the polymer main chain, Mn is a number average molecular weight, and Mw is a weight average molecular weight). When the terminal vinyl percentage is 20%, α×Mn=2800. When polymers having a terminal vinyl percentage of less than 20% are used as macromonomers to form long-chain branches, they do not substantially undergo polymerization and remain unreacted, resulting in polymers with a small number of long-chain branches and unsatisfactory shaping processability. The polymers obtained according to the invention have α×Mn in the range of 2,800 to 14,000, preferably 4,000 to 14,000, and more preferably 5,000 to 14,000. The ratio of the weight average molecular weight (Mw) to the number average molecular weight (Mn), (Mw/Mn), is in the range of 1.0 to 3.5, preferably 1.5 to 3.5, and more preferably 1.5 to 3. Macromonomers satisfying these conditions have a high proportion of terminal unsaturated bonds and a lower molecular weight compared to known products. Thus, they can be copolymerized at a high rate, and excellent melt flow properties and shaping processability are obtained.

Because of the large number of terminal vinyl bonds, the macromonomers obtained according to the invention may be easily modified by grafting or the like. In detail, the macromonomers may be modified by an oxidation reaction, a grafting reaction or an ene-synthesis reaction to functionalized olefin polymers or olefin polymer polar resin composite materials (for example, antistatic agents, cosmetic additives, toner release agents, pigment dispersants, vinyl chloride resin lubricants, paints, adhesives).

General Characteristics of Ethylene Polymers Afforded by Olefin Polymerization Catalysts (b)

In general, olefin polymerization catalysts increase activity for ethylene polymers (macromonomers) as the molecular weight of the ethylene polymers (macromonomers) is lower or the proportion of terminal double bonds is higher, thereby affording a large number of long-chain branches. The component (A) in the invention can afford polymers having a relatively low molecular weight and a large number of terminal double bonds. Such polymers are effectively combined together by the component (B) to give polymers having a larger number of long-chain branches compared to conventional polymers. Further, the polymerization activity of the component (A) provides high productivity in the production of the polymers having a larger number of long-chain branches.

Ethylene polymers produced by polymerizing ethylene or copolymerizing ethylene and a C3-20 olefin in the presence of the olefin polymerization catalyst (b) have the following characteristics.

Characteristics

Two or more peaks are observed in gel permeation chromatography (GPC), and Log ($M_{Max}$) at the peak top of the maximum peak is in the range of 3.8≤Log ($M_{Max}$)≤4.6, and preferably 4.0≤Log ($M_{Max}$)≤4.4. The peak intensity ($H_{Max}$) of the maximum peak and the peak intensity ($H_{second}$) of the second maximum peak have the relation: $H_{Max}≥2×H_{second}$.

Gel permeation chromatography (GPC) is performed with use of gel permeation chromatograph Alliance GPC 2000 (high temperature size exclusion chromatograph) manufactured by Waters, and a molecular weight distribution curve is recorded. The gel permeation chromatography conditions are as follows.

[Chromatograph and Conditions]

Chromatograph: Gel permeation chromatograph Alliance GPC 2000 (Waters)

Analysis software: Chromatography data system Empower (Waters)

Columns: Two TSK gel $GMH_6$-HT columns+two TSK gel $GMH_6$-HTL columns (each 7.5 mm in inner diameter and 30 cm in length, manufactured by TOSOH CORPORATION)

Mobile phase: o-dichlorobenzene (=ODCB) (special grade reagent manufactured by Wako Pure Chemical Industries, Ltd.)

Detector: differential refractometer (built in the chromatograph)

Column temperature: 140° C.

Flow rate: 1.0 mL/min

Injection amount: 500 µL

Sampling time intervals: 1 sec

Sample concentration: 0.15% (w/v)

Molecular weight calibration: monodisperse polystyrenes (manufactured by TOSOH CORPORATION)/ranging in molecular weight from 495 to 20,600,000

The molecular weight distribution and the average molecular weights are calculated in terms of polyethylene in accordance with a general calibration procedure described in J. Polym. Sci., B5, 753, Z. Crubisic, P. Rempp, H. Benoit (1967).

In the invention, the maximum peak in GPC is defined to be (i) a point on a GPC curve at which the local maximum value is reached, or (ii) a point on a GPC curve which gives the local maximum or local minimum value in secondary differentiation of the GPC curve. In the case where peaks overlap one another and are consequently observed to be a single peak or to have shoulders, the maximum peak may be effectively determined based on the local maximum and the local minimum values in secondary differentiation.

When the peak intensities of the peaks determined by the above method are assigned the letter H, and the peak intensity of the maximum peak and that of the second maximum peak are assigned the code $H_{Max}$ and $H_{second}$, respectively, these peak intensities satisfy the relation: $H_{Max} \geq 2 \times H_{second}$.

In the ethylene polymers according to the invention, the maximum peak which gives Log ($M_{Max}$) at the peak top and $H_{Max}$ is usually assigned to polymers catalyzed by the component (A), and the peak giving $H_{second}$ is frequently assigned to polymers by the component (B) or is a third peak as will be described later.

The polymers afforded by the component (A) show a relatively small molecular weight on a GPC chart and have terminal double bonds to behave as part of monomers (macromonomers) that are polymerized, forming long-chain branches. In detail, it is more advantageous for the formation of long-chain branches that the polymers afforded by the component (A) represent a large proportion of the polymers produced in the polymerization.

Although lower molecular weights of the polymers afforded by the component (A) are more advantageous for the formation of long-chain branches, an excessively small molecular weight results in lowered mechanical strength of shaped articles such as films or causes operation failure due to the attachment of the polymers to polymerizer walls. If the molecular weight is large, such polymers are not incorporated as macromonomers to make the formation of long-chain branches difficult. Thus, the molecular weight is desirably in an appropriate range.

The polymers obtained herein substantially provide three peaks. The first peak is assigned to the polymers afforded by the component (A) (also referred to as the component (A) peak), the second peak is derived from the polymers afforded by the component (B) (also referred to as the component (B) peak), and the third peak is observed when both the components (A) and (B) are used (hereinafter, also the third peak). The ratio of these peaks may be precisely determined by separating the peaks by a method as described below.

In the case where the peaks overlap one another and are consequently observed to be a single peak or to have shoulders, the peaks may be separated by a method described below and the ratio of the component (A) peak, the component (B) peak and the third peak may be determined precisely.

Peaks in a molecular weight curve (G1) of an ethylene polymer produced by the polymerization process according to the invention were separated by the following method using a molecular weight curve (G2) of an ethylene polymer that was catalyzed by a particulate catalyst composed of the component (A), the component (C) and the component (S) (the polymer may be also referred to as the polymer afforded by the component (A) alone) and a molecular weight curve (G3) of an ethylene polymer that was catalyzed by a particulate catalyst composed of the component (B), the component (C) and the component (S) (the polymer may be also referred to as the polymer afforded by the component (B) alone) wherein the polymerization conditions were identical to those in the production of the ethylene polymer of the present invention. Herein, the molecular weight curves were obtained by GPC measurement as described above, and the calculation for peak separation was conducted using Excel® 97 manufactured by Microsoft Corporation.

[1] With respect to the numerical data of the molecular weight curves (G1), (G2) and (G3), Log (molecular weight) was obtained at intervals of 0.02, and the intensity [dwt/d(log molecular weight)] was normalized such that the area of the molecular weight curve was 1.

[2] A synthetic curve (G4) was prepared from the curves (G2) and (G3).

[3] The intensities at the molecular weights in (G2) and (G3) were modified appropriately by a constant fraction such that the absolute value of the difference between the intensities at the molecular weights in (G1) and (G4) was not more than 0.0004. On a high molecular weight side, the intensity in (G1) and the intensity in (G4) differed by more than 0.0004 in absolute value due to the influence of the third peak. In view of this, the intensities in (G2) and (G3) were modified such that the absolute value of the difference between the intensities in (G1) and (G4) was not more than 0.0004 on a lower molecular weight side.

[4] A region which was found on a higher molecular weight side than the peak top and in which the curves (G1) and (G4) did not overlap each other, namely (G5) [(G1)-(G4)], was defined as the third peak. The weight fraction $W_a$ of the polymers afforded by the component (A), the weight fraction $W_b$ of the polymers afforded by the component (B) and the weight fraction $W_3$ of the third peak are calculated as follows.

$$W_a = S(G2)/S(G1)$$

$$W_b = S(G3)/S(G1)$$

$$W_3 = S(G5)/S(G1)$$

Here, S (G2) and S (G3) represent peak areas in (G2) and (G3) after the modification of the intensities, and S (G4) and S (G5) are peak areas in (G4) and (G5).

The weight fractions $W_a$, $W_b$ and $W_3$ may be determined appropriately depending on the desired molecular weights and molecular weight distribution of the target polyolefins. In a preferred embodiment, $40\% < W_a \leq 95\%$, $5\% < W_b \leq 60\%$ and 2%≤W≤30%. In a particularly preferred embodiment, 60%<$W_a$≤95%, 5%<$W_b$≤40% and 2%≤$W_3$≤20%. A higher proportion of the polymers afforded by the component (A) is preferable because a larger amount of the macromonomers afforded by the component (A) is more advantageous for the formation of long-chain branches.

Described next are the ethylene polymers (i to iv) that are obtained by homopolymerization or copolymerization of ethylene in the presence of the olefin polymerization catalyst (b). In the following description, properties are measured by the following methods.

[Identification of Compounds]

Compounds obtained in synthetic examples are identified by 270 MHz $^1$H-NMR (GSH-270 manufactured by JEOL Ltd.), FD-mass spectrometry (FD-MS) (SX-102A manufactured by JEOL Ltd.) and gas chromatography-mass spectrometry (GC-MS) (GCMS-QP5050A manufactured by Shimadzu Corporation).

[Quantitative Analysis of Terminal Structures]

The terminal structures (the number of double bonds) of the polymers are determined by $^1$H-NMR (ECA-500 manufactured by JEOL Ltd.).

[Melt Flow Rate (MFR)]

The melt flow rate (MFR) is determined in accordance with ASTM D 1238-89 at 190° C. under 2.16 kg load.

[Density (d)]

To determine the density (d), a measurement sample is heat treated at 120° C. for 1 hour, then gradually cooled to room temperature linearly in 1 hour, and analyzed by a density gradient tube method.

[Melt Tension (MT)]

The melt tension (MT) at 190° C. is measured by the following method. The melt tension (MT) of a polymer is determined by measuring the stress under stretching at a fixed speed. The measurement is performed with a MT tester manufactured by Toyo Seiki Seisaku-Sho, Ltd., under the conditions in which the resin temperature is 190° C., the melting time is 6 minutes, the barrel diameter is 9.55 mm, the extrusion rate is 15 mm/min, the take-up speed is 24 m/min (in the event of breakage of the molten filament, the take-up speed is lowered by 5 m/min), the nozzle diameter is 2.095 mm and the nozzle length is 8 mm. [Shear viscosity ($\eta^*$) at 200° C. and angular velocity of 1.0 rad/sec]

The shear viscosity ($\eta^*$) at 200° C. and angular velocity of 1.0 rad/sec is measured by the following method. In detail, the shear viscosity ($\eta^*$) is determined by measuring the distribution of shear viscosity ($\eta^*$) at 200° C. at an angular velocity [ω(rad/sec)] in the range of 0.02512≤ω≤100. Dynamic Stress Rheometer SR-5000 available from Rheometrics Scientific, Inc. is used. Parallel plates having a diameter of 25 mm are used as a sample holder. The sample thickness is approximately 2.0 mm. The measurement is conducted on 5 points per single digit of ω. The amount of strain is selected appropriately in the range of 3 to 10% while the torque in the measurement is detectable and over-torquing is not caused. The sample used in the shear viscosity measurement is prepared by pressing a measurement sample to a thickness of 2 mm with use of a press machine manufactured by SHINTO Metal Industries Corporation with a preheating temperature of 190° C., a preheating time of 5 minutes, a heating temperature of 190° C., a heating time of 2 minutes, a heating pressure of 100 kg G/cm$^2$, a cooling temperature of 20° C., a cooling time of 5 minutes and a cooling pressure of 100 kg/cm$^2$.

[Total of Methyl Branches and Ethyl Branches (A+B)]

The number of methyl branches and ethyl branches is determined by $^{13}$C-NMR as follows. ECP 500 nuclear magnetic resonance apparatus ($^1$H: 500 MHz) manufactured by JEOL Ltd. is used. The number of scans is 10,000 to 30,000. The chemical shift used is a peak of main chain methylene (29.97 ppm). A PE sample weighing 250-400 mg and 3 ml of a liquid mixture consisting of special grade o-dichlorobenzene (Wako Pure Chemical Industries, Ltd.):benzene-d6 (ISOTEC) (=5:1 by volume) are added to a commercially available NMR quartz glass tube having a diameter of 10 mm. The mixture is heated at 120° C. to give a uniform dispersion, which is analyzed. The absorptions in the NMR spectrum are assigned in accordance with Kagaku no Ryouiki Zoukan (Region of chemistry, extra edition) No. 141, NMR—Sousetsu to Jikken Gaido (Review and Experimental Guide) [I], pp. 132-133. The number of methyl branches per 1000 carbon atoms is calculated from the integrated intensity ratio of the absorption intensity (19.9 ppm) assigned to the methyl groups of the methyl branches relative to the integrated total of the absorption intensities at 5-45 ppm. The number of ethyl branches is calculated from the integrated intensity ratio of the absorption intensity (10.8 ppm) assigned to the ethyl groups of the ethyl branches relative to the integrated total of the absorption intensities at 5-45 ppm.

[Zero-Shear Viscosity ($\eta_0$)]

The zero-shear viscosity [$\eta_0$ (P)] at 200° C. is measured by the following method. In detail, the zero-shear viscosity [$\eta_0$ (P)] is determined by measuring the distribution of shear viscosity ($\eta^*$) at 200° C. at an angular velocity [ω(rad/sec)] in the range of 0.02512≤ω≤100. The measurement is performed as described hereinabove using Dynamic Stress Rheometer SR-5000 available from Rheometrics Scientific, Inc.

The zero-shear viscosity $\eta_0$ calculated by fitting the Carreau model of Equation (Eq-5) below to the rheology curve (distribution of shear viscosity ($\eta^*$) by angular velocity (ω)) according to a nonlinear least squares method.

$$\eta^* = \eta_0 [1 + (\lambda\omega)^a]^{(n-1)/a} \quad \text{(Eq-5)}$$

In the equation above, λ represents a parameter having a time dimension, and n indicates a power index of the material. The fitting by a nonlinear least squares method is made such that d represented by Equation (Eq-6) below becomes minimum.

$$d = \sum_{\omega=0.02512}^{100} [\text{Log}_{10}\eta_{exp}(\omega) - \text{Log}_{10}\eta_{calc}(\omega)]^2 \quad \text{(Eq-6)}$$

In the equation above, $\eta_{exp}(\omega)$ is the measured shear viscosity and $\eta_{calc}(\omega)$ is the shear viscosity calculated from the Carreau model.

[Weight Average Molecular Weight (Mw) by GPC-VISCO]

The weight average molecular weight (Mw) by GPC-viscometry (GPC-VISCO) is determined using GPC/V2000 from Waters as described below. Shodex AT-G is used as a guard column, and two AT-806 columns are used as analytical columns. The column temperature is 145° C. The mobile phase is o-dichlorobenzene containing 0.3 wt % of BHT as antioxidant and is pumped at a rate of 1.0 ml/min. The sample concentration is 0.1 wt %. The detector is a differential refractometer. Three capillary viscometers are used. Polystyrenes manufactured by TOSOH CORPORATION are used as standards. The measured viscosity is calculated with the viscometers and the refractometer, and the weight average molecular weight (Mw) is calculated by universal calibration of the measured viscosity.

[Molecular Weight at Maximum Weight Fraction (Peak Top M), Number Average Molecular Weight (Mn), Z-Average Molecular Weight (Mz), Ratio of Weight Average Molecular Weight to Number Average Molecular Weight (Mw/Mn), and Ratio of Z-Average Molecular Weight to Weight Average Molecular Weight (Mz/Mw)]

To calculate the molecular weight at maximum weight fraction (peak top M), number average molecular weight (Mn), Z-average molecular weight (Mz), ratio of weight average molecular weight to number average molecular weight (Mw/Mn), and ratio of Z-average molecular weight to weight average molecular weight (Mz/Mw), a molecular weight distribution curve is obtained under the following conditions with use of gel permeation chromatograph Alliance GPC 2000 (high temperature size exclusion chromatograph) manufactured by Waters.

[Apparatus and Conditions]

Analysis software: chromatography data system Empower (Waters)

Columns: two TSK gel $GMH_6$-HT columns+two TSK gel $GMH_6$-HTL columns (each 7.5 mm in inner diameter and 30 cm in length, manufactured by TOSOH CORPORATION)

Mobile phase: o-dichlorobenzene (special grade reagent manufactured by Wako Pure Chemical Industries, Ltd.)

Detector: differential refractometer (built in the chromatograph)

Column temperature: 140° C.

Flow rate: 1.0 mL/min

Injection amount: 500 µL

Sampling time intervals: 1 sec

Sample concentration: 0.15% (w/v)

Molecular weight calibration: monodisperse polystyrenes (manufactured by TOSOH CORPORATION)/ranging in molecular weight from 495 to 20,600,000

A molecular weight distribution curve in terms of polyethylene is prepared in accordance with a general calibration procedure described in J. Polym. Sci., B5, 753, Z. Crubisic, P. Rempp, H. Benoit (1967). The molecular weight at maximum weight fraction, number average molecular weight (Mn), Z-average molecular weight (Mz), ratio of weight average molecular weight to number average molecular weight (Mw/Mn), and ratio of Z-average molecular weight to weight average molecular weight (Mz/Mw) are calculated from the molecular weight distribution curve.

[$M_{Me+Et}/M_{all}$]

The ratio $M_{Me+Et}/M_{all}$ is determined by $^{13}$C-NMR as follows. The measurement is performed using ECP 500 nuclear magnetic resonance apparatus ($^1$H: 500 MHz) manufactured by JEOL Ltd., in a manner as described hereinabove. The absorptions in the NMR spectrum are assigned in accordance with Kagaku no Ryouiki Zoukan (Region of chemistry, extra edition) No. 141, NMR—Sousetsu to Jikken Gaido (Review and Experimental Guide) [I], pp. 132-133.

The contents of the respective branches may be calculated based on the integrated intensity ratio of the absorption intensities appearing in the following regions: methyl branches: 19.9 ppm, ethyl branches: 10.8 ppm, propyl branches: 14.4 ppm, butyl branches: 23.1 ppm, isobutyl groups: 25.7 ppm, hexyl and higher branches: 31.9 ppm.

[Intrinsic Viscosity ([η])]

The intrinsic viscosity [[η] (dl/g)] is measured in a decalin solvent as follows. Approximately 20 mg of the ethylene copolymer is dissolved in 15 ml of decalin, and the specific viscosity $η_{sp}$ is measured in an oil bath at 135° C. After the decalin solution is diluted by addition of 5 ml of decalin, the specific viscosity $η_{sp}$ is measured again. The dilution is repeated two more times. By extrapolating the concentration (C) to 0, the value $η_{sp}/C$ is obtained as the intrinsic viscosity.

$$[η]=\lim(η_{sp}/C)(C \to 0)$$

[Neck-In]

The ethylene copolymer is laminated by extrusion on a 50 g/m² craft paper as a substrate with use of a laminator manufactured by Sumitomo Heavy Industries, Ltd. which has a 65 mm diameter extruder and a T-die with a die width of 500 mm, under the following conditions.

Air gap: 130 mm

Actual resin temperature after die: 295° C.

Take-up speeds: 50 m/min, 80 m/min, 120 m/min, 200 m/min

Film thickness: 20 µm at take-up speed of 80 m/min, 13 µm at take-up speed of 120 m/min, 8 µm at take-up speed of 200 m/min The neck-in is calculated from $L_0$–L wherein $L_0$ is the width of the T-die and L is the width of a film laminated on the craft paper at each take-up speed.

[Film Breakage Speed and Take-Off Speed at which Surging Occurs]

The ethylene copolymer is laminated by extrusion on a 50 g/m² craft paper as a substrate with use of a laminator manufactured by SUMITOMO Heavy Industries, Ltd. which has a 65 mm diameter extruder and a T-die with a die width of 500 mm, under the conditions wherein the air gap is 130 mm and the actual resin temperature after die is 295° C. The output is determined such that the film thickness at a take-up speed of 80 m/min is 20 µm.

The take-up speed is increased, and the speed that causes breakage of the molten film (the molten film is regarded to be broken even when only an edge thereof is cut) is determined as the film breakage speed.

Separately, the take-up speed is increased and the neck-in is measured five times at each take-up speed. The results of the five measurements are averaged. The take-up speed at which two or more of the five measurements result in an average neck-in value±1.5 mm or more is determined as the take-off speed at which surging occurs.

[Resin Pressure]

The ethylene copolymer is laminated by extrusion on a 50 g/m² craft paper as a substrate with use of a laminator manufactured by Sumitomo Heavy Industries, Ltd. which has a 65 mm diameter extruder and a T-die with a die width of 500 mm, under the conditions wherein the air gap is 130 mm, the actual resin temperature after die is 295° C., the take-up speed is 80 m/min and the film thickness is 20 µm. The resin pressure at the crosshead is measured during the extrusion.

[Heat Seal Strength]

The ethylene copolymer is laminated by extrusion on a substrate with use of a laminator manufactured by Sumitomo Heavy Industries, Ltd. which has a 65 mm diameter extruder and a T-die with a die width of 500 mm, under the conditions wherein the air gap is 130 mm, the actual resin temperature after die is 295° C., the take-up speed is 80 m/min and the film thickness is 25 µm. The substrate herein is a multilayer structure prepared by applying a urethane anchor coating agent on a surface of a 15 µm thick biaxially stretched nylon film (EMBLEM ONM manufactured by UNITIKA. LTD.) and thereafter extruding thereon an ethylene mixture resin in a thickness of 25 µm wherein the ethylene mixture resin is a blend of 50 parts by weight each of a Ziegler-catalyzed linear low-density polyethylene and a Ziegler-catalyzed high-pressure low-density polyethylene. The ethylene copolymer is laminated by extrusion on the ethylene mixture resin layer of the multilayer structure.

The heat seal strength between the ethylene copolymer layers in the laminate film obtained by extrusion is measured and evaluated under the following conditions.

A one-side hot bar sealer is used.
Heat seal pressure: 2 kg/cm$^2$
Heat seal time: 0.5 sec
Seal bar width: 10 mm
Test piece width: 15 mm
Peel angle: 180°
Peel rate: 300 mm/min Ethylene Polymers (i)

The ethylene homopolymers or copolymers according to the invention are homopolymers of ethylene or copolymers of ethylene and C4-10 α-olefins, preferably copolymers of ethylene and C4-10 α-olefins (when 1-butene is used as a comonomer, an α-olefin of 6 to 10 carbon atoms is always used together), and more preferably copolymers of ethylene and C6-10 α-olefins. The C4-10 α-olefins copolymerized with ethylene include 1-butene, 1-hexene, 4-methyl-1-pentene, 1-octene and 1-decene.

The ethylene polymers (i) of the invention satisfy the following requirements [1] to [5] at the same time. The requirements [1] to [5] will be described in detail below.

Requirement [1]

The melt flow rate (MFR) of the ethylene polymers (i) as measured at 190° C. under a load of 2.16 kg is in the range of 0.1 to 100 g/10 min, preferably 1.0 to 50 g/10 min, and more preferably 4.0 to 30. With MFR being 0.1 g/10 min or above, the ethylene polymers show a shear viscosity which is not excessively high and permits excellent processability, and the polymers can give shaped articles such as films having excellent appearance. With MFR being not more than 100 g/10 min, the ethylene polymers show good tensile strength or heat seal strength.

In general, MFR is heavily dependent on the molecular weight. In detail, the smaller the MFR, the higher the molecular weight, and the larger the MFR, the lower the molecular weight. The molecular weight of ethylene polymers (i) is known to be determined by the composition ratio of hydrogen and ethylene (hydrogen/ethylene) present in the polymerization system in the production of the ethylene polymers (for example, Kazuo Soga, KODANSHA "CATALYTIC OLEFIN POLYMERIZATION", p. 376 (1990)). The ethylene polymers (i) that have MFR ranging from the lower limit to the upper limit as described in claims of the invention may be produced by increasing or decreasing the hydrogen/ethylene ratio.

Requirement [2]

The ethylene polymers (i) have a density (d) in the range of 875 to 970 kg/m$^3$, preferably 885 to 964 kg/m$^3$, and more preferably 905 to 960 kg/m$^3$.

When the density (d) is 875 kg/m$^3$ or above, the ethylene polymers can give films having low surface tackiness. When the density (d) is not more than 970 kg/m$^3$, the ethylene polymers show good low-temperature sealing properties.

In general, the density is dependent on the α-olefin content in the ethylene polymers. The lower the α-olefin content, the higher the density, and the higher the α-olefin content, the lower the density. The α-olefin content in ethylene polymers is known to be determined by the composition ratio of α-olefins and ethylene (α-olefins/ethylene) present in the polymerization system (for example, Walter Kaminsky, Makromol. Chem. 193, p. 606 (1992)). Accordingly, the density of the ethylene polymers (i) can be controlled by increasing or decreasing the α-olefin/ethylene ratio in the production of the ethylene polymers. By this controlling, the ethylene polymers (i) that have a density ranging from the lower limit to the upper limit as described in claims of the invention may be produced.

Requirement [3]

In the ethylene polymers (i), the ratio [MT/η*(g/P)] is in the range of $1.50 \times 10^{-4}$ to $9.00 \times 10^{-4}$, preferably $2.00 \times 10^{-4}$ to $7.00 \times 10^{-4}$, and more preferably $2.60 \times 10^{-4}$ to $5.00 \times 10^{-4}$ wherein [MT (g)] is the melt tension at 190° C. and [η*(P)] is the shear viscosity at 200° C. and an angular velocity of 1.0 rad/sec. With MT/η* being not less than $1.50 \times 10^{-4}$ the ethylene polymers have acceptable neck-in.

Requirement [4]

The ethylene polymers (i) have a total of methyl branches [A(/1000 C)] and ethyl branches [B(/1000 C)], [(A+B)(/1000 C)], of not more than 1.8, preferably not more than 1.3, more preferably not more than 0.8, and particularly preferably not more than 0.5 according to $^{13}$C-NMR. The numbers of methyl branches and ethyl branches in the invention are defined to be per 1000 carbon atoms as will be described later.

If the ethylene polymers have short-chain branches such as methyl branches and ethyl branches, the short-chain branches are incorporated in the crystal and the crystal plane spacings are enlarged, resulting in lowered mechanical strength of the polymers (for example, KOUBUNSHI NO JUMYOU YOSOKU TO CHOUJUMYOUKA GIJUTSU (LIFETIME PREDICTION OF POLYMERS AND LIFETIME EXTENDING TECHNOLOGY), Zenjiro Osawa, et al., p. 481, NTS (2002)). Good mechanical strength of the ethylene polymers is ensured when the total number of methyl branches and ethyl branches (A+B) is not more than 1.8.

The number of methyl branches and ethyl branches in the ethylene polymers is greatly dependent on how the ethylene polymers constituting the ethylene polymers are produced. Ethylene polymers obtained by high-pressure radical polymerization have a larger number of methyl branches and ethyl branches than ethylene polymers obtained by Ziegler-catalyzed coordination polymerization. In the case of coordination polymerization, the number of methyl branches and ethyl branches in the ethylene polymers is greatly dependent on the composition ratios among propylene, 1-butene and ethylene (propylene/ethylene, 1-butene/ethylene) in the polymerization system. Accordingly, the ethylene polymers that have a total number of methyl branches and ethyl branches (A+B) as described in claims of the invention may be produced by increasing or decreasing the 1-butene/ethylene ratio.

Requirement [5]

In the ethylene polymers (i) of the invention, the zero-shear viscosity at 200° C. [η$_0$ (P)] and the weight average molecular weight (Mw) measured by GPC-viscometry (GPC-VISCO) satisfy Equation (Eq-1) below:

$$0.01 \times 10^{13} \times Mw^{3.4} \leq \eta_0 \leq 4.5 \times 10^{-13} \times MW^{3.4} \quad \text{(Eq-1)},$$

preferably satisfy Equation (Eq-2) below:

$$0.05 \times 10^{-13} \times Mw^{3.4} \leq \eta_0 \leq 4.5 \times 10^{-13} \times MW^{3.4} \quad \text{(Eq-2)},$$

more preferably satisfy Equation (Eq-3) below:

$$0.10 \times 10^{-13} \times Mw^{3.4} \leq \eta_0 \leq 3.5 \times 10^{-13} \times Mw^{3.4} \quad \text{(Eq-3)},$$

and particularly preferably satisfy Equation (Eq-4) below:

$$0.15 \times 10^{-13} \times Mw^{3.4} \leq \eta_0 \leq 1.8 \times 10^{-13} \times Mw^{3.4} \quad \text{(Eq-4)}.$$

According to literature (C. Gabriel, H. Munstedt, J. Rheol., 47(3), 619 (2003)), when the zero-shear viscosity [η$_0$ (P)] is double-logarithmically plotted against the weight average molecular weight (Mw), the sloe of the plot is in accordance with the 3.4 power law for polymers such as long-chain branch-free, linear ethylene polymers in which elongation viscosity does not show strain hardening characteristics, but the zero-shear viscosity [η$_0$ (P)] is lower than the power law for polymers such as high-pressure low-density polyethylenes in which elongation viscosity shows strain rate hardening characteristics. When the zero-shear viscosity [$\eta_0$ (P)] at 200° C. is not more than $4.5\times10^{-13}\times Mw^{3.4}$, the elongation viscosity of the ethylene polymers shows strain rate hardening characteristics and consequently the ethylene polymers do not cause take-up surge.

The ethylene polymers (i) that satisfy the requirements [1] to [5] described above provide advantageous effects as will be described later, in most of the plastic industry applications. However, in order to reliably prevent accidental or sudden problems in processability or flowability, the ethylene polymers preferably satisfy the requirement [6] below in addition to the requirements [1] to [5].

Requirement [6]

In the ethylene polymers (i), the intrinsic viscosity ([$\eta$] (dl/g)) measured at 135° C. in decalin and the weight average molecular weight (Mw) measured by GPC-viscometry (GPC-VISCO) satisfy Equation (Eq-7) below:

$$0.80\times10^{-4}\times Mw_{0.776} \leq [\eta] \leq 1.65\times10^{-4}\times Mw_{0.776} \quad \text{(Eq-7)},$$

preferably satisfy Equation (Eq-8) below:

$$0.90\times10^{-4}\times Mw^{0.776} \leq [\eta] \leq 1.55\times10^{-4}\times Mw^{0.776} \quad \text{(Eq-8)},$$

and more preferably satisfy Equation (Eq-9) below:

$$0.90\times10^{-4}\times Mw^{0.776} \leq [\eta] \leq 1.40\times10^{-4}\times Mw^{0.776} \quad \text{(Eq-9)}.$$

As known in the art (for example, Walther Burchard, ADVANCES IN POLYMER SCIENCE, 143, Branched Polymer II, p. 137 (1999)), ethylene polymers having long-chain branches show a smaller intrinsic viscosity [$\eta$] (dl/g) in relation to the molecular weight as compared to linear ethylene polymers having no long-chain branches. The ethylene polymers (i) of the invention have a large number of long-chain branches and exhibit excellent processability and flowability particularly when the intrinsic viscosity [$\eta$] (dl/g) is not more than $1.65\times10^{-4}\times MW^{0.776}$ Ethylene Polymers (ii)

The ethylene homopolymers or copolymers according to the invention are homopolymers of ethylene or copolymers of ethylene and C4-10 $\alpha$-olefins, preferably copolymers of ethylene and C4-10 $\alpha$-olefins (when 1-butene is used as a comonomer, an $\alpha$-olefin of 6 to 10 carbon atoms is always used together), and more preferably copolymers of ethylene and C6-10 $\alpha$-olefins. The C4-10 $\alpha$-olefins copolymerized with ethylene include 1-butene, 1-hexene, 4-methyl-1-pentene, 1-octene and 1-decene.

The ethylene polymers of the invention have the following properties (I) to (VI).

(I) The melt flow rate (MFR) is in the range of 0.1 to 100 g/10 min, preferably 1.0 to 50 g/10 min, and more preferably 4 to 30 g/10 min. With the melt flow rate (MFR) being 0.1 g/10 min or above, the ethylene polymers show a shear viscosity which is not excessively high and permits excellent processability. With the melt flow rate (MFR) being not more than 100 g/10 min, the ethylene polymers show good tensile strength or heat seal strength.

The melt flow rate (MFR) is heavily dependent on the molecular weight. In detail, the smaller the melt flow rate (MFR), the higher the molecular weight, and the larger the melt flow rate (MFR), the lower the molecular weight. The molecular weight of ethylene polymers is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The melt flow rate (MFR) of the ethylene polymers may be controlled by increasing or decreasing the hydrogen/ethylene ratio.

(II) The density (d) is in the range of 875 to 970 kg/m$^3$, preferably 885 to 964 kg/m$^3$, and more preferably 903 to 935 kg/m$^3$. When the density (d) is 875 kg/m$^3$ or above, the ethylene polymers can give films having low surface tackiness. When the density (d) is not more than 970 kg/m$^3$, the ethylene polymers show good low-temperature sealing properties.

The density is dependent on the $\alpha$-olefin content in the ethylene polymers. The lower the $\alpha$-olefin content, the higher the density, and the higher the $\alpha$-olefin content, the lower the density. The $\alpha$-olefin content in ethylene polymers is known to be determined by the composition ratio of $\alpha$-olefins and ethylene ($\alpha$-olefins/ethylene) present in the polymerization system (for example, Walter Kaminsky, Makromol. Chem. 193, p. 606 (1992)). Accordingly, the ethylene polymers that have a density in the aforementioned range may be produced by increasing or decreasing the $\alpha$-olefin/ethylene ratio.

(III) The ratio [MT/$\eta$*(g/Poise)] is in the range of $2.50\times10^{-4}$ to $9.00\times10^{-4}$, preferably $2.50\times10^{-4}$ to $7.00\times10^{-4}$, and more preferably $3.00\times10^{-4}$ to $5.00\times10^{-4}$, wherein [MT (g)] is the melt tension at 190° C. and [$\eta$*(Poise)] is the shear viscosity at 200° C. and an angular velocity of 1.0 rad/sec. With MT/$\eta$* being not less than $2.50\times10^{-4}$, the ethylene polymers have acceptable neck-in.

(IV) The total of methyl branches [A(/1000 C)] and ethyl branches [B(/1000 C)], [(A+B)(/1000 C)], according to $^{13}$C-NMR is not more than 1.8, preferably not more than 1.3, more preferably not more than 0.8, and still more preferably not more than 0.5. The numbers of methyl branches and ethyl branches in the invention are defined to be per 1000 carbon atoms as will be described later.

If the ethylene polymers have short-chain branches such as methyl branches and ethyl branches, the short-chain branches are incorporated in the crystal and the crystal plane spacings are enlarged, resulting in lowered mechanical strength of the resins (for example, KOUBUNSHI NO JUMYOU YOSOKU TO CHOUJUMYOUKA GIJUTSU (LIFETIME PREDICTION OF POLYMERS AND LIFETIME EXTENDING TECHNOLOGY), edited by Zenjiro Osawa, et al., NTS, 2002, p. 481). Good mechanical strength of the ethylene polymers is ensured when the total number of methyl branches and ethyl branches (A+B) is not more than 1.8.

The number of methyl branches and ethyl branches in the ethylene polymers is greatly dependent on how the ethylene polymers are produced. Ethylene polymers obtained by high-pressure radical polymerization have a larger number of methyl branches and ethyl branches than ethylene polymers obtained by Ziegler-catalyzed coordination polymerization. In the case of coordination polymerization, the number of methyl branches and ethyl branches in the ethylene polymers is greatly dependent on the composition ratios among propylene, 1-butene and ethylene (propylene/ethylene, 1-butene/ethylene) in the polymerization system. Accordingly, the total number of methyl branches and ethyl branches (A+B) in the ethylene polymers may be controlled by increasing or decreasing the 1-butene/ethylene ratio.

(V) The zero-shear viscosity at 200° C. [$\eta_0$ (P)] and the weight average molecular weight (Mw) measured by GPC-viscometry (GPC-VISCO) satisfy Equation (Eq-1) below:

$$0.01\times10^{-13}\times Mw^{3.4} \leq \eta_0 \leq 4.50\times10^{-13}\times Mw^{3.4} \quad \text{(Eq-1)}$$

preferably satisfy Equation (Eq-2) below:

$$0.05\times10^{-13}\times Mw^{3.4} \leq \eta_0 \leq 4.50\times10^{-13}\times Mw^{3.4} \quad \text{(Eq-2)}$$

more preferably satisfy Equation (Eq-3) below:

$$0.10\times10^{-13}\times Mw^{3.4} \leq \eta_0 \leq 3.50\times10^{-13}\times Mw^{3.4} \quad \text{(Eq-3)}$$

and particularly preferably satisfy Equation (Eq-4) below:

$$0.15\times10^{-13}\times Mw^{3.4} \leq \eta_0 \leq 1.80\times10^{-13}\times Mw^{3.4} \quad \text{(Eq-4)}$$

According to literature (C. Gabriel, H. Munstedt, J. Rheol., 47(3), 619 (2003)), when the zero-shear viscosity [$\eta_0$ (P)] is double-logarithmically plotted against the weight average molecular weight (Mw), the zero-shear viscosity is in accordance with the 3.4 power law for resins such as long-chain branch-free, linear ethylene polymers in which elongation viscosity does not show strain hardening characteristics, but the zero-shear viscosity [$\eta_0$ (P)] is lower than the power law for resins such as high-pressure low-density polyethylenes in which elongation viscosity shows strain rate hardening characteristics. When the zero-shear viscosity [$\eta_0$ (P)] at 200° C. is not more than $4.50\times10^{-13}\times Mw^{3.4}$, the elongation viscosity of the ethylene polymers shows strain rate hardening characteristics and consequently the ethylene polymers do not cause take-up surge.

That the ethylene polymers satisfy Equation (Eq-1) above is synonymous with that log ($\eta_0$) and log(Mw) that are obtained by double-logarithmically plotting $\eta_0$ and Mw of the ethylene polymers meet Equation (Eq-1') described below:

$$3.4\log(Mw)-15.0000 \leq \log(\eta_0) \leq 3.4\log(Mw)-12.3468 \qquad \text{(Eq-1')}$$

(VI) The molecular weight at the maximum weight fraction (peak top M) in a molecular weight distribution curve obtained by GPC is in the range of $1.0\times10^{4.30}$ to $1.0\times10^{4.50}$, and preferably $1.0\times10^{4.30}$ to $1.0\times10^{4.40}$.

The mechanical strength of ethylene polymers is greatly affected by low molecular weight components. The presence of low molecular weight components increases molecular terminals that are considered to be an origin of breakage, leading to lowered mechanical strength ("Polyethylene Gijutsu Dokuhon (Polyethylene Technology Reader)", edited by Kazuo Matsuura and Naotaka Mikami, Kogyo Chosakai Publishing, Inc., 2001, p. 45). When the molecular weight at the maximum weight fraction (peak top M) in a molecular weight distribution curve obtained by GPC is not less than $1.0\times10^{4.30}$, the ethylene polymers contain a small amount of low molecular weight components adversely affecting mechanical strength and thus achieve excellent mechanical strength.

The molecular weight at the maximum weight fraction in a molecular weight distribution curve obtained by GPC is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The molecular weight at the maximum weight fraction in a molecular weight distribution curve may be controlled by increasing or decreasing the hydrogen/ethylene ratio.

Ethylene Polymers (iii)

The ethylene copolymers according to the invention are copolymers of ethylene and C4-10 α-olefins, preferably copolymers of ethylene and C4-10 α-olefins (when butene-1 is used as a comonomer, an α-olefin of 6 to 10 carbon atoms is always used together), and more preferably copolymers of ethylene and C6-10 α-olefins. The C4-10 α-olefins copolymerized with ethylene include 1-butene, 1-hexene, 4-methyl-1-pentene, 1-octene and 1-decene.

The ethylene copolymers of the invention have the following properties (I) to (VI).

(I) The melt flow rate (MFR) is in the range of 0.1 to 100 g/10 min, preferably 1.0 to 50 g/10 min, and more preferably 4 to 30 g/10 min.

With the melt flow rate (MFR) being 0.1 g/10 min or above, the ethylene copolymers show a shear viscosity which is not excessively high and permits excellent processability. With the melt flow rate (MFR) being not more than 100 g/10 min, the ethylene copolymers show good tensile strength or heat seal strength.

The melt flow rate (MFR) is heavily dependent on the molecular weight. In detail, the smaller the melt flow rate (MFR), the higher the molecular weight, and the larger the melt flow rate (MFR), the lower the molecular weight. The molecular weight of ethylene copolymers is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The melt flow rate (MFR) of the ethylene copolymers may be controlled by increasing or decreasing the hydrogen/ethylene ratio.

(II) The density (d) is in the range of 875 to 936 kg/m$^3$, preferably 885 to 930 kg/m$^3$, and more preferably 903 to 930 kg/m$^3$. When the density (d) is 875 kg/m$^3$ or above, the ethylene copolymers can give films having low surface tackiness. When the density (d) is not more than 936 kg/m$^3$, the ethylene copolymers show good mechanical strength such as heat seal strength and pack breakage strength.

The density is dependent on the α-olefin content in the ethylene copolymers. The lower the α-olefin content, the higher the density, and the higher the α-olefin content, the lower the density. The α-olefin content in ethylene copolymers is known to be determined by the composition ratio of α-olefins and ethylene (α-olefins/ethylene) present in the polymerization system (for example, Walter Kaminsky, Makromol. Chem. 193, p. 606 (1992)). Accordingly, the ethylene copolymers that have a density in the aforementioned range may be produced by increasing or decreasing the α-olefin/ethylene ratio.

(III) The ratio [MT/$\eta$*(g/Poise)] is in the range of $2.50\times10^{-4}$ to $9.00\times10^{-4}$, preferably $2.50\times10^{-4}$ to $7.00\times10^{-4}$, and more preferably $3.00\times10^{-4}$ to $5.00\times10^{-4}$ wherein [MT (g)] is the melt tension and [$\eta$*(Poise)] is the shear viscosity at 200° C. and an angular velocity of 1.0 rad/sec.

With MT/$\eta$* being not less than $2.50\times10^{-4}$, the ethylene copolymers have acceptable neck-in.

(IV) The total of methyl branches [A(/1000 C)] and ethyl branches [B(/1000 C)], [(A+B)(/1000 C)], according to $^{13}$C-NMR is not more than 1.8, preferably not more than 1.3, more preferably not more than 0.8, and still more preferably not more than 0.5. The numbers of methyl branches and ethyl branches in the invention are defined to be per 1000 carbon atoms as will be described later.

If the ethylene copolymers have short-chain branches such as methyl branches and ethyl branches, the short-chain branches are incorporated in the crystal and the crystal plane spacings are enlarged, resulting in lowered mechanical strength of the resins (for example, KOUBUNSHI NO JUMYOU YOSOKU TO CHOUJUMYOUKA GIJUTSU (LIFETIME PREDICTION OF POLYMERS AND LIFETIME EXTENDING TECHNOLOGY), edited by Zenjiro Osawa, et al., NTS, 2002, p. 481). Good mechanical strength of the ethylene copolymers is ensured when the total number of methyl branches and ethyl branches (A+B) is not more than 1.8.

The number of methyl branches and ethyl branches in the ethylene copolymers is greatly dependent on how the ethylene copolymers are produced. Ethylene copolymers obtained by high-pressure radical polymerization have a larger number of methyl branches and ethyl branches than ethylene copolymers obtained by Ziegler-catalyzed coordination polymerization. In the case of coordination polymerization, the number of methyl branches and ethyl branches in the ethylene copolymers is greatly dependent on the composition ratios among propylene, 1-butene and ethylene (propylene/ethylene, 1-butene/ethylene) in the polymerization system. Accordingly, the total number of methyl branches and ethyl branches (A+B) in the ethylene copolymers may be controlled by increasing or decreasing the 1-butene/ethylene ratio.

(V) The zero-shear viscosity at 200° C. [$\eta_0$ (P)] and the weight average molecular weight (Mw) measured by GPC-viscometry (GPC-VISCO) satisfy Equation (Eq-1) below:

$$0.01 \times 10^{-13} \times Mw^{3.4} \leq \eta_0 \leq 4.50 \times 10^{-13} \times Mw^{3.4} \quad \text{(Eq-1)}$$

preferably satisfy Equation (Eq-2) below:

$$0.05 \times 10^{-13} \times Mw^{3.4} \leq \eta_0 \leq 4.50 \times 10^{-13} \times Mw^{3.4} \quad \text{(Eq-2)}$$

more preferably satisfy Equation (Eq-3) below:

$$0.10 \times 10^{-13} \times Mw^{3.4} \leq \eta_0 \leq 3.50 \times 10^{-13} \times Mw^{3.4} \quad \text{(Eq-3)}$$

and particularly preferably satisfy Equation (Eq-4) below:

$$0.15 \times 10^{-13} \times Mw^{3.4} \leq \eta_0 \leq 1.80 \times 10^{-13} \times Mw^{3.4} \quad \text{(Eq-4)}$$

According to literature (C. Gabriel, H. Munstedt, J. Rheol., 47(3), 619 (2003)), when the zero-shear viscosity [$\eta_0$ (P)] is double-logarithmically plotted against the weight average molecular weight (Mw), the zero-shear viscosity is in accordance with the 3.4 power law for resins such as long-chain branch-free, linear ethylene copolymers in which elongation viscosity does not show strain hardening characteristics, but the zero-shear viscosity [$\eta_0$ (P)] is lower than the power law for resins such as high-pressure low-density polyethylenes in which elongation viscosity shows strain rate hardening characteristics. When the zero-shear viscosity [$\eta_0$ (P)] at 200° C. is not more than $4.50 \times 10^{-13} \times Mw^{3.4}$, the elongation viscosity of the ethylene copolymers shows strain rate hardening characteristics and consequently the ethylene copolymers do not cause take-up surge.

That the ethylene copolymers satisfy Equation (Eq-1) above is synonymous with that log ($\eta_0$) and log(Mw) that are obtained by double-logarithmically plotting $\eta_0$ and Mw of the ethylene copolymers meet Equation (Eq-1') described below:

$$3.4 \log(Mw) - 15.0000 \leq \log(\eta_0) \leq 3.4 \log(Mw) - 12.3468 \quad \text{(Eq-1')}$$

(VI) The molecular weight at the maximum weight fraction (peak top M) in a molecular weight distribution curve obtained by GPC is in the range of $1.0 \times 10^{4.20}$ to $1.0 \times 10^{4.50}$, preferably $1.0 \times 10^{4.20}$ to $1.0 \times 10^{4.40}$, and more preferably $1.0 \times 10^{4.30}$ to $1.0 \times 10^{4.40}$.

The mechanical strength of ethylene copolymers is greatly affected by low molecular weight components. The presence of low molecular weight components increases molecular terminals that are considered to be an origin of breakage, leading to lowered mechanical strength ("Polyethylene Gijutsu Dokuhon (Polyethylene Technology Reader)", edited by Kazuo Matsuura and Naotaka Mikami, Kogyo Chosakai Publishing, Inc., 2001, p. 45). When the molecular weight at the maximum weight fraction (peak top M) in a molecular weight distribution curve obtained by GPC is not less than $1.0 \times 10^{4.20}$, the ethylene copolymers contain a small amount of low molecular weight components adversely affecting mechanical strength and thus achieve excellent mechanical strength.

The molecular weight at the maximum weight fraction (peak top M) in a molecular weight distribution curve obtained by GPC is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The molecular weight at the maximum weight fraction (peak top M) in a molecular weight distribution curve may be controlled by increasing or decreasing the hydrogen/ethylene ratio.

Ethylene Polymers (iv)

The ethylene homopolymers or copolymers according to the invention are homopolymers of ethylene or copolymers of ethylene and C3-10 α-olefins, preferably copolymers of ethylene and C4-8 α-olefins, and more preferably copolymers of ethylene and C4-6 α-olefins. The C3-10 α-olefins copolymerized with ethylene include propylene, 1-butene, 1-hexene, 4-methyl-1-pentene, 1-octene and 1-decene.

The ethylene polymers of the invention have the following properties (I) to (V).

(I) The ratio [$M_{Me+Et}/M_{all}$] is in the range of 0.30 to 1.00, preferably 0.50 to 1.00, and more preferably 0.70 to 1.00 wherein $M_{Me+Et}$ is the content (mol o) of methyl branches and ethyl branches according to $^{13}$C-NMR and $M_{all}$ is the content (mol %) of all the branches according to $^{13}$C-NMR. With $M_{Me+Et}/M_{all}$ being 0.30 or above, the ethylene polymers have an appropriately weak heat seal strength and thus have easy-opening properties.

Branch structures in the ethylene polymers are mostly formed by the copolymerization of ethylene with α-olefins. Methyl branches result from copolymerization with propylene as an α-olefin, ethyl branches from copolymerization with 1-butene, butyl branches from copolymerization with 1-hexene, isobutyl branches from copolymerization with 4-methyl-1-pentene, hexyl branches from copolymerization with 1-octene, and octyl branches from copolymerization with 1-decene.

The branch structures in the ethylene polymers may be quantitatively determined by $^{13}$C-NMR as will be described later. However, because branch structures longer than hexyl branches cannot be separated and quantified individually by $^{13}$C-NMR, branch structures longer than hexyl branches are quantitatively determined as a total of such long branch structures. The $M_{Me+Et}/M_{all}$ is substantially determined by the composition ratio of C3-4 α-olefins and C3-10 α-olefins ($C_{3-4}/C_{3-10}$) present in the polymerization system. Accordingly, the ethylene polymers having $M_{Me+Et}/M_{all}$ in the above range may be obtained by increasing or decreasing the $C_{3-4}/C_{3-10}$ ratio.

(II) The melt flow rate (MFR) is in the range of 0.1 to 100 g/10 min, preferably 1.0 to 50 g/10 min, and more preferably 4 to 30 g/10 min. With the melt flow rate (MFR) being 0.1 g/10 min or above, the ethylene polymers show a shear viscosity which is not excessively high and permits excellent processability. With the melt flow rate (MFR) being not more than 100 g/10 min, the ethylene polymers show good tensile strength or heat seal strength.

The melt flow rate (MFR) is heavily dependent on the molecular weight. In detail, the smaller the melt flow rate (MFR), the higher the molecular weight, and the larger the melt flow rate (MFR), the lower the molecular weight. The molecular weight of ethylene polymers is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The melt flow rate (MFR) of the ethylene polymers may be controlled by increasing or decreasing the hydrogen/ethylene ratio.

(III) The density (d) of the ethylene homopolymers or copolymers of the invention is in the range of 875 to 970 kg/m³, preferably 885 to 945 kg/m³, and more preferably 900 to 936 kg/m³. When the density (d) is 875 kg/m³ or above, the ethylene polymers can give films having low surface tackiness. When the density (d) is not more than 970 kg/m³, the ethylene polymers show good low-temperature sealing properties.

The density is dependent on the α-olefin content in the ethylene polymers. The lower the α-olefin content, the higher the density, and the higher the α-olefin content, the lower the density. The α-olefin content in ethylene polymers is known to be determined by the composition ratio of α-olefins and ethylene (α-olefins/ethylene) present in the polymerization system (for example, Walter Kaminsky, Makromol. Chem. 193, p. 606 (1992)). Accordingly, the ethylene polymers that have a density in the aforementioned range may be produced by increasing or decreasing the α-olefin/ethylene ratio.

(IV) The ratio [MT/η*(g/Poise)] is in the range of $1.50 \times 10^{-4}$ to $9.00 \times 10^{-4}$, preferably $2.00 \times 10^{-4}$ to $7.00 \times 10^{-4}$, and more preferably $2.60 \times 10^{-4}$ to $5.00 \times 10^{-4}$, wherein [MT (g)] is the melt tension and [η*(Poise)] is the shear viscosity at 200° C. and an angular velocity of 1.0 rad/sec. With MT/η* being not less than $1.50 \times 10^{-4}$, the ethylene polymers have acceptable neck-in. With MT/η* being not more than $9.00 \times 10^{-4}$, the ethylene polymers show good extendability.

(V) The zero-shear viscosity at 200° C. [$\eta_0$ (P)] and the weight average molecular weight (Mw) measured by GPC-viscometry (GPC-VISCO) satisfy Equation (Eq-1) below:

$$0.01 \times 10^{-13} \times Mw^{3.4} \leq \eta_0 \leq 4.50 \times 10^{-13} \times Mw^{3.4} \quad \text{(Eq-1)}$$

preferably satisfy Equation (Eq-2) below:

$$0.05 \times 10^{-13} \times Mw^{3.4} \leq \eta_0 \leq 4.50 \times 10^{-13} \times Mw^{3.4} \quad \text{(Eq-2)}$$

more preferably satisfy Equation (Eq-3) below:

$$0.10 \times 10^{-13} \times Mw^{3.4} \leq \eta_0 \leq 3.50 \times 10^{-13} \times Mw^{3.4} \quad \text{(Eq-3)}$$

and particularly preferably satisfy Equation (Eq-4) below:

$$0.15 \times 10^{-13} \times Mw_{3.4} \leq \eta_0 \leq 1.80 \times 10^{-13} \times Mw^{3.4} \quad \text{(Eq-4)}$$

According to literature (C. Gabriel, H. Munstedt, J. Rheol., 47(3), 619 (2003)), when the zero-shear viscosity [$\eta_0$ (P)] is double-logarithmically plotted against the weight average molecular weight (Mw), the zero-shear viscosity is in accordance with the 3.4 power law for resins such as long-chain branch-free, linear ethylene polymers in which elongation viscosity does not show strain hardening characteristics, but the zero-shear viscosity [$\eta_0$ (P)] is lower than the power law for resins such as high-pressure low-density polyethylenes in which elongation viscosity shows strain rate hardening characteristics. When the zero-shear viscosity [$\eta_0$ (P)] at 200° C. is not more than $4.50 \times 10^{-13} \times Mw^{3.4}$, the elongation viscosity of the ethylene polymers shows strain rate hardening characteristics and consequently the ethylene polymers do not cause take-up surge.

That the ethylene polymers satisfy Equation (Eq-1) above is synonymous with that log ($\eta_0$) and log(Mw) that are obtained by double-logarithmically plotting $\eta_0$ and Mw of the ethylene polymers meet Equation (Eq-1') described below:

$$3.4 \log(Mw) - 15.0000 \leq \log(\eta_0) \leq 3.4 \log(Mw) - 12.3468 \quad \text{(Eq-1')}$$

In a preferred embodiment, the ethylene polymers of the invention further have the following property (VI).

(VI) The molecular weight at the maximum weight fraction (peak top M) in a molecular weight distribution curve obtained by GPC is in the range of $1.0 \times 10^{4.20}$ to $1.0 \times 10^{4.50}$.

The mechanical strength of ethylene polymers is greatly affected by low molecular weight components. The presence of low molecular weight components increases molecular terminals that are considered to be an origin of breakage, leading to lowered mechanical strength ("Polyethylene Gijutsu Dokuhon (Polyethylene Technology Reader)", edited by Kazuo Matsuura and Naotaka Mikami, Kogyo Chosakai Publishing, Inc., 2001, p. 45). When the molecular weight at the maximum weight fraction (peak top M) in a molecular weight distribution curve obtained by GPC is not less than $1.0 \times 10^{4.30}$, the ethylene polymers contain a small amount of low molecular weight components adversely affecting mechanical strength and thus achieve excellent mechanical strength.

The molecular weight at the maximum weight fraction in a molecular weight distribution curve obtained by GPC is known to be determined by the composition ratio of hydrogen and ethylene (hydrogen/ethylene) present in the polymerization system (for example, "CATALYTIC OLEFIN POLYMERIZATION", edited by Kazuo Soga, et al., KODANSHA SCIENTIFIC, 1990, p. 376). The molecular weight at the maximum weight fraction in a molecular weight distribution curve may be controlled by increasing or decreasing the hydrogen/ethylene ratio.

Treatment Methods and Applications of Ethylene Polymers

To reduce variations in properties, particles of the ethylene polymers obtained by the polymerization processes, and other optional components may be molten, kneaded together and pelletized by appropriate methods.

The ethylene polymers of the invention may be blended with other thermoplastic resins to give thermoplastic resin compositions that have excellent processability and high mechanical strength. The blending ratio of the ethylene polymer and other thermoplastic resins may be in the range of 99.9/0.1 to 0.1/99.9.

Examples of other thermoplastic resins include crystalline thermoplastic resins such as polyolefins, polyamides, polyesters and polyacetals; and amorphous thermoplastic resins such as polystyrenes, acrylonitrile/butadiene/styrene (ABS) copolymers, polycarbonates, polyphenylene oxides and polyacrylates. Polyvinyl chloride may also be preferably used.

The polyolefins include ethylene polymers, propylene polymers, butene polymers, 4-methyl-1-pentene polymers, 3-methyl-1-butene polymers and hexene polymers. In particular, ethylene polymers, propylene polymers and 4-methyl-1-pentene polymers are preferred. The ethylene polymers herein may be the ethylene polymers according to the invention or may be conventional ethylene polymers or ethylene/polar group-containing vinyl copolymers, and preferably conventional ethylene polymers.

The polyesters include aromatic polyesters such as polyethylene terephthalate, polyethylene naphthalate and polybutylene terephthalate; polycaprolactone and polyhydroxybutyrate.

The polyamides include aliphatic polyamides such as Nylon-6, Nylon-66, Nylon-10, Nylon-12 and Nylon-46, and aromatic polyamides produced from aromatic dicarboxylic acids and aliphatic diamines.

The polyacetals include polyformaldehyde (polyoxymethylene), polyacetaldehyde, polypropionaldehyde and polybutylaldehyde. Of these, polyformaldehyde is particularly preferred.

The polystyrenes include styrene homopolymers and binary copolymers of styrene with acrylonitrile, methyl methacrylate or α-methyl styrene.

The ABS copolymers preferably contain 20 to 35 mol % of structural units derived from acrylonitrile, 20 to 30 mol % of structural units derived from butadiene, and 40 to 60 mol % of structural units derived from styrene.

The polycarbonates include polymers obtained from bis(4-hydroxyphenyl)methane, 1,1-bis(4-hydroxyphenyl)ethane, 2,2-bis(4-hydroxyphenyl)propane and 2,2-bis(4-hydroxyphenyl)butane. In particular, polycarbonates obtained from 2,2-bis(4-hydroxyphenyl)propane are preferred.

Preferred examples of the polyphenylene oxides include poly(2,6-dimethyl-1,4-phenylene oxide).

Preferred examples of the polyacrylates include polymethyl methacrylate and polybutyl acrylate.

The thermoplastic resins may be used singly, or two or more kinds may be used in combination. Of the thermoplastic resins, the polyolefins are particularly preferable, and ethylene polymers are still more preferable.

The ethylene polymers may contain additives in addition to the above thermoplastic resins while still achieving the objects of the invention. Exemplary additives are weathering stabilizers, heat stabilizers, antistatic agents, anti-slip agents, anti-blocking agents, anti-fogging agents, lubricants, pigments, dyes, nucleating agents, plasticizers, anti-aging agents, hydrochloric acid absorbers and antioxidants.

The ethylene polymers of the invention, and the thermoplastic resin compositions containing the ethylene polymers may be processed with good processability into articles having excellent mechanical strength. Preferred shaped articles are films, and laminate films including the films are more preferred.

The ethylene polymers of the invention, and the thermoplastic resin compositions containing the ethylene polymers may be processed by usual film-forming processes, sheet-forming processes, blow molding processes, injection molding processes or extrusion processes. The film-forming processes include extrusion lamination, T-die extrusion and blown-film extrusion (air cooling, water cooling, multistage cooling, high-speed processing). The films thus obtained may be used individually or may be used as multilayer structures having various functions. Such multilayer structures may be produced by co-extrusion according to the shaping methods described above. Alternatively, the films may be laminated with paper or barrier films (such as aluminum foils, deposited films and coating films) that are not suited for co-extrusion, by laminating processes such as extrusion laminating processes or dry laminating processes. Multilayer structures having higher functions may be manufactured by co-extrusion according to blow molding processes, injection molding processes or extrusion processes similar to the co-extrusion according to film-forming processes.

The ethylene polymers of the invention, and the thermoplastic resin compositions containing the ethylene polymers may be shaped into articles such as films, sheets, blow-molded infusion bags, blow-molded bottles, gasoline tanks, extruded tubes or pipes, tear caps, injection molded articles including everyday goods, fibers, and large articles manufactured by rotational molding.

The ethylene polymers of the invention, and the thermoplastic resin compositions containing the ethylene polymers may be processed into films that are suitably used as water content packaging bags, liquid soup packages, liquid-packaging paper containers, laminate raw fabrics, special-shaped liquid package bags (such as standing pouches), standardized bags, heavy-duty bags, wrapping films, sugar bags, oil content packaging bags, various packaging films such as food packaging films, protective films, infusion solution bags and agricultural materials. The films may be laminated with bases such as nylon films, polyester films or polyolefin films for use as multilayer films.

EXAMPLES

The present invention will be described in detail hereinbelow based on examples without limiting the scope of the invention. Properties were measured in these examples by the methods as described in the description of the ethylene polymers (i) to (iv).

(1) Synthesis of Bridged Metallocene Compounds of Formula [1], and Olefin Polymerization Processes Using Olefin Polymerization Catalysts (a)

Synthetic Example 1

Synthesis of dimethylsilylene(cyclopentadienyl) (3-ethylcyclopentadienyl) zirconium dichloride (A1)

<Step 1> synthesis of chloro(cyclopentadienyl)dimethylsilane

THF in a volume of 100 ml was added to 14.3 g (110 mmol) of dimethylsilyl dichloride, and the mixture was cooled to −78° C. A 2 M THF solution of sodium cyclopentadiene in a volume of 38.7 ml (77.4 mmol) was added thereto dropwise over a period of 30 minutes, and the temperature was gradually increased. The mixture was stirred at room temperature for 24 hours, and was concentrated under reduced pressure. Insolubles were removed by filtration. The filtrate was washed with hexane, and the hexane was distilled away from the filtrate under reduced pressure, thereby obtaining chloro (cyclopentadienyl)dimethylsilane. The compound was used in the next step.

<Step 2> synthesis of (3-ethylcyclopentadienyl) (cyclopentadienyl)dimethylsilane Ethylcyclopentadiene in an amount of 7.52 g (80 mmol) was dissolved in 100 ml of THF, and the solution was cooled to −78° C. A 1.58 M hexane solution of n-butyllithium in a volume of 56 ml (92 mmol) was added thereto dropwise. The mixture was stirred at room temperature for 2 hours and was added dropwise to 50 ml of THF containing 110 mmol of the chloro(cyclopentadienyl)dimethylsilane at −78° C. The temperature was gradually increased, and the mixture was stirred at room temperature for 24 hours and was concentrated under reduced pressure. Insolubles were removed by filtration. The filtrate was washed with hexane and was distilled under reduced pressure. The distillate was subjected to silica gel column chromatography, and 0.86 g of (3-ethylcyclopentadienyl)(cyclopentadienyl)dimethylsilane was obtained. The compound was identified by GC-MS. GC-MS: 216 (MS).

<Step 3> synthesis of dimethylsilylene (cyclopentadienyl) (3-ethylcyclopentadienyl) zirconium dichloride (A1)

The dimethylsilyl(cyclopentadienyl) (3-ethylcyclopentadienyl) in an amount of 0.90 g (3.9 mmol) was dissolved in 40 ml of diethyl ether, and the solution was cooled to −78° C. A 1.57 M hexane solution of n-butyllithium in a volume of 5.09 ml (8.0 mmol) was added thereto dropwise. The temperature was gradually increased, and the mixture was stirred at room temperature for 24 hours and was concentrated under reduced pressure. The concentrate was washed with 13 ml of hexane three times. The resultant white solid was suspended in 50 ml of hexane. To the suspension, 820 mg (3.5 mmol) of zirconium tetrachloride was added at −78° C. The temperature was gradually increased, and the mixture was stirred at room temperature for 24 hours. The mixture was then filtered and washed with hexane to remove insolubles. The filtrate was concentrated under reduced pressure and was washed with pentane. The resultant solid was dried under reduced pressure to give 210 mg of dimethylsilylene(cyclopentadienyl) (3-ethylcyclopentadienyl)zirconium dichloride (A1) (yield: 14%). The compound was identified by $^1$H-NMR and FD-MS.

$^1$H-NMR (CDCl$_3$, based on TMS): 7.1-6.9 (m, 2H), 6.6 (s, 1H), 6.0-5.8 (m, 3H), 5.5 (s, 1H), 2.6 (m, 2H), 1.2 (t, 3H), 0.8-0.7 ppm (d, 6H); FD-MS: 376 (MS)

Synthetic Example 2

Synthesis of dimethylsilylene(3-n-propylcyclopentadienyl) (cyclopentadienyl)zirconium dichloride (A2)

<Step 1> synthesis of chloro(cyclopentadienyl)dimethylsilane

THF in a volume of 100 ml was added to 14.3 g (110 mmol) of dimethylsilyl dichloride, and the mixture was cooled to −78° C. A 2 M THF solution of sodium cyclopentadiene in a volume of 38.7 ml (77.4 mmol) was added thereto dropwise over a period of 30 minutes, and the temperature was gradually increased. The mixture was stirred at room temperature for 24 hours, and was concentrated under reduced pressure. Sodium chloride was removed by filtration. The filtrate was washed with hexane, and the hexane was distilled away from the filtrate under reduced pressure, thereby obtaining chloro(cyclopentadienyl)dimethylsilane. The compound was used in the next step.

<Step 2> synthesis of dimethylsilyl (3-n-propylcyclopentadienyl)(cyclopentadienyl)

THF in a volume of 100 ml was added to 2.16 g (20 mmol) of n-propylcyclopentadiene, and the mixture was cooled to −78° C. A 1.57 M hexane solution of n-butyllithium in a volume of 13.3 ml (22 mmol) was slowly added thereto dropwise. The mixture was stirred at room temperature for 3 hours. The reactor was cooled again to −78° C., and 3.97 g (25 mmol) of the chloro(cyclopentadienyl)dimethylsilane dissolved in 20 ml of THF was added dropwise to the reactor. The mixture was stirred at room temperature for 18 hours, and the completion of the reaction was confirmed by TLC. Water was added at 0° C. to terminate the reaction. The reaction liquid was extracted with hexane. The organic layer was washed with a saturated saline solution, was dried over magnesium sulfate, and was filtered. The filtrate was concentrated under reduced pressure. The concentrate was purified by silica gel column chromatography (solvent:hexane/triethylamine=98/2 (v/v)) and distillation under reduced pressure to give 1.73 g of dimethylsilyl (3-n-propylcyclopentadienyl) (cyclopentadienyl) (yield: 38%). The compound was identified by $^1$H-NMR and GC-MS.

$^1$H-NMR (CDCl$_3$, based on TMS): 7.0-6.0 (br, 7H), 3.0 (s, 1H), 2.9 (s, 1H), 2.3 (m, 2H), 1.6 (m, 2H) 0.9 (t, 3H), 0.1 (t, 3H), −0.2 ppm (s, 3H); GC-MS: 230 (MS)

<Step 3> synthesis of dimethylsilylene (3-n-propylcyclopentadienyl)(cyclopentadienyl)zirconium dichloride (A2)

The dimethylsilyl(3-n-propylcyclopentadienyl) (cyclopentadienyl) in an amount of 0.90 g (3.9 mmol) was dissolved in 40 ml of diethyl ether, and the solution was cooled to −78° C. A 1.57 M hexane solution of n-butyllithium in a volume of 5.09 ml (8.0 mmol) was added thereto dropwise. The temperature was gradually increased, and the mixture was stirred at room temperature for 24 hours and was concentrated under reduced pressure. The concentrate was washed with 13 ml of hexane three times. The resultant white solid was suspended in 50 ml of hexane. To the suspension, 820 mg (3.5 mmol) of zirconium tetrachloride was added at −78° C. The temperature was gradually increased, and the mixture was stirred at room temperature for 24 hours. The mixture was then filtered and washed with hexane to remove salts. The filtrate was concentrated under reduced pressure and was washed with pentane. The resultant solid was dried under reduced pressure to give 210 mg of dimethylsilylene(3-n-propylcyclopentadienyl) (cyclopentadienyl)zirconium dichloride (A2) (yield: 14%). The compound was identified by $^1$H-NMR and FD-MS.

$^1$H-NMR (CDCl$_3$, based on TMS): 7.1-6.9 (m, 2H), 6.6 (s, H), 6.0-5.8 (m, 3H), 5.5 (s, 1H), 2.6 (m, 2H), 1.5 (m, 2H), 0.9 (t, 3H), 0.8-0.7 ppm (d, 6H); FD-MS: 388 (MS)

Synthetic Example 3

Synthesis of dimethylsilylene(cyclopentadienyl) (3-n-butylcyclopentadienyl)zirconium dichloride (A3)

<Step 1> synthesis of (3-n-butylcyclopentadienyl)chlorodimethylsilane

THF in a volume of 50 ml was added to 30.1 g (61.5 mmol) of a 25 wt % THF solution of butylcyclopentadiene, and the mixture was cooled to 0° C. A 1.52 M hexane solution of n-butyllithium in a volume of 38.4 ml (58.4 mmol) was added thereto dropwise. The mixture was stirred at room temperature for 2 hours and was added dropwise to 50 ml of THF containing 14.3 g (110 mmol) of dimethylsilyl dichloride at −78° C. The temperature was gradually increased, and the mixture was stirred at room temperature for 24 hours and was concentrated under reduced pressure. Insolubles were removed by filtration. The filtrate was washed with hexane and was distilled under reduced pressure, thereby obtaining 8.09 g of (3-n-butylcyclopentadienyl)chlorodimethylsilane (yield: 64%). The compound was identified by GC-MS. GC-MS: 214 (MS).

<Step 2> synthesis of dimethylsilyl (3-n-butylcyclopentadienyl)(cyclopentadienyl)

THF in a volume of 50 ml was added to 8.8 ml (16.6 mmol) of a 2 M THF solution of sodium cyclopentadienide, and the mixture was cooled to −78° C. The (3-n-butylcyclopentadienyl)chlorodimethylsilane in an amount of 1.89 g (8.8 mmol) was dissolved in 20 ml of THF, and the solution was added dropwise to the reactor. The mixture was stirred at room temperature for 2 hours and at 50° C. for 2 hours. The completion of the reaction was confirmed by TLC, and water was added at 0° C. to terminate the reaction. The reaction liquid was extracted with hexane. The organic layer was washed with a saturated saline solution, was dried over magnesium sulfate, and was filtered. The filtrate was concentrated under reduced pressure. The concentrate was distilled under reduced pressure to give 1.07 g of dimethylsilyl (3-n-butylcyclopentadienyl)(cyclopentadienyl) (yield: 50%). The compound was identified by $^1$H-NMR and GC-MS.

$^1$H-NMR (CDCl$_3$, based on TMS): 7.0-6.0 (br, 7H), 3.2 (d, 1H), 2.9 (d, 1H), 2.3 (t, 2H), 1.4 (m, 4H), 0.9 (t, 3H), 0.1 (t, 3H), −0.2 ppm (s, 3H); GC-MS: 244 (MS)

<Step 3> synthesis of dimethylsilylene(cyclopentadienyl) (3-n-butylcyclopentadienyl)zirconium dichloride (A3)

The dimethylsilyl(3-n-butylcyclopentadienyl) (cyclopentadienyl) in an amount of 0.58 g (2.38 mmol) was dissolved in 30 ml of diethyl ether, and the solution was cooled to −78° C. A 1.57 M n-BuLi solution in a volume of 3.16 ml (4.99 mmol) was added thereto dropwise. The temperature was gradually increased, and the mixture was stirred at room temperature for 24 hours and was concentrated under reduced pressure. The concentrate was washed with 6 ml of hexane three times. The resultant white solid was suspended in 60 ml of hexane. To the suspension, 500 mg (2.15 mmol) of zirconium tetrachloride was added at −78° C. The temperature was gradually increased, and the mixture was stirred at room temperature for 24 hours. The mixture was then filtered and washed with hexane to remove salts. The filtrate was concentrated under reduced pressure to give 510 mg of a crude purified product. The crude product was washed with diethyl ether and pentane, and the solid obtained was dried under reduced pressure to give 190 mg of dimethylsilylene(cyclopentadienyl) (3-n-butylcyclopentadienyl)zirconium dichloride (A3) (yield: 20%). The compound was identified by $^1$H-NMR and FD-MS.

$^1$H-NMR (CDCl$_3$, based on TMS): 6.9 (d, 2H), 6.6 (s, 1H), 5.9 (t, 3H), 5.5 (s, 1H), 2.6 (m, 2H), 1.4 (m, 2H), 1.3 (m, 2H), 0.9 (t, 3H), 0.8 ppm (m, 3H); FD-MS: 404 (MS)

Synthetic Example 4

Synthesis of dimethylsilylene(cyclopentadienyl) (3-n-octylcyclopentadienyl)zirconium dichloride (A4)

<Step 1> synthesis of n-octylcyclopentadien

THF in a volume of 100 ml was added to 50 ml (100 mmol) of a 2 M THF solution of sodium cyclopentadienide, and the mixture was cooled to −78° C. A THF solution of 19.3 g (100 mmol) of 1-bromooctane was added thereto dropwise. Further, 11.4 g (100 mmol) of 1,3-dimethyl-2-imidazolidinone was added dropwise. The mixture was stirred at −78° C. The mixture was further stirred at room temperature for 24 hours and was cooled to 0° C. The reaction was terminated by adding 1N hydrochloric acid, and hexane was added to the reaction liquid. The organic layer was washed with a saturated aqueous sodium hydrogen carbonate solution and then with a saturated aqueous sodium chloride solution. The organic layer was dried over magnesium sulfate, was filtered, and was concentrated under reduced pressure. The concentrate was purified by distillation under reduced pressure to give 6.7 g (37.5 mmol) of target n-octylcyclopentadiene. The compound was identified by GC-MS. GC-MS: 178 (MS).

<Step 2> synthesis of dimethylsilyl(cyclopentadienyl) (3-n-octylcyclopentadienyl)

THF in a volume of 100 ml was added to 5.34 g (30 mmol) of the n-octylcyclopentadiene, and the mixture was cooled to −78° C. A 1.58 M hexane solution of n-butyllithium in a volume of 18.9 ml (30 mmol) was added thereto dropwise. The mixture was stirred at room temperature for 2 hours and was added dropwise to 50 ml of THF containing 14.3 g (110 mmol) of dimethylsilyl dichloride at −78° C. The temperature was gradually increased, and the mixture was stirred at room temperature for 24 hours. The mixture was concentrated under reduced pressure, and insolubles were removed by filtration. The filtrate was washed with hexane, and the hexane was distilled away from the filtrate under reduced pressure, thereby obtaining chlorodimethyl(3-n-octylcyclopentadienyl)silane. The compound was identified by GC-MS. Thereafter, 100 ml of THF was added to the reactor, and the temperature was lowered to −78° C. A 2 M THF solution of sodium cyclopentadienide in a volume of 15 ml (30 mmol) was added dropwise. The temperature was gradually increased, and the mixture was stirred at room temperature for 24 hours. After the reaction was confirmed to have proceeded sufficiently, water was added at 0° C. to terminate the reaction. The reaction liquid was extracted with hexane. The organic layer was washed with a saturated aqueous sodium hydrogen carbonate solution and then with a saturated saline solution, was dried over magnesium sulfate, and was filtered. The filtrate was concentrated under reduced pressure. The concentrate was purified by silica gel column chromatography (solvent: hexane/triethylamine=98/2 (v/v)) to give 3.5 g of dimethylsilyl(cyclopentadienyl)(3-n-octylcyclopentadienyl) (yield: 39%). The compound was identified by GC-MS. GC-MS: 300 (MS).

<Step 3> synthesis of dimethylsilylene(cyclopentadienyl) (3-n-octylcyclopentadienyl)zirconium dichloride (A4)

The dimethylsilyl(cyclopentadienyl) (3-n-octylcyclopentadienyl) in an amount of 3.1 g (10 mmol) was dissolved in 80 ml of diethyl ether, and the solution was cooled to −78° C. A 1.57 M hexane solution of n-butyllithium in a volume of 13.1 ml (20.5 mmol) was added thereto dropwise. The temperature was gradually increased, and the mixture was stirred at room temperature for 24 hours and was concentrated under reduced pressure. The concentrate was washed with hexane. The solid obtained was suspended in 80 ml of hexane. To the suspension, 1.96 g (8.4 mmol) of zirconium tetrachloride was added at −78° C. The temperature was gradually increased, and the mixture was stirred at room temperature for 24 hours. The mixture was then filtered and washed with hexane to remove salts. The filtrate was concentrated under reduced pressure and was washed with a solvent mixture consisting of diethyl ether and pentane. The resultant solid was dried under reduced pressure to give 240 mg of dimethylsilylene (cyclopentadienyl) (3-n-octylcyclopentadienyl) zirconium dichloride (yield: 5%). The compound was identified by $^1$H-NMR and FD-MS.

$^1$H-NMR (CDCl$_3$, based on TMS): 7.0 (s, 1H), 6.9 (s, 1H), 6.5 (s, 1H), 5.9-5.8 (m, 3H), 5.5 (s, 1H), 2.7 (m, 2H), 1.5 (m, 2H), 1.2 (m, 10H), 0.8 (t, 3H), 0.7 ppm (m, 6H); FD-MS: 458 (MS)

Synthetic Example 5

Synthesis of dimethylsilylene [3-(4,4,4-trifluorobutyl)cyclopentadienyl](cyclopentadienyl) zirconium dichloride (A5)

<Step 1> synthesis of [3-(4,4,4-trifluorobutyl)](cyclopentadienyl)chlorodimethylsilane THF in a volume of 150 ml was added to 1.5 g (8.5 mmol) of (4,4,4-trifluorobutyl)cyclopentadiene, and the mixture was cooled to 0° C. A 1.52 M hexane solution of n-butyllithium in a volume of 6.2 ml (1.5 mmol) was added thereto dropwise. The mixture was stirred at room temperature for 2 hours and was added dropwise to 50 ml of THF containing 0.29 g (2.3 mmol) of dimethylsilyl dichloride at −78° C. The temperature was gradually increased, and the mixture was stirred at room temperature for 24 hours to give a transparent solution. The solution was concentrated under reduced pressure, and insolubles were removed by filtration. The filtrate was washed with hexane, and the hexane was distilled away from the filtrate under reduced pressure. Dimethylsilyl dichloride was removed by distillation under reduced pressure. Thereafter, 100 ml of THF was added, and the mixture was cooled to −78° C. A 2 M THF solution of sodium cyclopentadiene in a volume of 4.7 ml (9.4 mmol) was gradually added dropwise. The mixture was stirred at room temperature for 24 hours, and water was added at 0° C. to terminate the reaction. The organic layer was extracted with hexane, was dried over magnesium sulfate, and was filtered. The filtrate was concentrated under reduced pressure. The concentrate was purified by silica gel column chromatography (solvent: hexane/triethylamine=98/2 (v/v)) to give 1.5 g of [3-(4,4,4-trifluorobutyl)](cyclopentadienyl)chlorodimethylsilane. The compound was identified by GC-MS. GC-MS: 298 (MS).

<Step 2> synthesis of dimethylsilylene [3-(4,4,4-trifluorobutyl)cyclopentadienyl](cyclopentadienyl)zirconium dichloride (A5)

The [3-(4,4,4-trifluorobutyl)](cyclopentadienyl)chlorodimethylsilane in an amount of 0.69 g (2.3 mmol) was dissolved in 30 ml of diethyl ether, and the solution was cooled to −78° C. A 1.57 M hexane solution of n-butyllithium in a volume of 3.0 ml (4.8 mmol) was added thereto dropwise. The temperature was gradually increased, and the mixture was stirred at room temperature for 24 hours. The mixture was concentrated under reduced pressure, and the concentrate was washed with 6 ml of hexane three times. The resultant white solid was suspended in 60 ml of hexane. To the suspension, 410 mg (1.8 mmol) of zirconium tetrachloride was added at −78° C. The temperature was gradually increased, and the mixture was stirred at room temperature for 24 hours. The mixture was then filtered and washed with hexane to remove insolubles. The filtrate was concentrated under reduced pressure to give 30 mg of dimethylsilylene [3-(4,4,4-trifluorobutyl)cyclopentadienyl](cyclopentadienyl) zirconium dichloride (A5). The compound was identified by $^1$H-NMR and FD-MS.

$^1$H-NMR (CDCl$_3$, based on TMS): 7.2-5.5 (m, 7H), 2.6 (m, 2H), 2.3-1.8 (m, 4H), 1.4-0.6 ppm (m, 6H); FD-MS: 458 (MS)

Synthetic Example 6

Synthesis of dimethylsilylene (3-butyl-2,4,5-trimethylcyclopentadienyl)(cyclopentadienyl)zirconium dichloride (A6)

<Step 1> synthesis of 2-butyl-1,3,4-trimethylcyclopentadiene

To a reactor, 259 g of polyphosphoric acid was added. At 40° C., 50.7 g of sec-butyl methacrylate was added dropwise with stirring. The mixture was stirred for 1 hour. The temperature was increased to 80° C., and the mixture was stirred at the temperature for 1 minute and was thereafter cooled. The reaction liquid was slowly rendered alkaline by addition of an aqueous sodium hydroxide solution. The reaction liquid was extracted with hexane and diethyl ether. The organic layer was dried over sodium sulfate, was concentrated under reduced pressure, and was purified by distillation under reduced pressure. To 6.8 g of 2,3,5-trimethylcyclopent-2-enone thus obtained, 75 ml of diethyl ether was added, followed by cooling to −78° C. A 0.84 M THF solution of n-butylmagnesium chloride in a volume of 72 ml was added thereto dropwise over a period of 25 minutes. The temperature was gradually increased to room temperature, and the mixture was stirred for 24 hours. Thereafter, a saturated aqueous ammonia chloride solution was added dropwise at −10° C. The mixture was stirred for 10 minutes, and a 20% aqueous sulfuric acid solution was added. The organic layer was extracted with diethyl ether, was washed with a saturated aqueous sodium hydrogen carbonate solution, and was concentrated under reduced pressure. The concentrate was purified by distillation under reduced pressure and silica gel column chromatography (solvent: hexane) to give 5.2 g of 2-butyl-1,3,4-trimethylcyclopentadiene. The compound was identified by GC-MS. GC-MS: 164 (MS).

<Step 2> synthesis of (2-butyl-1,3,4-trimethylcyclopentadienyl)(cyclopentadienyl)dimethylsilane THF in a volume of 100 ml was added to 1.6 g (12.9 mmol) of the 2-butyl-1,3,4-trimethylcyclopentadiene, and the mixture was cooled to 0° C. A 1.57 M hexane solution of n-butyllithium in a volume of 8.6 ml (13.5 mmol) was added thereto dropwise. The mixture was stirred at room temperature for 2 hours. At −78° C., 50 ml of THF containing 2.0 g (15.5 mmol) of dimethylsilyl dichloride was added dropwise. The temperature was gradually increased, and the mixture was stirred at room temperature for 8 hours to give a transparent solution. The solution was concentrated under reduced pressure, and the concentrate was filtered to remove insolubles. The filtrate was washed with hexane, and the hexane was distilled away from the filtrate under reduced pressure. Dimethylsilyl dichloride was removed by distillation under reduced pressure. Thereafter, 100 ml of THF was added, and the mixture was cooled to −78° C. A 2 M THF solution of sodium cyclopentadienide in a volume of 4.7 ml (9.4 mmol) was gradually added dropwise. The mixture was stirred at room temperature for 24 hours, and water was added at 0° C. to terminate the reaction. The organic layer was extracted with hexane, was washed with a saturated aqueous sodium chloride solution, was dried over magnesium sulfate, and was filtered. The filtrate was concentrated under reduced pressure. The concentrate was purified by silica gel column chromatography (solvent: hexane/triethylamine=98/2 (v/v)) to give 4.6 g (16.1 mmol) of (3-butyl-2,4,5-trimethylcyclopentadienyl) (cyclopentadienyl)dimethylsilane. The compound was identified by GC-MS. GC-MS: 286 (MS).

<Step 3> synthesis of dimethylsilylene (3-butyl-2,4,5-trimethylcyclopentadienyl)(cyclopentadienyl)zirconium dichloride (A6)

The (3-butyl-2,4,5-trimethylcyclopentadienyl) (cyclopentadienyl)dimethylsilane in an amount of 0.53 g (1.9 mmol) was dissolved in 50 ml of diethyl ether, and the solution was cooled to −78° C. A 1.57 M hexane solution of n-butyllithium in a volume of 0.76 ml (1.7 mmol) was added thereto dropwise. The temperature was gradually increased, and the mixture was stirred at room temperature for 24 hours and was concentrated under reduced pressure. The concentrate was washed with 6 ml of hexane three times. The resultant solid was suspended in 50 ml of hexane. To the suspension, 400 mg (1.7 mmol) of zirconium tetrachloride was added at −78° C. The temperature was gradually increased, and the mixture was stirred at room temperature for 24 hours. The mixture was then filtered and washed with hexane to remove salts. The residue was dissolved in diethyl ether, and pentane was added thereto with stirring to cause gradual precipitation. The precipitate was washed with pentane, and the solid was dried by concentration under reduced pressure to give 30 mg of dimethylsilylene (3-butyl-2,4,5-trimethylcyclopentadienyl) (cyclopentadienyl) zirconium dichloride (A6). The compound was identified by 1H-NMR and FD-MS.

$^1$H-NMR (CDCl$_3$, based on TMS): 6.9 (s, 2H), 5.6 (s, 2H), 5.6 (2H), 2.4-2.2 (m, 2H), 2.0-1.8 (m, 9H), 1.5-1.2 (m, 4H), 0.9-0.7 (m, 9H); FD-MS: 444 (MS)

Synthetic Example 7

Synthesis of dibutylsilylene(3-n-butylcyclopentadienyl) (cyclopentadienyl)zirconium dichloride (A7)

<Step 1> synthesis of dibutylchloro(cyclopentadienyl)silane

THF in a volume of 100 ml was added to 100 ml (200 mmol) of a 2M THF solution of sodium cyclopentadienide. The mixture was cooled to −78° C., and 100 ml of THF was added thereto. Further, 21.3 g (100 mmol) of dibutyldichlorosilane was gradually added dropwise. The mixture was stirred at room temperature for 24 hours and was concentrated under reduced pressure, and unreacted materials were distilled away. The residue was used in the next step without further purification.

<Step 2> synthesis of dibutylsilyl (3-n-butylcyclopentadienyl)(cyclopentadienyl)

The n-butylcyclopentadiene in an amount of 6.3 g (51.5 mmol) was dissolved in 120 ml of THF, and the solution was cooled to 0° C. A 1.58M hexane solution of n-butyllithium in a volume of 32.8 ml (51.5 mmol) was added thereto dropwise over a period of 30 minutes. The mixture was stirred at room temperature for 2 hours and was cooled to −78° C. Dibutylchloro(cyclopentadienyl)silane in an amount of 20.3 g (95.2 mmol) dissolved in 100 ml of THF was gradually added dropwise. The mixture was stirred at room temperature for 8 hours and at 45° C. for 8 hours. The mixture was then cooled to 0° C., and water was added to terminate the reaction. The reaction liquid was extracted with ethyl acetate. The organic layer was washed with a saturated aqueous sodium carbonate solution and then with a saturated saline solution, was dried over magnesium sulfate, and was filtered. The filtrate was concentrated under reduced pressure. The concentrated liquid was purified by neutral silica gel column chromatography (solvent: hexane/triethylamine=98/2 (v/v)) to give 1.42 g of dibutylsilyl(3-n-butylcyclopentadienyl) (cyclopentadienyl) (yield: 8%). The compound was identified by $^1$H-NMR and GC-MS.

$^1$H-NMR (CDCl$_3$, based on TMS): 7.0-5.5 (s, 7H), 3.1-2.3 (m, 2H), 1.9-0.9 (m, 25H); GC-MS: 328 (MS)

<Step 3> synthesis of dibutylsilylene (3-n-butylcyclopentadienyl)(cyclopentadienyl)zirconium dichloride (A7)

The dibutylsilyl(3-n-butylcyclopentadienyl) (cyclopentadienyl) in an amount of 1.4 g (4.3 mmol) was dissolved in 50 ml of diethyl ether, and the solution was cooled to −78° C. A 1.58 M hexane solution of n-butyllithium in a volume of 5.6 ml (8.8 mmol) was added thereto dropwise. The temperature was gradually increased, and the mixture was stirred at room temperature for 24 hours and was concentrated under reduced pressure. The concentrate was washed with hexane and was filtered. The solid obtained was suspended in 80 ml of hexane. To the suspension, 0.95 g (4.1 mmol) of zirconium tetrachloride was added at −78° C. The temperature was gradually increased, and the mixture was stirred at room temperature for 24 hours. The mixture was then filtered and washed with hexane to remove salts. The filtrate was concentrated under reduced pressure to give 1.2 g of dibutylsilylene(3-n-butylcyclopentadienyl) (cyclopentadienyl)zirconium dichloride (A7) (yield: 57%). The compound was identified by $^1$H-NMR and FD-MS.

$^1$H-NMR (CDCl$_3$, based on TMS): 7.0-5.5 (s, 7H), 2.7 (m, 2H), 1.8-0.9 (m, 25H); FD-MS: 486 (MS)

Synthetic Example 8

Synthesis of (pentyl)(methyl)silylene (3-n-butylcyclopentadienyl)(cyclopentadienyl) zirconium dichloride (A8)

<Step 1> synthesis of chloro(chloromethyl) (cyclopentadienyl)(methyl)silane

THF in a volume of 100 ml was added to 6 g (49 mmol) of n-butylcyclopentadiene, and the mixture was cooled to −78° C. A 1.65 M hexane solution of n-butyllithium in a volume of 29.6 ml (48.8 mmol) was added thereto dropwise. The mixture was stirred at room temperature for 2 hours and was cooled again to −78° C. Dichloro(chloromethyl)(methyl)silane in an amount of 8.0 g (49 mmol) dissolved in 50 ml of THF was added dropwise. The mixture was stirred at room temperature for 3 hours and was concentrated under reduced pressure. Hexane was added, and the mixture was filtered. The filtrate was distilled under reduced pressure to give 3.43 g of target chloro(chloromethyl) (cyclopentadienyl)(methyl) silane.

<Step 2> synthesis of (pentyl)(methyl)silylene (3-n-butylcyclopentadienyl)(cyclopentadienyl)zirconium dichloride (A8)

THF in a volume of 100 ml was added to chloro(chloromethyl) (cyclopentadienyl)(methyl) silane, and the mixture was cooled to −78° C. A 2 M THF solution of sodium cyclopentadienide in a volume of 6.9 ml (13.8 mmol) was added thereto dropwise. The mixture was stirred at room temperature for 24 hours and was cooled to 0° C. Water was added to terminate the reaction. The reaction liquid was extracted with hexane. The organic layer was extracted with a saturated aqueous sodium hydrogen carbonate solution and then with a saturated saline solution, was dried over magnesium sulfate, and was purified by silica gel column chromatography (solvent: hexane/triethylamine=98/2 (v/v)). The resultant ligand in an amount of 1.6 g (5.74 mmol) was dissolved in 50 ml of diethyl ether, and the solution was cooled to −78° C. A 1.58 M hexane solution of n-butyllithium in a volume of 7.12 ml (8.8 mmol) was added thereto dropwise. The temperature was increased gradually. The mixture was stirred at room temperature for 24 hours, was concentrated under reduced pressure, was washed with hexane, and was filtered. The solid obtained was suspended in 60 ml of hexane. To the suspension, 0.88 g (5.2 mmol) of zirconium tetrachloride was added at −78° C. The temperature was gradually increased, and the mixture was stirred at room temperature for 24 hours. The mixture was then filtered and washed with hexane to remove salts. The filtrate was concentrated under reduced pressure to give 0.15 g of pentyl)(methyl) silylene(3-n-butylcyclopentadienyl) (cyclopentadienyl) zirconium dichloride (A8) (yield: 6%). The compound was identified by $^1$H-NMR and FD-MS.

$^1$H-NMR (CDCl$_3$, based on TMS): 7.0-6.8 (m, 2H), 6.5 (m, 1H), 5.9-5.7 (m, 3H), 5.5 (s, 1H), 2.6 (m, 2H), 1.6-0.6 (m, 21H); FD-MS: 458 (MS)

Synthetic Example 9

Synthesis of (chloromethyl)(methyl)silylene (3-n-butylcyclopentadienyl)(cyclopentadienyl)zirconium dichloride (A9)

<Step 1> synthesis of (chloromethyl)(methyl)silylene (3-n-butylcyclopentadienyl)(cyclopentadienyl) zirconium dichloride (A9)

(3-n-Butylcyclopentadienyl)(chloromethyl) (cyclopentadienyl)(methyl)silane in an amount of 1.3 g (4.7 mmol) was dissolved in 60 ml of diethyl ether, and the solution was cooled to −78° C. A 1.65 M hexane solution of n-butyllithium in a volume of 5.7 ml (9.3 mmol) was added thereto dropwise. The temperature was gradually increased, and the mixture was stirred at 10° C. for 3 hours and was concentrated under reduced pressure. The concentrate was suspended in 60 ml of hexane. To the suspension, 0.97 g (4.2 mmol) of zirconium tetrachloride was added at −78° C. The temperature was gradually increased, and the mixture was stirred at room temperature for 24 hours. The mixture was then filtered and washed with hexane to remove insolubles. The filtrate was concentrated under reduced pressure and was re-slurried with diethyl ether and n-pentane. The supernatant was removed, and the residue was washed with n-pentane. The solid obtained was concentrated to give 200 mg of (chloromethyl) (methyl)silylene (3-n-butylcyclopentadienyl)(cyclopentadienyl)zirconium dichloride (A9) (yield: 4.8%). The compound was identified by $^1$H-NMR and FD-MS.

$^1$H-NMR (CDCl$_3$, based on TMS): 7.1-5.5 (m, 7H), 3.4 (d, 2H), 2.6 (m, 2H), 1.6-1.2 (m, 4H), 0.9-0.7 (m, 6H), 1.6-0.6 (m, 21H); FD-MS: 436 (MS)

Synthetic Example 10

Synthesis of dimethylmethylene (3-n-butylcyclopentadienyl)(cyclopentadienyl)zirconium dichloride (A10)

<Step 1> synthesis of dimethylmethylene (3-n-butylcyclopentadienyl)(cyclopentadienyl)

1,2-Dimethoxyethane in a volume of 100 ml was added to 5 g (40.9 mmol) of n-butylcyclopentadiene, and the mixture was cooled to 0° C. Potassium hydroxide in an amount of 2.8 g (50 mmol) was added. The temperature was gradually increased, and the mixture was stirred under reflux for 1 hour. At 0° C., 4.34 g (41 mmol) of 6,6-dimethylfulvene was added, and the mixture was stirred under reflux for 3 hours. The reaction liquid was cooled to 0° C., and the reaction was terminated by adding 1 N-hydrochloric acid. The organic layer was extracted with hexane and was washed with a saturated aqueous sodium hydrogen carbonate solution and a saturated saline solution. The reaction product was purified by silica gel column chromatography (solvent: hexane/triethylamine=98/2 (v/v)) to give 3.2 g (14 mmol) of dimethylmethylene (3-n-butylcyclopentadienyl)(cyclopentadienyl). The compound was identified by $^1$H-NMR and GC-MS.

$^1$H-NMR (CDCl$_3$, based on TMS): 6.6-5.5 (m, 7H), 3.0-2.7 (d, 2H), 2.6-2.4 (m, 2H), 1.6-0.9 (m, 13H); GC-MS: 228 (MS)

<Step 2> synthesis of dimethylmethylene (3-n-butyl-cyclopentadienyl)(cyclopentadienyl)zirconium dichloride (A10)

The ligand in an amount of 1.3 g (4.66 mmol) was dissolved in 60 ml of diethyl ether, and the solution was cooled to −78° C. A 1.65 M n-BuLi solution in a volume of 5.7 ml (9.3 mmol) was added thereto dropwise. The temperature was gradually increased, and the mixture was stirred at 10° C. for 3 hours and was concentrated under reduced pressure. The concentrate was suspended in 60 ml of hexane. To the suspension, 0.97 g (4.2 mmol) of zirconium tetrachloride was added at −78° C. The temperature was gradually increased, and the mixture was stirred at room temperature for 24 hours. The mixture was then filtered and washed with hexane to remove insolubles. The filtrate was concentrated under reduced pressure and was washed with diethyl ether and n-pentane. The supernatant was removed, and the residue was washed with pentane. The insoluble portion obtained was concentrated to give 200 mg of dimethylmethylene (3-n-butylcyclopentadienyl)(cyclopentadienyl)zirconium dichloride (A10) (yield: 4.8%). The compound was identified by $^1$H-NMR and FD-MS.

$^1$H-NMR (CDCl$_3$, based on TMS): 7.1-5.5 (m, 7H), 3.4 (d, 2H), 2.6 (m, 2H), 1.6-1.2 (m, 4H), 0.9-0.7 (m, 6H), 1.6-0.6 (m, 21H); FD-MS: 436 (MS)

Example L-1

Polymerization

A 500 mL glass vessel thoroughly purged with nitrogen was charged with 400 mL of purified toluene, and ethylene was passed through the vessel to saturate the liquid phase and the gas phase with ethylene. Under the stream of ethylene, the temperature was increased to 75° C. and methylaluminoxane (1.0 mmol in terms of Al) was added. Further, a toluene solution of the metallocene compound (A1) (0.0005 mmol in terms of Zr) was added. Polymerization was performed while supplying ethylene at 100 L/hr at 75° C. for 10 minutes. The polymer obtained was deashed with hydrochloric acid/methanol and was dried under vacuum for 10 hours to afford 2.41 g of an ethylene homopolymer. Results of analysis of the polymer are set forth in Table 1.

Examples L-2 to L-10

The procedures of Example L-1 were repeated, except that the metallocene compound (A1) used in Example L-1 was replaced by the metallocene compounds (A2 to A10) in varied amounts. Results of analysis of the polymers obtained in Examples L-2 to L-10 are set forth in Table 1 together with the results of Example L-1.

Example L-11

Preparation of Solid Component (S)

In a 260 L reactor equipped with a stirrer, 10 kg of silica (SiO$_2$:average particle diameter:60 μm) that had been dried at 250° C. for 10 hours was suspended in 90.5 L of toluene in a nitrogen atmosphere. The suspension was cooled to 0 to 5° C. A toluene solution of methylalumoxane (3.0 mmol/mL in terms of Al atom) in a volume of 45.5 L was added dropwise to the suspension over a period of 30 minutes. During the dropwise addition, the temperature in the system was maintained at 0 to 5° C. After the dropwise addition, the reaction was continuously performed at 0 to 5° C. for 30 minutes. Thereafter, the temperature was increased to 95 to 100° C. in about 1.5 hours, and the reaction was conducted at 95 to 100° C. for 4 hours. The temperature was then lowered to ambient, and the supernatant was removed by decantation. The solid component thus obtained was washed with toluene two times, and toluene was added thereto to a total volume of 129 L, thereby preparing a toluene slurry of the solid component (S). A portion of the solid component was sampled and the concentrations were determined, resulting in a slurry concentration of 96.5 g/L and an Al concentration of 0.489 mol/L.

Preparation of Solid Catalyst Component (X-1)

A 200 mL glass flask purged with nitrogen was charged with 50 mL of toluene, and the toluene slurry of the solid component (S) (1.0 g in terms of the solid component) was added thereto. Further, 12.7 mL of a toluene solution of the metallocene compound (A1) (0.002 mmol/mL in terms of Zr atom) was added dropwise. Reaction was performed at room temperature for 1 hour. The supernatant was removed by decantation. The residue was washed with heptane two times and was slurried into 100 mL of a heptane slurry (solid catalyst component X-1). A portion of the heptane slurry of the solid catalyst component (X-1) was sampled and the concentrations were determined, resulting in a Zr concentration of 0.023 mg/mL and an Al concentration of 1.3 mg/mL.

Polymerization

A 1 L SUS autoclave thoroughly purged with nitrogen was charged with 500 mL of purified heptane, and ethylene was passed through the autoclave to saturate the liquid phase and the gas phase with ethylene. Further, 10 mL of 1-hexene and 0.375 mmol of triisobutylaluminum were added, and 40 mg in terms of the solid component of the solid catalyst component (X-1) was added to the autoclave. The temperature was increased to 80° C., and polymerization was performed at 0.78 MPa·G for 90 minutes. The polymer obtained was dried under vacuum for 10 hours to afford 24.61 g of an ethylene/1-hexene copolymer. Results of GPC analysis and properties of the polymer are set forth in Table 1.

Examples L-12 to L-20

Preparation of solid catalyst components (X-2 to X-10)

Solid catalyst components (X-2 to X-10) were prepared in the same manner as for the solid catalyst component (X-1) in Example L-11, except that the metallocene compound (A1) was replaced by the metallocene compounds (A2 to A10).

Polymerization

Polymerization was performed in the same manner as in Example L-11, except that the solid catalyst component (X-1) was replaced by the solid catalyst components (X-2 to X-10) with varied amounts of the solid catalyst. Results of GPC analysis and properties of the polymers are set forth in Table 1.

Example L-21

Polymerization

A 2 L SUS autoclave thoroughly purged with nitrogen was charged with 250 g of NaCl, and the content was dried under vacuum at 100° C. for 90 minutes. Subsequently, the pressure inside the autoclave was returned to normal pressure by supplying 1-butene/ethylene mixture gas (1-butene concentration: 4 vol %), and the inside temperature was adjusted at 75° C. Under a stream of the mixture gas, 0.75 mmol of triisobutylaluminum was added, and 25 mg in terms of the solid component of the solid catalyst component (X-2) was added to the autoclave. Polymerization was performed at 0.78 MPa·G and 80° C. for 90 minutes. The product was washed with sufficient amounts of water to remove NaCl completely. The polymer was dried under vacuum for 10 hours to afford 39.5 g of an ethylene/1-butene copolymer. Results of GPC analysis and properties of the polymer are set forth in Table 2.

Example L-22

Polymerization

Polymerization was performed in the same manner as in Example L-21, except that the solid catalyst component (X-2) was replaced by the solid catalyst component (X-3) with a varied amount of the solid catalyst. Results of GPC analysis and properties of the polymer are set forth in Table 2.

Example L-23

Polymerization

Polymerization was performed in the same manner as in Example L-21, except that the solid catalyst component (X-2) was replaced by the solid catalyst component (X-4) with a varied amount of the solid catalyst. Results of GPC analysis and properties of the polymer are set forth in Table 2.

Example L-24

Polymerization

Polymerization was performed in the same manner as in Example L-21, except that the solid catalyst component (X-2) was replaced by the solid catalyst component (X-6) with a varied amount of the solid catalyst. Results of GPC analysis and properties of the polymer are set forth in Table 2.

Comparative Example L-1

Polymerization

Polymerization was performed in the same manner as in Example L-1, except that the metallocene compound (A1) was replaced by a metallocene compound (E1). Results of GPC analysis and properties of the polymer are set forth in Table 3. The metallocene compound (E1) used in Comparative Example is illustrated below.

E1: dimethylsilylenebis(cyclopentadienyl)zirconium dichloride

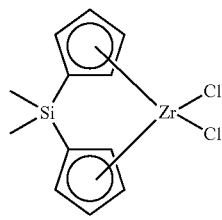

E1

Comparative Example L-2

Polymerization

Polymerization was performed in the same manner as in Example L-1, except that the metallocene compound (A1) was replaced by a metallocene compound (E2) and the amount of the catalyst was changed. Results of GPC analysis and properties of the polymer are set forth in Table 3. The metallocene compound (E2) used in Comparative Example is illustrated below.

E2: dimethylsilylenebis(3-n-butylcyclopentadienyl) zirconium dichloride

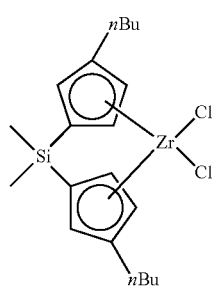

E2

Comparative Example L-3

Polymerization

Polymerization was performed in the same manner as in Example L-1, except that the metallocene compound (A1) was replaced by a metallocene compound (E3). Results of GPC analysis and properties of the polymer are set forth in Table 3. The metallocene compound (E3) used in Comparative Example is illustrated below.

E3: dimethylsilylenebis(3-tert-butylcyclopentadienyl) zirconium dichloride

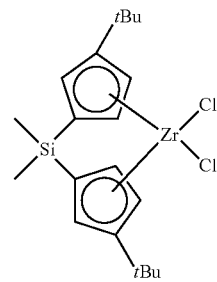

E3

Comparative Example L-4

Polymerization

Polymerization was performed in the same manner as in Example L-1, except that the metallocene compound (A1) was replaced by a metallocene compound (E4) and the amount of the catalyst was changed. Results of GPC analysis and properties of the polymer are set forth in Table 3. The metallocene compound (E4) used in Comparative Example is illustrated below.

E4: dimethylsilylenebis(2,4-dimethylcyclopentadienyl) zirconium dichloride

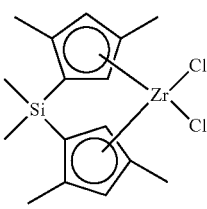

E4

Comparative Example L-5

Polymerization

Polymerization was performed in the same manner as in Example L-1, except that the metallocene compound (A1) was replaced by a metallocene compound (E5). Results of GPC analysis and properties of the polymer are set forth in Table 3. The metallocene compound (E5) used in Comparative Example is illustrated below.

E5: dimethylsilylenebis(2,3,5-trimethylcyclopentadienyl)zirconium dichloride

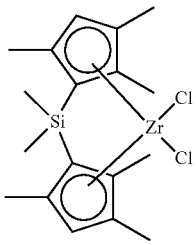

Comparative Example L-6

Preparation of Solid Catalyst Component (EX-1)

A solid catalyst component (EX-1) was prepared in the same manner as for the solid catalyst component (X-1) in Example L-11, except that the metallocene compound (A1) was replaced by the metallocene compound (E1).

Polymerization

Polymerization was performed in the same manner as in Example L-11, except that the solid catalyst component (X-1) was replaced by the solid catalyst component (EX-1) with a varied amount of the solid catalyst. Results of GPC analysis and properties of the polymer are set forth in Table 3.

Comparative Examples L-7 to L-12

Preparation of Solid Catalyst Components (EX-2 to EX-7)

Solid catalyst components (EX-2 to EX-7) were prepared in the same manner as for the solid catalyst component (X-1) in Example L-11, except that the metallocene compound (A1) was replaced by the metallocene compounds (E2 to E7). The metallocene compounds (E6 and E7) used in Comparative Examples are illustrated below.

E6: bis(cyclopentadienyl) zirconium dichloride

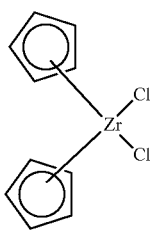

E7: bis(n-butylcyclopentadienyl)zirconium dichloride

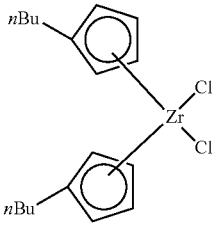

Polymerization

Polymerization was performed in the same manner as in Example L-11, except that the solid catalyst component (X-1) was replaced by the solid catalyst components (EX-2 to EX-7) with varied amounts of the solid catalyst. Results of analysis of the polymers obtained in Comparative Examples L-7 to L-12 are set forth in Table 3 together with the results in Comparative Example L-6.

The results of Examples and Comparative Examples show that the bridged metallocene compounds (the components (A)) according to the invention can afford polymers having a lower molecular weight and a larger number of terminal vinyl bonds with higher catalytic activity than the conventional symmetric metallocene compounds.

(2) Olefin Polymerization Processes Using Olefin Polymerization Catalysts (b)

Synthetic Example 11

A compound (B1) represented by the following formula was synthesized by a method described in JP-A-H04-69394.

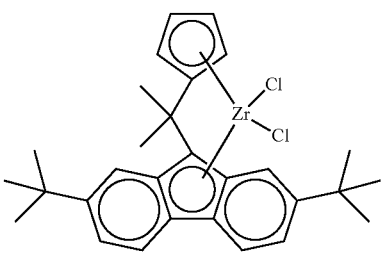

Synthetic Example 12

A compound (B2) represented by the following formula was synthesized by a method described in EP351392.

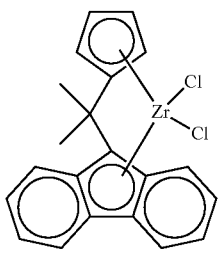

Synthetic Example 13

A compound (B3) represented by the following formula was synthesized by a method described in JP-A-2000-212194.

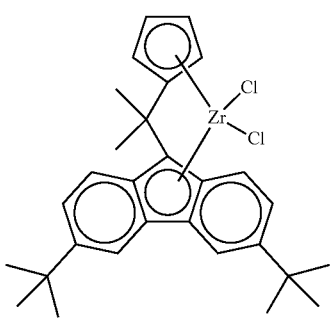

B3

Synthetic Example 14

A compound (B4) represented by the following formula was synthesized by a method described in EP955305.

B4

Synthetic Example 15

A compound (B5) represented by the following formula was synthesized by a method described in JP-A-2005-200451.

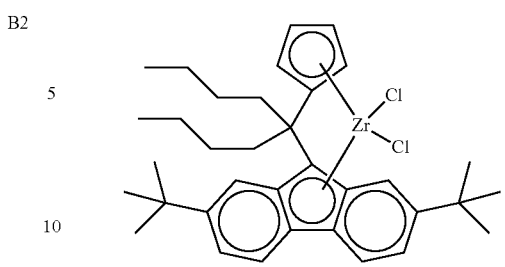

B2

B5

Synthetic Example 16

A compound (B6) represented by the following formula was synthesized by a method described in JP-A-2004-168744.

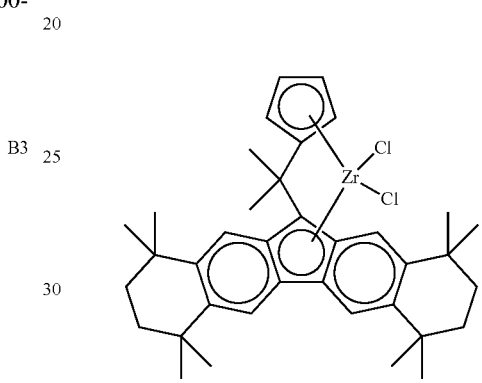

B6

Example M-1

Preparation of Solid Catalyst Component (Y-1)

A 200 mL glass flask purged with nitrogen was charged with 50 mL of toluene, and the toluene slurry of the solid component (S) (1.0 g in terms of the solid component) prepared in Example L-11 was added thereto. Further, 7.6 mL of a toluene solution of the metallocene compound (dimethylsilylene (cyclopentadienyl)(3-n-propylcyclopentadienyl) zirconium dichloride (A2)) (0.002 mmol/mL in terms of Zr atom) and 5.1 mL of a toluene solution of the metallocene compound (B1) (0.002 mmol/mL in terms of Zr atom) were added dropwise as a mixture ((A2)/(B1) molar ratio=60/40). Reaction was performed at room temperature for 1 hour. After the reaction for 1 hour, Zr was not detected in the supernatant toluene. The supernatant was removed by decantation. The residue was washed with heptane two times and was slurried into 50 mL of a heptane slurry (solid catalyst component Y-1). A portion of the heptane slurry of the solid catalyst component (Y-1) was sampled and the concentrations were determined, resulting in a Zr concentration of 0.046 mg/mL and an Al concentration of 2.6 mg/mL.

Polymerization

A 1 L SUS autoclave thoroughly purged with nitrogen was charged with 500 mL of purified heptane, and ethylene was passed through the autoclave to saturate the liquid phase and the gas phase with ethylene. Thereafter, 10 mL of 1-hexene and 0.375 mmol of triisobutylaluminum were added, and 20

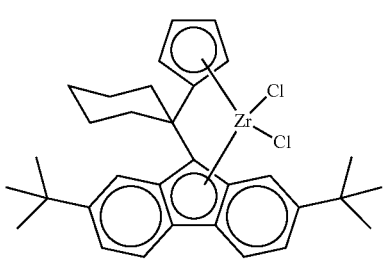

mg in terms of the solid component of the solid catalyst component (Y-1) was added to the autoclave. The temperature was increased to 80° C., and polymerization was performed at 0.78 MPa·G for 90 minutes. The polymer obtained was dried under vacuum for 10 hours to afford 76.3 g of an ethylene/1-hexene copolymer. Results of GPC analysis and properties of the polymer are set forth in Table 4, and a GPC chart is shown in FIG. 1.

Example M-2

Polymerization

Polymerization was carried out in the same manner as in Example M-1, except that the ethylene gas was replaced by hydrogen/ethylene mixture gas (hydrogen concentration: 0.1 vol %). The polymer obtained was dried under vacuum for 10 hours to afford 75.5 g of an ethylene/1-hexene copolymer. Results of GPC analysis and properties of the polymer are set forth in Table 4.

Example M-3

Polymerization

A 2 L SUS autoclave thoroughly purged with nitrogen was charged with 250 g of NaCl, and the content was dried under vacuum at 100° C. for 90 minutes. Subsequently, the pressure inside the autoclave was returned to normal pressure by supplying 1-butene/ethylene mixture gas (1-butene concentration: 4 vol %), and the inside temperature was adjusted at 75° C. Under a stream of the mixture gas, 0.75 mmol of triisobutylaluminum was added, and 34.4 mg in terms of the solid component of the solid catalyst component (Y-1) was added to the autoclave. Polymerization was performed at 0.78 MPa·G and 80° C. for 90 minutes. The product was washed with sufficient amounts of water to remove NaCl completely. The polymer was dried under vacuum for 10 hours to afford 68.9 g of an ethylene/1-butene copolymer. Results of GPC analysis and properties of the polymer are set forth in Table 4. Properties measured with respect to a sample of this polymer are indicated in Table 13.

Example M-4

Preparation of Solid Catalyst Component (Y-2)

A 200 mL glass flask purged with nitrogen was charged with 50 mL of toluene, and the toluene slurry of the solid component (S) (1.0 g in terms of the solid component) prepared in Example L-11 was added thereto. Further, 7.6 mL of a toluene solution of the metallocene compound (dimethylsilylene (cyclopentadienyl)(3-n-butylcyclopentadienyl) zirconium dichloride (A3)) (0.002 mmol/mL in terms of Zr atom) and 5.1 mL of a toluene solution of the metallocene compound (B1) (0.002 mmol/mL in terms of Zr atom) were added dropwise as a mixture ((A3)/(B1) molar ratio=60/40). Reaction was performed at room temperature for 1 hour. After the reaction for 1 hour, Zr was not detected in the supernatant toluene. The supernatant was removed by decantation. The residue was washed with heptane two times and was slurried into 50 mL of a heptane slurry (solid catalyst component Y-2). A portion of the heptane slurry of the solid catalyst component (Y-2) was sampled and the concentrations were determined, resulting in a Zr concentration of 0.034 mg/mL and an Al concentration of 2.1 mg/mL.

Polymerization

Figure 2:
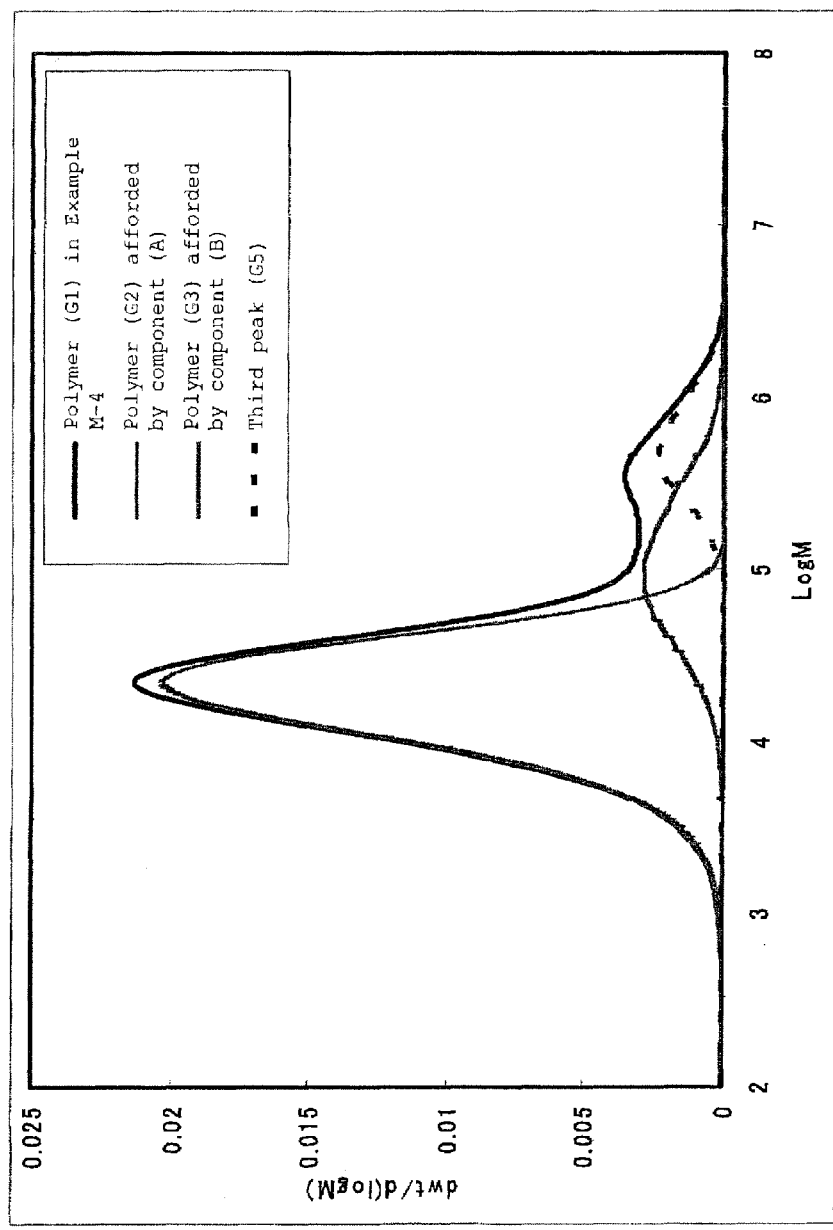
FIG. 2 is a GPC chart of a polymer obtained in Example M-4.

Polymerization was carried out in the same manner as in Example M-1, except that the solid catalyst component (Y-1) was replaced by 15 mg of the solid catalyst component (Y-2). The polymer obtained was dried under vacuum for 10 hours to afford 60.2 g of an ethylene/1-hexene copolymer. Results of GPC analysis and properties of the polymer are set forth in Table 4, and a GPC chart is shown in FIG. 2. Properties measured with respect to a sample of this polymer are indicated in Table 16.

Example M-5

Polymerization

Figure 3:
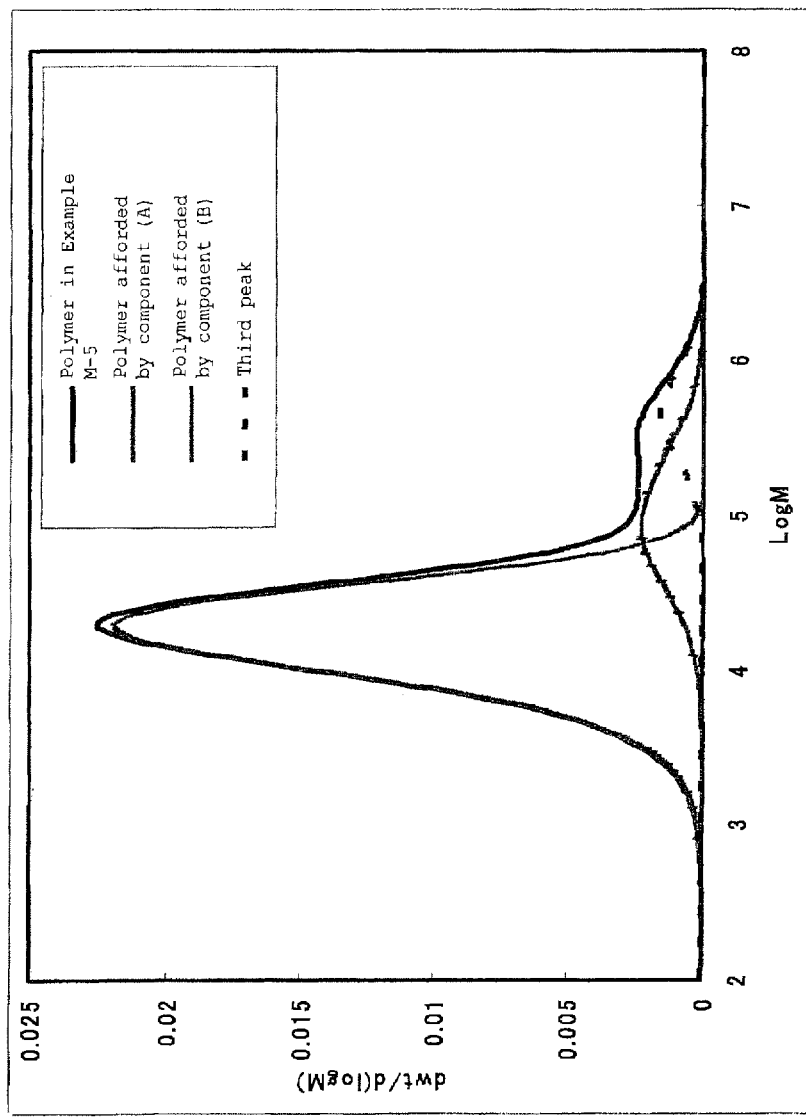
FIG. 3 is a GPC chart of a polymer obtained in Example M-5.

Polymerization was carried out in the same manner as in Example M-4, except that the ethylene gas was replaced by hydrogen/ethylene mixture gas (hydrogen concentration: 0.05 vol %). The polymer obtained was dried under vacuum for 10 hours to afford 55.1 g of an ethylene/1-hexene copolymer. Results of GPC analysis and properties of the polymer are set forth in Table 4, and a GPC chart is shown in FIG. 3. Properties measured with respect to a sample of this polymer are indicated in Table 16.

Example M-6

Polymerization

Figure 4:
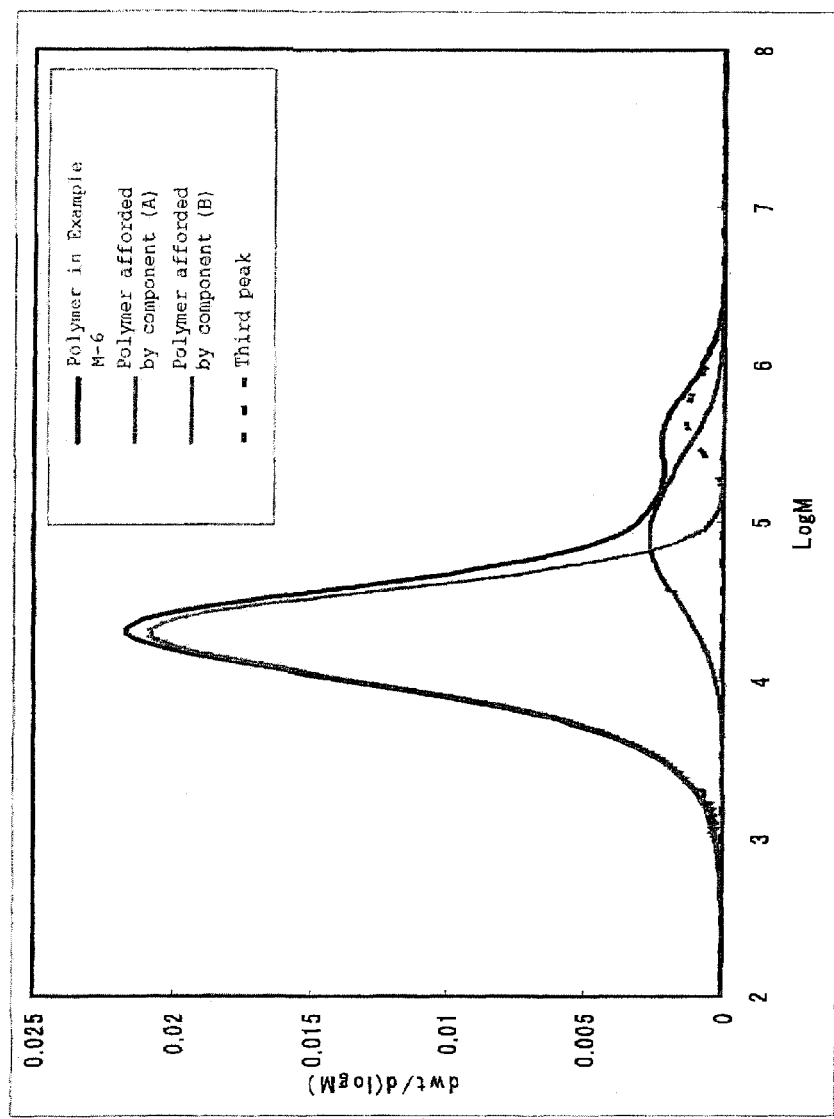
FIG. 4 is a GPC chart of a polymer obtained in Example M-6.

Polymerization was carried out in the same manner as in Example M-3, except that the solid catalyst component (Y-1) was replaced by 34.4 mg of the solid catalyst component (Y-2). The polymer obtained was dried under vacuum for 10 hours to afford 41.6 g of an ethylene/1-butene copolymer. Results of GPC analysis and properties of the polymer are set forth in Table 4, and a GPC chart is shown in FIG. 4. Properties measured with respect to a sample of this polymer are indicated in Table 13.

Example M-7

Preparation of Solid Catalyst Component (Y-3)

A solid catalyst component (Y-3) was synthesized in the same manner as for the solid catalyst component (Y-1) in Example M-1, except that the metallocene compound (A2) was replaced by the metallocene compound (A4), and the reaction molar ratio of the metallocene compound (A4) and the metallocene compound (B1) was (A4)/(B1)=80/20 (molar ratio). After the reaction for 1 hour, Zr was not detected in the supernatant toluene. A portion of the heptane slurry of the solid catalyst component (Y-3) was sampled and the concentrations were determined, resulting in a Zr concentration of 0.049 mg/mL and an Al concentration of 3.2 mg/mL.

Polymerization

Figure 5:
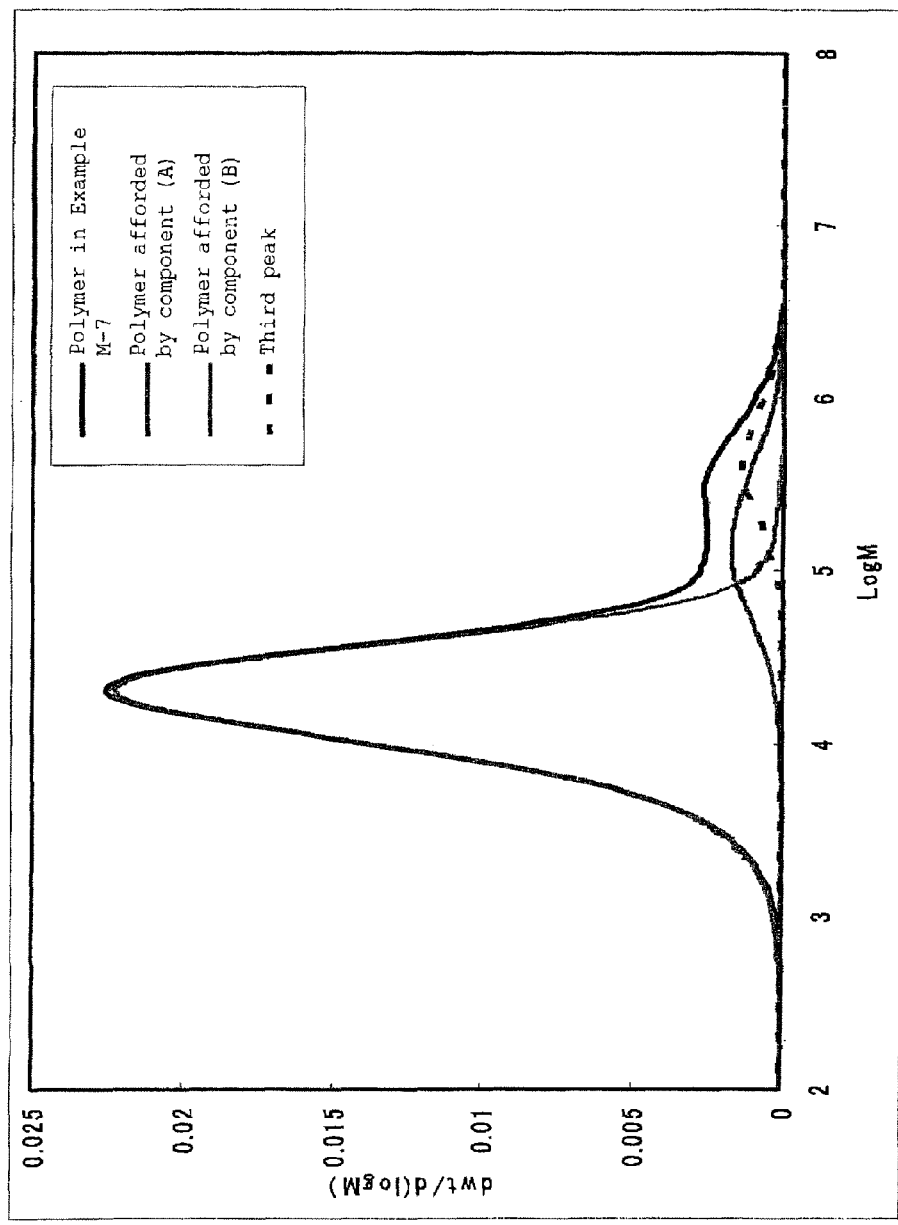
FIG. 5 is a GPC chart of a polymer obtained in Example M-7.

Polymerization was carried out in the same manner as in Example M-1, except that the solid catalyst component (Y-1) was replaced by 30 mg of the solid catalyst component (Y-3). The polymer obtained was dried under vacuum for 10 hours to afford 80.0 g of an ethylene/1-hexene copolymer. Results of GPC analysis and properties of the polymer are set forth in Table 4, and a GPC chart is shown in FIG. 5.

Example M-8

Polymerization

Polymerization was carried out in the same manner as in Example M-7, except that the ethylene gas was replaced by hydrogen/ethylene mixture gas (hydrogen concentration: 0.1 vol %). The polymer obtained was dried under vacuum for 10 hours to afford 84.7 g of an ethylene/1-hexene copolymer. Results of GPC analysis and properties of the polymer are set forth in Table 5.

Example M-9

Preparation of Solid Catalyst Component (Y-4)

A solid catalyst component (Y-4) was synthesized in the same manner as for the solid catalyst component (Y-1) in Example M-1, except that the metallocene compound (A2) was replaced by the metallocene compound (A6), and the reaction molar ratio of the metallocene compound (A6) and the metallocene compound (B1) was (A6)/(B1)=70/30 (molar ratio). After the reaction for 1 hour, Zr was not detected in the supernatant toluene. A portion of the heptane slurry of the solid catalyst component (Y-4) was sampled and the concentrations were determined, resulting in a Zr concentration of 0.038 mg/mL and an Al concentration of 2.1 mg/mL.

Polymerization

Figure 6:
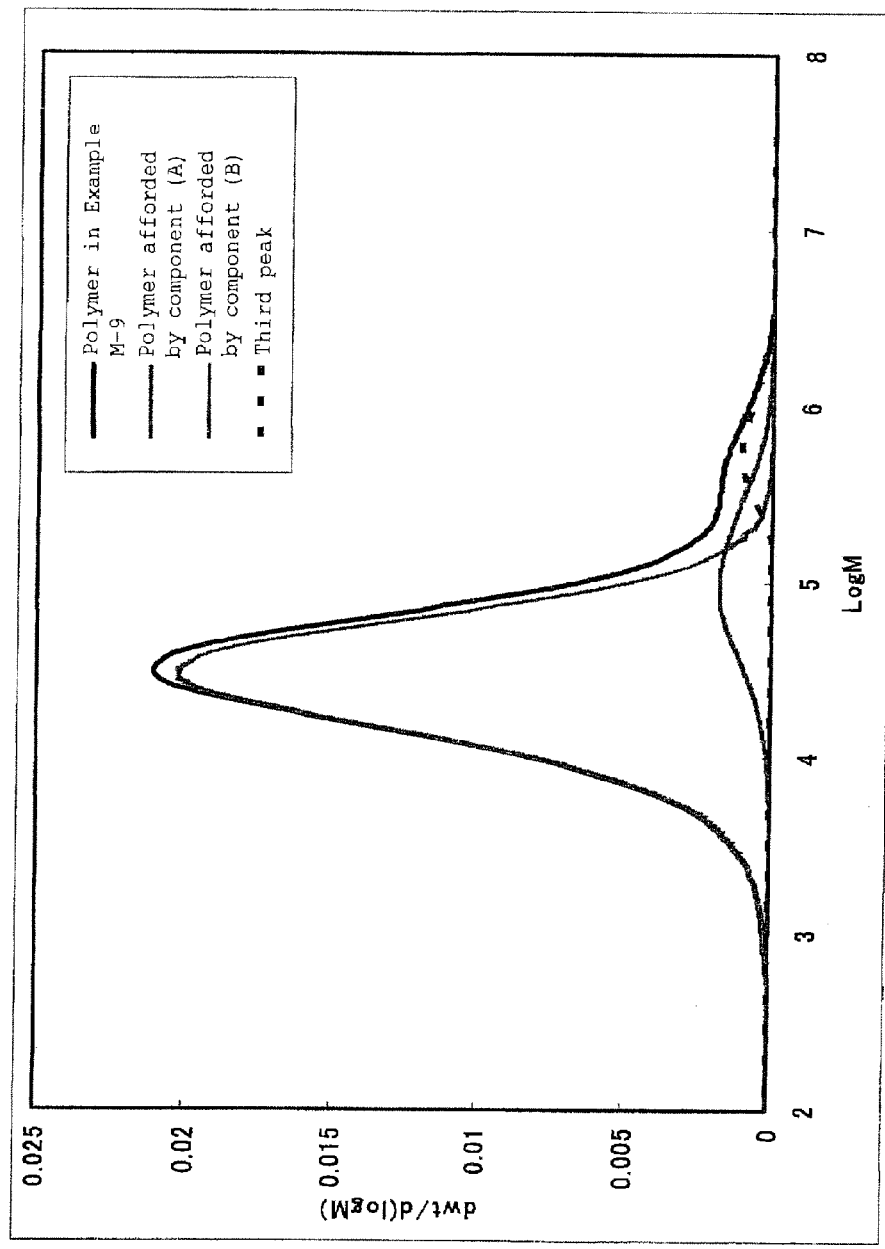
FIG. 6 is a GPC chart of a polymer obtained in Example M-9.

Polymerization was carried out in the same manner as in Example M-1, except that the solid catalyst component (Y-1) was replaced by the solid catalyst component (Y-4). The polymer obtained was dried under vacuum for 10 hours to afford 76.0 g of an ethylene/1-hexene copolymer. Results of GPC analysis and properties of the polymer are set forth in Table 5, and a GPC chart is shown in FIG. 6.

Example M-10

Polymerization

Polymerization was carried out in the same manner as in Example M-9, except that the ethylene gas was replaced by hydrogen/ethylene mixture gas (hydrogen concentration: 0.1 vol %). The polymer obtained was dried under vacuum for 10 hours to afford 80.3 g of an ethylene/1-hexene copolymer. Results of GPC analysis and properties of the polymer are set forth in Table 5.

Example M-11

Polymerization

Polymerization was carried out in the same manner as in Example M-3, except that the solid catalyst component (Y-1) was replaced by the solid catalyst component (Y-4). The polymer obtained was dried under vacuum for 10 hours to afford 51.6 g of an ethylene/1-butene copolymer. Results of GPC analysis and properties of the polymer are set forth in Table 5. Properties measured with respect to a sample of this polymer are indicated in Table 13.

Example M-12

Preparation of Solid Catalyst Component (Y-5)

A solid catalyst component (Y-5) was synthesized in the same manner as for the solid catalyst component (Y-1) in Example M-1, except that the reaction molar ratio of the metallocene compound (A2) and the metallocene compound (B1) was changed from (A2)/(B1)=60/40 (molar ratio) to (A2)/(B1)=45/55 (molar ratio). After the reaction for 1 hour, Zr was not detected in the supernatant toluene. A portion of the heptane slurry of the solid catalyst component (Y-5) was sampled and the concentrations were determined, resulting in a Zr concentration of 0.038 mg/mL and an Al concentration of 2.1 mg/mL.

Polymerization

Polymerization was carried out in the same manner as in Example M-3, except that the solid catalyst component (Y-1) was replaced by the solid catalyst component (Y-5) and the 1-butene/ethylene mixture gas (1-butene concentration: 4 vol %) was replaced by 1-butene/ethylene mixture gas (1-butene concentration: 7 vol %). The polymer obtained was dried under vacuum for 10 hours to afford 46.7 g of an ethylene/1-butene copolymer. Results of GPC analysis and properties of the polymer are set forth in Table 5. Properties measured with respect to a sample of this polymer are indicated in Table 13.

Example M-13

Polymerization

Polymerization was carried out in the same manner as in Example M-6, except that the 1-butene/ethylene mixture gas (1-butene concentration: 4 vol %) was replaced by 1-butene/ethylene mixture gas (1-butene concentration: 7 vol %). The polymer obtained was dried under vacuum for 10 hours to afford 51.9 g of an ethylene/1-butene copolymer. Results of GPC analysis and properties of the polymer are set forth in Table 5. Properties measured with respect to a sample of this polymer are indicated in Table 13.

Example M-14

Preparation of Solid Catalyst Component (Y-6)

A solid catalyst component (Y-6) was synthesized in the same manner as for the solid catalyst component (Y-2) in Example M-4, except that the metallocene compound (B1) was replaced by the metallocene compound (B2), and the reaction molar ratio of the metallocene compound (A3) and the metallocene compound (B2) was (A3)/(B2)=30/70 (molar ratio). After the reaction for 1 hour, Zr was not detected in the supernatant toluene. A portion of the heptane slurry of the solid catalyst component (Y-6) was sampled and the concentrations were determined, resulting in a Zr concentration of 0.036 mg/mL and an Al concentration of 2.3 mg/mL.

Polymerization

Polymerization was carried out in the same manner as in Example M-1, except that the solid catalyst component (Y-1) was replaced by the solid catalyst component (Y-6). The polymer obtained was dried under vacuum for 10 hours to afford 74.4 g of an ethylene/1-hexene copolymer. Results of GPC analysis and properties of the polymer are set forth in Table 5.

Example M-15

Preparation of Solid Catalyst Component (Y-7)

A solid catalyst component (Y-7) was synthesized in the same manner as for the solid catalyst component (Y-2) in Example M-4, except that the metallocene compound (B1) was replaced by the metallocene compound (B3), and the reaction molar ratio of the metallocene compound (A3) and the metallocene compound (B3) was (A3)/(B3)=70/30 (molar ratio). After the reaction for 1 hour, Zr was not detected in the supernatant toluene. A portion of the heptane slurry of the solid catalyst component (Y-7) was sampled and the concentrations were determined, resulting in a Zr concentration of 0.035 mg/mL and an Al concentration of 2.2 mg/mL.

Polymerization

Polymerization was carried out in the same manner as in Example M-1, except that the solid catalyst component (Y-1) was replaced by the solid catalyst component (Y-7). The polymer obtained was dried under vacuum for 10 hours to afford 121.3 g of an ethylene/1-hexene copolymer. Results of GPC analysis and properties of the polymer are set forth in Table 6.

Example M-16

Preparation of Solid Catalyst Component (Y-8)

A solid catalyst component (Y-8) was synthesized in the same manner as for the solid catalyst component (Y-2) in Example M-4, except that the metallocene compound (B1) was replaced by the metallocene compound (B4). After the reaction for 1 hour, Zr was not detected in the supernatant toluene. A portion of the heptane slurry of the solid catalyst component (Y-8) was sampled and the concentrations were determined, resulting in a Zr concentration of 0.034 mg/mL and an Al concentration of 2.3 mg/mL.

Polymerization

Polymerization was carried out in the same manner as in Example M-1, except that the solid catalyst component (Y-1) was replaced by the solid catalyst component (Y-8). The polymer obtained was dried under vacuum for 10 hours to afford 75.5 g of an ethylene/1-hexene copolymer. Results of GPC analysis and properties of the polymer are set forth in Table 6.

Example M-17

Preparation of Solid Catalyst Component (Y-9)

A solid catalyst component (Y-9) was synthesized in the same manner as for the solid catalyst component (Y-2) in Example M-4, except that the metallocene compound (B1) was replaced by the metallocene compound (B5), and the reaction molar ratio of the metallocene compound (A3) and the metallocene compound (B5) was (A3)/(B5)=55/45 (molar ratio). After the reaction for 1 hour, Zr was not detected in the supernatant toluene. A portion of the heptane slurry of the solid catalyst component (Y-9) was sampled and the concentrations were determined, resulting in a Zr concentration of 0.034 mg/mL and an Al concentration of 2.3 mg/mL.

Polymerization

Polymerization was carried out in the same manner as in Example M-1, except that the solid catalyst component (Y-1) was replaced by the solid catalyst component (Y-9). The polymer obtained was dried under vacuum for 10 hours to afford 113.7 g of an ethylene/1-hexene copolymer. Results of GPC analysis and properties of the polymer are set forth in Table 6.

Example M-18

Preparation of Solid Catalyst Component (Y-10)

A solid catalyst component (Y-10) was synthesized in the same manner as for the solid catalyst component (Y-2) in Example M-4, except that the metallocene compound (B1) was replaced by the metallocene compound (B6), and the reaction molar ratio of the metallocene compound (A3) and the metallocene compound (B6) was (A3)/(B6)=55/45 (molar ratio). After the reaction for 1 hour, Zr was not detected in the supernatant toluene. A portion of the heptane slurry of the solid catalyst component (Y-10) was sampled and the concentrations were determined, resulting in a Zr concentration of 0.036 mg/mL and an Al concentration of 2.3 mg/mL.

Polymerization

Polymerization was carried out in the same manner as in Example M-1, except that the solid catalyst component (Y-1) was replaced by the solid catalyst component (Y-10), and the polymerization temperature and the 1-hexene amount were changed from 80° C. and 10 mL to 70° C. and 30 mL. The polymer obtained was dried under vacuum for 10 hours to afford 116.0 g of an ethylene/1-hexene copolymer. Results of GPC analysis and properties of the polymer are set forth in Table 6.

Example M-19

Preparation of Solid Catalyst Component (X-11)

A 200 mL glass flask purged with nitrogen was charged with 50 mL of toluene, and the toluene slurry of the solid component (S) (1.0 g in terms of the solid component) was added thereto. Further, 12.7 mL of a toluene solution of the metallocene compound (B1) (0.002 mmol/mL in terms of Zr atom) was added dropwise. Reaction was performed at room temperature for 1 hour. After the reaction, the supernatant was removed by decantation. The residue was washed with heptane two times and was slurried into 100 mL of a heptane slurry (solid catalyst component X-11). A portion of the heptane slurry of the solid catalyst component (X-11) was sampled and the concentrations were determined, resulting in a Zr concentration of 0.023 mg/mL and an Al concentration of 1.3 mg/mL.

Polymerization

A 1 L SUS autoclave thoroughly purged with nitrogen was charged with 500 mL of purified heptane, and ethylene was passed through the autoclave to saturate the liquid phase and the gas phase with ethylene. Further, 10 mL of 1-hexene and 0.375 mmol of triisobutylaluminum were added, and 8 mg and 12 mg in terms of the solid component of the solid catalyst component (X-2) and the solid catalyst component (X-11), respectively, ((A2)/(B1) molar ratio=40/60) were added to the autoclave. The temperature was increased to 80° C., and polymerization was performed at 0.78 MPa·G for 90 minutes. The polymer obtained was dried under vacuum for 10 hours to afford 79.7 g of an ethylene/1-hexene copolymer. Results of GPC analysis and properties of the polymer are set forth in Table 6.

Example M-20

Polymerization

A 1 L SUS autoclave thoroughly purged with nitrogen was charged with 500 mL of purified heptane, and ethylene was passed through the autoclave to saturate the liquid phase and the gas phase with ethylene. Further, 10 mL of 1-hexene and 0.375 mmol of triisobutylaluminum were added, and 5 mg and 15 mg in terms of the solid component of the solid catalyst component (X-3) and the solid catalyst component (X-11), respectively, ((A3)/(B1) molar ratio=25/75) were added to the autoclave. The temperature was increased to 80° C., and polymerization was performed at 0.78 MPa·G for 90 minutes. The polymer obtained was dried under vacuum for 10 hours to afford 48.7 g of an ethylene/1-hexene copolymer. Results of GPC analysis and properties of the polymer are set forth in Table 6.

Example M-21

Preparation of Solid Catalyst Component (Y-11)

A 200 mL glass flask purged with nitrogen was charged with 50 mL of toluene, and the toluene slurry of the solid component (S) (1.0 g in terms of the solid component) prepared in Example L-11 was added thereto. Further, 5.6 mL of a toluene solution of the metallocene compound (dimethylsilylene (cyclopentadienyl)(3-n-propylcyclopentadienyl) zirconium dichloride (A2)) (0.002 mmol/mL in terms of Zr atom) and 7.1 mL of a toluene solution of the metallocene compound (B1) (0.002 mmol/mL in terms of Zr atom) were added dropwise as a mixture ((A2)/(B1) molar ratio=44/56). Reaction was performed at room temperature for 1 hour. After the reaction for 1 hour, Zr was not detected in the supernatant toluene. The supernatant was removed by decantation. The residue was washed with heptane two times and was slurried into 50 mL of a heptane slurry (solid catalyst component Y-11).

Preparation of Prepolymerized Catalyst Component (YP-11)

The heptane slurry of the solid catalyst component (Y-11) was cooled to 10° C. Under a stream of nitrogen, 2.0 mmol of diisobutylaluminum hydride (DiBAl—H) and 0.13 mL of 1-hexene were added. After the addition of 1-hexene, the supply of ethylene was initiated. The solid catalyst component was polymerized with a three-fold weight of ethylene relative to the solid catalyst component at a temperature of 35° C. (prepolymerization). The supernatant was removed by decantation. The solid catalyst component was washed with heptane three times and was slurried into 50 mL of a heptane slurry.

Subsequently, 10 mg of Chemistat 2500 (manufactured by Sanyo Chemical Industries, Ltd.) was added to the slurry, and the Chemistat 2500 was reacted with the prepolymerized catalyst component by keeping the temperature in the system at 34 to 36° C. for 1 hour. The supernatant was removed by decantation. The prepolymerized catalyst component was washed with hexane three times.

The hexane slurry was transferred to a 100 mL glass Schlenk flask, and hexane was distilled away under reduced pressure at 25° C. Thus, 4.0 g of a prepolymerized catalyst component (YP-11) was obtained which was polymerized with 3 g of the polymer per 1 g of the solid catalyst component.

The prepolymerized catalyst component (YP-11) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the prepolymerized catalyst component (YP-11). The polymer obtained was dried under vacuum for 10 hours to afford 64.3 g of an ethylene/1-hexene copolymer. Results of GPC analysis and properties of the polymer are set forth in Table 6.

Example M-22

Preparation of Solid Catalyst Component (Y-12)

A solid catalyst component (Y-12) was synthesized in the same manner as for the solid catalyst component (Y-11) in Example M-21, except that the reaction molar ratio of the metallocene compound (A2) and the metallocene compound (B1) was changed from (A2)/(B1)=44/56 (molar ratio) to (A2)/(B1)=47/53 (molar ratio). After the reaction for 1 hour, Zr was not detected in the supernatant toluene.

Preparation of Prepolymerized Catalyst Component (YP-12)

A solid catalyst component (YP-12) was prepared in the same manner as for the prepolymerized catalyst component (YP-11) in Example M-21, except that the solid catalyst component (Y-11) was replaced by the solid catalyst component (Y-12). The prepolymerized catalyst component (YP-12) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the solid catalyst component (YP-12). The polymer obtained was dried under vacuum for 10 hours to afford 81.9 g of an ethylene/1-hexene copolymer. Results of GPC analysis and properties of the polymer are set forth in Table 7.

Example M-23

Preparation of Solid Catalyst Component (Y-13)

A solid catalyst component (Y-13) was synthesized in the same manner as for the solid catalyst component (Y-11) in Example M-21, except that the metallocene compound (A2) was replaced by the metallocene compound (A3), and the reaction molar ratio of the metallocene compound (A3) and the metallocene compound (B1) was (A3)/(B1)=37/63 (molar ratio). After the reaction for 1 hour, Zr was not detected in the supernatant toluene.

Preparation of Prepolymerized Catalyst Component (YP-13)

A solid catalyst component (YP-13) was prepared in the same manner as for the prepolymerized catalyst component (YP-11) in Example M-21, except that the solid catalyst component (Y-11) was replaced by the solid catalyst component (Y-13). The prepolymerized catalyst component (YP-13) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the solid catalyst component (YP-13). The polymer obtained was dried under vacuum for 10 hours to afford 59.6 g of an ethylene/1-hexene copolymer. Results of GPC analysis and properties of the polymer are set forth in Table 7.

Example M-24

Preparation of Solid Catalyst Component (Y-14)

A solid catalyst component (Y-14) was synthesized in the same manner as for the solid catalyst component (Y-13) in Example M-23, except that the reaction molar ratio of the metallocene compound (A3) and the metallocene compound (B1) was changed from (A3)/(B1)=37/63 (molar ratio) to (A3)/(B1)=45/55 (molar ratio). After the reaction for 1 hour, Zr was not detected in the supernatant toluene.

Preparation of Prepolymerized Catalyst Component (YP-14)

A solid catalyst component (YP-14) was prepared in the same manner as for the prepolymerized catalyst component (YP-11) in Example M-21, except that the solid catalyst component (Y-11) was replaced by the solid catalyst component (Y-14). The prepolymerized catalyst component (YP-14) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the solid catalyst component (YP-14). The polymer obtained was dried under vacuum for 10 hours to afford 80.3 g of an ethylene/1-hexene copolymer. Results of GPC analysis and properties of the polymer are set forth in Table 7.

Example M-25

Preparation of Solid Catalyst Component (Y-15)

A solid catalyst component (Y-15) was synthesized in the same manner as for the solid catalyst component (Y-13) in Example M-23, except that the reaction molar ratio of the metallocene compound (A3) and the metallocene compound (B1) was changed from (A3)/(B1)=37/63 (molar ratio) to (A3)/(B1)=49/51 (molar ratio). After the reaction for 1 hour, Zr was not detected in the supernatant toluene.

Preparation of Prepolymerized Catalyst Component (YP-15)

A solid catalyst component (YP-15) was prepared in the same manner as for the prepolymerized catalyst component (YP-11) in Example M-21, except that the solid catalyst component (Y-11) was replaced by the solid catalyst component (Y-15). The prepolymerized catalyst component (YP-15) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the solid catalyst component (YP-15). The polymer obtained was dried under vacuum for 10 hours to afford 94.1 g of an ethylene/1-hexene copolymer. Results of GPC analysis and properties of the polymer are set forth in Table 7.

Example M-26

Preparation of Solid Catalyst Component (Y-16)

A solid catalyst component (Y-16) was synthesized in the same manner as for the solid catalyst component (Y-13) in Example M-23, except that the reaction molar ratio of the metallocene compound (A3) and the metallocene compound (B1) was changed from (A3)/(B1)=37/63 (molar ratio) to (A3)/(B1)=55/45 (molar ratio). After the reaction for 1 hour, Zr was not detected in the supernatant toluene.

Preparation of Prepolymerized Catalyst Component (YP-16)

A solid catalyst component (YP-16) was prepared in the same manner as for the prepolymerized catalyst component (YP-11) in Example M-21, except that the solid catalyst component (Y-11) was replaced by the solid catalyst component (Y-16). The prepolymerized catalyst component (YP-16) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the prepolymerized catalyst component (YP-16). The polymer obtained was dried under vacuum for 10 hours to afford 63.6 g of an ethylene/1-hexene copolymer. Results of GPC analysis and properties of the polymer are set forth in Table 7.

Example M-27

Preparation of Prepolymerized Catalyst Component (YP-17)

A prepolymerized catalyst component (YP-17) was prepared in the same manner as for the prepolymerized catalyst component (YP-11) in Example M-21, except that the amount of the Chemistat 2500 was increased from 10 mg to 40 mg. The prepolymerized catalyst component (YP-17) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the prepolymerized catalyst component (YP-17). The polymer obtained was dried under vacuum for 10 hours to afford 59.6 g of an ethylene/1-hexene copolymer. Results of GPC analysis and properties of the polymer are set forth in Table 8.

Example M-28

Preparation of Solid Catalyst Component (Y-18)

A 200 mL glass flask purged with nitrogen was charged with 50 mL of toluene, and the toluene slurry of the solid component (S) (1.0 g in terms of the solid component) prepared in Example L-11 was added thereto. Further, 5.3 mL of a toluene solution of the metallocene compound (dimethylsilylene (cyclopentadienyl)(3-n-propylcyclopentadienyl) zirconium dichloride (A2)) (0.002 mmol/mL in terms of Zr atom) and 7.4 mL of a toluene solution of the metallocene compound (B-1) (0.002 mmol/mL in terms of Zr atom) were added dropwise as a mixture ((A2)/(B1) molar ratio=42/58) at room temperature. After the dropwise addition, the temperature was increased to 75° C. Reaction was performed at 75° C. for 2 hours. The reaction product was washed with heptane two times and was slurried into 50 mL of a heptane slurry (solid catalyst component Y-18). After the reaction for 2 hours, Zr was not detected in the supernatant toluene.

Preparation of Prepolymerized Catalyst Component (YP-18)

The heptane slurry of the solid catalyst component (Y-18) was cooled to 10° C. Under a stream of nitrogen, 10 mg of Chemistat 2500 was added, and reaction was performed for 5 minutes. Subsequently, 2.0 mmol of diisobutylaluminum hydride (DiBAl—H) and 0.13 mL of 1-hexene were added in this order. After the addition of 1-hexene, the supply of ethylene was initiated. The solid catalyst component was polymerized with a three-fold weight of ethylene relative to the solid catalyst component at a temperature of 35° C. (prepolymerization). The supernatant was removed by decantation. The solid catalyst component was washed with heptane three times and was slurried into 50 mL of a heptane slurry.

Subsequently, 40 mg of Chemistat 2500 was added to the slurry, and the Chemistat 2500 was reacted with the prepolymerized catalyst component by keeping the temperature in the system at 34 to 36° C. for 1 hour. The supernatant was removed by decantation. The prepolymerized catalyst component was washed with hexane three times.

The hexane slurry was transferred to a 100 mL glass Schlenk flask, and hexane was distilled away under reduced pressure at 25° C. Thus, 4.0 g of a prepolymerized catalyst component (YP-18) was obtained which was polymerized with 3 g of the polymer per 1 g of the solid catalyst component.

The prepolymerized catalyst component (YP-18) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the prepolymerized catalyst component (YP-18). The polymer obtained was dried under vacuum for 10 hours to afford 102.2 g of an ethylene/1-hexene copolymer. Results of GPC analysis and properties of the polymer are set forth in Table 8.

Example M-29

Preparation of Solid Catalyst Component (Y-19)

A solid catalyst component (Y-19) was synthesized in the same manner as for the solid catalyst component (Y-18) in Example M-28, except that the reaction molar ratio of the metallocene compound (A2) and the metallocene compound (B1) was changed from (A2)/(B1)=42/58 (molar ratio) to a reaction molar ratio of the metallocene compound (A2) and the metallocene compound (B1) of (A2)/(B1)=24/76 (molar ratio). After the reaction for 1 hour, Zr was not detected in the supernatant toluene[0501]

Preparation of Prepolymerized Catalyst Component (YP-19)

A solid catalyst component (YP-19) was prepared in the same manner as for the prepolymerized catalyst component (YP-11) in Example M-21, except that the solid catalyst component (Y-11) was replaced by the solid catalyst component (Y-19). The prepolymerized catalyst component (YP-19) was analyzed for composition and was found to contain 0.50 mg of Zr atom per 1 g of the solid catalyst component.

Polymerization

Polymerization was carried out in the same manner as in Example M-1, except that the solid catalyst component (Y-1) was replaced by the solid catalyst component (YP-19). The polymer obtained was dried under vacuum for 10 hours to afford 75.9 g of an ethylene/1-hexene copolymer. Results of GPC analysis and properties of the polymer are set forth in Table 8.

Example M-30

Polymerization

Polymerization was carried out in the same manner as in Example M-1, except that the solid catalyst component (Y-1) was replaced by the prepolymerized catalyst component (YP-11) and the polymerization temperature was changed from 80° C. to 70° C. The polymer obtained was dried under vacuum for 10 hours to afford 59.1 g of an ethylene/1-hexene copolymer. Results of GPC analysis and properties of the polymer are set forth in Table 8.

Example M-31

Polymerization

A 1 L SUS autoclave thoroughly purged with nitrogen was charged with 500 mL of purified heptane, and ethylene was passed through the autoclave to saturate the liquid phase and the gas phase with ethylene. Further, 10 mL of 1-hexene and 0.375 mmol of triisobutylaluminum were added in this order, and 35 mg in terms of the solid catalyst component of the prepolymerized catalyst component (YP-19) was further added to the autoclave. Subsequently, 1.7 mg of Chemistat 2500 was added. The temperature was increased to 80° C., and polymerization was performed at 0.78 MPa·G for 90 minutes. The polymer obtained was dried under vacuum for 10 hours to afford 49.3 g of an ethylene/1-hexene copolymer. Results of GPC analysis and properties of the polymer are set forth in Table 8.

Example M-32

Polymerization Polymerization was carried out in the same manner as in

Example M-31, except that 1.7 mg of Chemistat 2500 was replaced by 3.3 mg of PLURONIC L71 (manufactured by ADEKA CORPORATION). The polymer obtained was dried under vacuum for 10 hours to afford 52.6 g of an ethylene/1-hexene copolymer. Results of GPC analysis and properties of the polymer are set forth in Table 8.

Comparative Example M-1

Preparation of Solid Catalyst Component (EY-1)

A solid catalyst component (EY-1) was synthesized in the same manner as for the solid catalyst component (Y-2) in Example M-4, except that the metallocene compound (A3) was replaced by the metallocene compound (E1), and the reaction molar ratio of the metallocene compound (E1) and the metallocene compound (B2) was (E1)/(B2)=80/20 (molar ratio). After the reaction for 1 hour, Zr was not detected in the supernatant toluene. A portion of the heptane slurry of the solid catalyst component (EY-1) was sampled and the concentrations were determined, resulting in a Zr concentration of 0.037 mg/mL and an Al concentration of 2.3 mg/mL.

Polymerization

Polymerization was carried out in the same manner as in Example M-1, except that the solid catalyst component (Y-1) was replaced by the solid catalyst component (EY-1), and the ethylene gas was replaced by hydrogen/ethylene mixture gas (hydrogen concentration: 0.45 vol %). The polymer obtained was dried under vacuum for 10 hours to afford 87.4 g of an ethylene/1-hexene copolymer. Results of GPC analysis and properties of the polymer are set forth in Table 9.

The olefin polymerization catalysts according to the present invention, in comparison with Comparative Example M-1, were demonstrated to afford the ethylene polymers claimed in the invention with high productivity. This result was because the metallocene compounds (the components A) used in the invention afforded polymers having a low molecular weight and a large number of terminal vinyl bonds with high catalytic activity.

Comparative Example M-2

Preparation of Solid Catalyst Component (EY-2)

A solid catalyst component (EY-2) was synthesized in the same manner as for the solid catalyst component (Y-2) in Example M-4, except that the metallocene compound (A3) was replaced by the metallocene compound (E5), and the reaction molar ratio of the metallocene compound (E5) and the metallocene compound (B2) was (E5)/(B2)=35/65 (molar ratio). After the reaction for 1 hour, Zr was not detected in the supernatant toluene. A portion of the heptane slurry of the solid catalyst component (EY-2) was sampled and the concentrations were determined, resulting in a Zr concentration of 0.033 mg/mL and an Al concentration of 2.1 mg/mL.

Polymerization

Polymerization was carried out in the same manner as in Example M-1, except that the solid catalyst component (Y-1) was replaced by the solid catalyst component (EY-2), and the ethylene gas was replaced by hydrogen/ethylene mixture gas (hydrogen concentration: 0.65 vol %). The polymer obtained was dried under vacuum for 10 hours to afford 47.9 g of an ethylene/1-hexene copolymer. Results of GPC analysis and properties of the polymer are set forth in Table 9.

The polymer obtained in Comparative Example M-2 substantially did not have long-chain branches and did not meet the preferred requirement for the ethylene polymers produced according to the processes of the invention. This result was because metallocene compounds such as that used in Comparative Example M-2 having substituent groups on both the cyclopentadienyl rings afforded polymers having a high molecular weight and a small number of terminal vinyl bonds.

Comparative Example M-3

Preparation of Solid Catalyst Component (EY-3)

A solid catalyst component (EY-3) was synthesized in the same manner as for the solid catalyst component (Y-2) in Example M-4, except that the metallocene compound (A3) was replaced by the metallocene compound (E2), and the reaction molar ratio of the metallocene compound (E2) and the metallocene compound (B2) was (E2)/(B2)=10/90 (molar ratio). After the reaction for 1 hour, Zr was not detected in the supernatant toluene. A portion of the heptane slurry of the solid catalyst component (EY-3) was sampled and the concentrations were determined, resulting in a Zr concentration of 0.030 mg/mL and an Al concentration of 2.4 mg/mL.
[0513]

Polymerization

Polymerization was carried out in the same manner as in Example M-1, except that the solid catalyst component (Y-1) was replaced by the solid catalyst component (EY-3). The polymer obtained was dried under vacuum for 10 hours to afford 77.8 g of an ethylene/1-hexene copolymer. Results of GPC analysis and properties of the polymer are set forth in Table 9.

Comparative Example M-4

Preparation of Solid Catalyst Component (EY-4)

A solid catalyst component (EY-4) was synthesized in the same manner as for the solid catalyst component (Y-1) in Example M-1, except that the metallocene compound (A2) was replaced by the metallocene compound (E2), and the reaction molar ratio of the metallocene compound (E2) and the metallocene compound (B1) was (E2)/(B1)=30/70 (molar ratio). After the reaction for 1 hour, Zr was not detected in the supernatant toluene. A portion of the heptane slurry of the solid catalyst component (EY-4) was sampled and the concentrations were determined, resulting in a Zr concentration of 0.035 mg/mL and an Al concentration of 2.0 mg/mL.

Polymerization

Polymerization was carried out in the same manner as in Example M-1, except that the solid catalyst component (Y-1) was replaced by the solid catalyst component (EY-4). The polymer obtained was dried under vacuum for 10 hours to afford 91.6 g of an ethylene/1-hexene copolymer. Results of GPC analysis and properties of the polymer are set forth in Table 9.

From the comparison with Comparative Examples M-3 and M-4, the olefin polymerization catalysts according to the present invention were demonstrated to afford more preferred ethylene polymers (for example, having properties 1 and 2) than produced with the catalysts used in Comparative Examples M-3 and M-4. This result was because the metallocene compounds (the components A) used in the invention afforded polymers having a lower molecular weight and a larger number of terminal vinyl bonds with higher catalytic activity than the metallocene compound (E2) used in Comparative Examples M-3 and M-4 which had substituent groups on both the cyclopentadienyl rings.

Preparation of Prepolymerized Catalyst Components

Preparation of Solid Catalyst Component (Y-20)

A 150 L reactor equipped with a stirrer was charged in a nitrogen atmosphere with 50.1 L of toluene, and the toluene slurry of the solid component (S) (1265 g in terms of the solid component) prepared in Example L-11 was added thereto. Separately, 5.72 g of the metallocene compound (A2) (14.65 mmol in terms of Zr atom) and 9.00 g of the metallocene compound (B1) (16.52 mmol in terms of Zr atom) ((A2)/(B1) molar ratio=47/53) were placed in a 2 L glass reactor in a nitrogen atmosphere. The compounds were dissolved in 2.0 L of toluene, and the solution was injected to the above reactor. After the injection, reaction was performed at an inside temperature of 20 to 25° C. for 1 hour. The supernatant was removed by decantation. The solid catalyst component obtained was washed with hexane two times, and hexane was added thereto to a total volume of 50 L, thereby preparing a hexane slurry of the solid catalyst component (Y-20).

Preparation of Prepolymerized Catalyst Component (YP-20)

The hexane slurry of the solid catalyst component (Y-20) was cooled to 10.0° C. Ethylene was continuously supplied to the system under atmospheric pressure for several minutes. During the supply, the temperature in the system was maintained at 10 to 15° C. Subsequently, 2.7 mol of diisobutylaluminum hydride (DiBAl—H) and 84 mL of 1-hexene were added. After the addition of 1-hexene, the supply of ethylene was initiated at 1.82 kg/hour and prepolymerization was carried out at 32 to 37° C. in the system. After 58 minutes from the initiation of the prepolymerization, 43.0 mL of 1-hexene was added. Another 43.0 mL of 1-hexene was added after the passage of 111 minutes. After 153 minutes from the initiation of the prepolymerization, the ethylene supply was terminated at a total supply of 3827 g. The supernatant was removed by decantation. The solid catalyst component was washed with hexane three times, and hexane was added thereto to a total volume of 66 L.

Subsequently, a hexane solution of Chemistat 2500 (13.1 g) was injected at a temperature in the system of 34 to 36° C., and the temperature was maintained at 34 to 36° C. for 1 hour to cause the Chemistat 2500 to be supported on the prepolymerized catalyst component. The supernatant was removed by decantation. The prepolymerized catalyst component was washed with hexane four times.

Thereafter, 25 L of the hexane slurry of the prepolymerized catalyst component (5269 g in terms of the prepolymerized solid catalyst component) was transferred to a 43 L evaporator equipped with a stirrer in a nitrogen atmosphere. After the transfer, the evaporator was evacuated to −65 kPaG in about 3.5 hours. After the pressure reached −65 kPaG, the slurry was dried under vacuum for about 4.0 hours to remove hexane and volatile components of the prepolymerized catalyst component. The evaporator was further evacuated to −100 kPaG. After the pressure reached −100 kPaG, the component was dried under vacuum for 6 hours. Thus, a prepolymerized catalyst component (YP-20) was obtained which was polymerized with 3 g of the polymer per 1 g of the solid catalyst component.

A portion of the prepolymerized catalyst component was dried and analyzed for composition and was found to contain 0.50 mg of Zr atom per 1 g of the solid catalyst component.

Preparation of Solid Catalyst Component (Y-21)

A hexane slurry of a solid catalyst component (Y-21) was synthesized in the same manner as for the solid catalyst component (Y-20), except that the reaction ratio of the metallocene compound (A2) and the metallocene compound (B1) was changed from (A2)/(B1)=47/53 (molar ratio) to (A2)/(B1)=42/58 (molar ratio).

Preparation of Prepolymerized Catalyst Component (YP-21)

A prepolymerized catalyst component (YP-21) was obtained in the same manner as for the prepolymerized catalyst component (YP-20), except that the solid catalyst component (Y-20) was replaced by the solid catalyst component (Y-21). The prepolymerized catalyst component was analyzed for composition and was found to contain 0.50 mg of Zr atom per 1 g of the solid catalyst component.

Preparation of Solid Catalyst Component (Y-22)

A hexane slurry of a solid catalyst component (Y-22) was synthesized in the same manner as for the solid catalyst component (Y-20), except that the reaction ratio of the metallocene compound (A2) and the metallocene compound (B1) was changed from (A2)/(B1)=47/53 (molar ratio) to (A2)/(B1)=39/61 (molar ratio).

Preparation of Prepolymerized Catalyst Component (YP-22)

A prepolymerized catalyst component (YP-22) was obtained in the same manner as for the prepolymerized catalyst component (YP-20), except that the solid catalyst component (Y-20) was replaced by the solid catalyst component (Y-22). The prepolymerized catalyst component was analyzed for composition and was found to contain 0.50 mg of Zr atom per 1 g of the solid catalyst component.

Preparation of Solid Catalyst Component (Y-23)

A hexane slurry of a solid catalyst component (Y-23) was synthesized in the same manner as for the solid catalyst component (Y-20), except that the metallocene compound (A2) was replaced by the metallocene compound (A3), and the reaction ratio of the metallocene compound (A3) and the metallocene compound (B1) was (A3)/(B1)=45/55 (molar ratio).

Preparation of Prepolymerized Catalyst Component (YP-23)

A prepolymerized catalyst component (YP-23) was obtained in the same manner as for the prepolymerized catalyst component (YP-20), except that the solid catalyst component (Y-20) was replaced by the solid catalyst component (Y-23). The prepolymerized catalyst component was analyzed for composition and was found to contain 0.50 mg of Zr atom per 1 g of the solid catalyst component.

Preparation of Solid Catalyst Component (Y-24)

A hexane slurry of a solid catalyst component (Y-24) was synthesized in the same manner as for the solid catalyst component (Y-23), except that the reaction ratio of the metallocene compound (A3) and the metallocene compound (B1) was changed from (A3)/(B1)=45/55 (molar ratio) to (A3)/(B1)=40/60 (molar ratio).

Preparation of Prepolymerized Catalyst Component (YP-24)

A prepolymerized catalyst component (YP-24) was obtained in the same manner as for the prepolymerized catalyst component (YP-20), except that the solid catalyst component (Y-20) was replaced by the solid catalyst component (Y-24). The prepolymerized catalyst component was analyzed for composition and was found to contain 0.50 mg of Zr atom per 1 g of the solid catalyst component.

Preparation of Solid Catalyst Component (Y-25)

A 150 L reactor equipped with a stirrer was charged in a nitrogen atmosphere with toluene and the toluene slurry of the solid component (S) (1575 g in terms of the solid component) prepared in Example L-11. The total volume was adjusted to 33 L. Separately, 3.58 g of the metallocene compound (A2) (9.18 mmol in terms of Zr atom) and 15.83 g of the metallocene compound (B1) (29.06 mmol in terms of Zr atom) ((A-2)/(B-1) molar ratio=24/76) were placed in a 2 L glass reactor in a nitrogen atmosphere. The compounds were dissolved in 2.0 L of toluene, and the solution was injected to the above reactor. After the injection, reaction was performed at an inside temperature of 73 to 76° C. for 2 hours. The supernatant was removed by decantation. The solid catalyst component obtained was washed with hexane three times, and hexane was added thereto to a total volume of 25 L, thereby preparing a hexane slurry of the solid catalyst component (Y-25).

Preparation of Prepolymerized Catalyst Component (YP-25)

The hexane slurry of the solid catalyst component (Y-25) was cooled to 10.8° C. A hexane solution of Chemistat 2500 (15.9 g) was injected to the reactor, and 1.4 mol of diisobutylaluminum hydride (DiBAl—H) was added. Ethylene was continuously supplied to the system under atmospheric pressure for several minutes. During the supply, the temperature in the system was maintained at 10 to 15° C. Subsequently, 103 mL of 1-hexene was added. After the addition of 1-hexene, the supply of ethylene was initiated at 1.5 kg/hour and prepolymerization was carried out at 32 to 37° C. in the system. After 85 minutes from the initiation of the prepolymerization, 52 mL of 1-hexene was added. Another 52 mL of 1-hexene was added after the passage of 155 minutes. After 217 minutes from the initiation of the prepolymerization, the ethylene supply was terminated at a total supply of 4643 g. The supernatant was removed by decantation. The solid catalyst component was washed with hexane four times, and hexane was added thereto to a total volume of 25 L.

Subsequently, a hexane solution of Chemistat 2500 (63.8 g) was injected at a temperature in the system of 34 to 36° C., and the temperature was maintained at 34 to 36° C. for 2 hours to cause the Chemistat 2500 to be supported on the prepolymerized catalyst component. The supernatant was removed by decantation. The prepolymerized catalyst component was washed with hexane four times.

Thereafter, 25 L of the hexane slurry of the prepolymerized catalyst component (6456 g in terms of the prepolymerized solid catalyst component) was transferred to a 43 L evaporator equipped with a stirrer in a nitrogen atmosphere. After the transfer, the evaporator was evacuated to −68 kPaG in about 60 minutes. After the pressure reached −68 kPaG, the slurry was dried under vacuum for about 4.3 hours to remove hexane and volatile components of the prepolymerized catalyst component. The evaporator was further evacuated to −100 kPaG. After the pressure reached −100 kPaG, the component was dried under vacuum for 8 hours. Thus, a prepolymerized catalyst component (YP-25) was obtained which was polymerized with 3 g of the polymer per 1 g of the solid catalyst component.

A portion of the prepolymerized catalyst component was dried and analyzed for composition and was found to contain 0.5 mg of Zr atom per 1 g of the solid catalyst component.

Examples M-33 to M-46

Polymerization

Ethylene polymers were produced in a 1.7 m3 fluidized-bed gas-phase polymerizer using the prepolymerized catalyst components (YP-20 to YP-25).

The prepolymerized catalyst component was continuously supplied to the reactor, and copolymerization was carried out at a total pressure of 2.0 MPa·G, an ethylene partial pressure of 1.2 MPa·A, a gas linear velocity of 0.8 m/sec in the reactor, and a polymerization temperature of 80° C. The gas composition was maintained constant by continuously supplying nitrogen, ethylene, and 1-butene or 1-hexene. The supply amounts of the prepolymerized catalyst component and the gas are described in Tables 10 to 12. The ethylene polymer was continuously withdrawn from the polymerizer and was dried in a drying apparatus.

To the ethylene polymer, 0.1 wt % of IRGANOX 1076 (manufactured by Ciba Specialty Chemicals, Inc.) and 0.1 wt % of IRGAFOS 168 (manufactured by Ciba Specialty Chemicals, Inc.) were added as heat stabilizers. The mixture was melt-kneaded in a single-screw 65 mm-diameter extruder (Placo Co., Ltd.) at a preset temperature of 180° C. and a screw rotation of 50 rpm and was extruded into a strand. The strand was pelletized with a cutter to give specimens. The results of properties measurement of the specimens from Examples 33 and 34 (comonomer: 1-butene) are set forth in Table 13, and the results of extrusion lamination are shown in Table 14. The results of properties measurement of the specimens from Examples 33 and 34 (comonomer: 1-butene) are set forth in Tables 15 and 16, and the results of extrusion lamination are shown in Table 17.

Comparative Example M-5

Pellets of ethylene/4-methyl-1-pentene copolymer obtained by solution polymerization, purchased from Prime Polymer Co., Ltd. (ULTZEX 20100J), were used as a specimen for properties evaluation and extrusion lamination. The results are set forth in Tables 18 and 19.

Comparative Example M-5 resulted in large neck-in and a smaller MT/η* ratio than Examples.

Comparative Example M-6

Preparation of Solid Catalyst Component (EY-5)

A 114 L reactor equipped with a stirrer was charged in a nitrogen atmosphere with the toluene slurry of the solid component (S) (1000 g in terms of the solid component). With stirring, 14.7 L of a toluene solution of ethylenebis(indenyl) zirconium dichloride (0.0017 mmol/mL in terms of Zr atom) was added dropwise at 78 to 80° C. over a period of 30 minutes. Reaction was performed at the temperature for 2 hours. The supernatant was removed. The solid catalyst component obtained was washed with hexane two times, and hexane was added thereto to a total volume of 25 L, thereby preparing a hexane slurry of the solid catalyst component (EY-5).

Preparation of Prepolymerized Catalyst Component (EYP-5)

The hexane slurry of the solid catalyst component (EY-5) was cooled to 5° C. Ethylene was continuously supplied to the system under atmospheric pressure. During the supply, the temperature in the system was maintained at 10 to 15° C. Subsequently, 1.9 L of a hexane solution of triisobutylaluminum (40.0 mmol/L in terms of Al atom) and 65.3 mL of 1-hexene were added, thereby initiating prepolymerization. The temperature in the system was increased to 35° C. in 1 hour and was thereafter maintained at 34 to 35° C. After 70 minutes from the initiation of the prepolymerization, 65.3 mL of 1-hexene was added.

After 4 hours from the initiation of the prepolymerization, the system was purged with nitrogen and the prepolymerization was terminated. The supernatant was removed. The catalyst component was washed with hexane four times. Thus, a prepolymerized catalyst component was obtained which was polymerized with 3 g of the polymer per 1 g of the solid catalyst component. Thereafter, the temperature in the system was increased to 34 to 35° C., and 10 L of a hexane solution of EMULGEN 108 (polyoxyethylene lauryl ether, manufactured by Kao Corporation) (EMULGEN concentration: 1.0 g/L) was added. The system was stirred at the temperature for 2 hours, and a prepolymerized catalyst component (EYP-5) was obtained in which EMULGEN was supported on the prepolymerized catalyst component.

Polymerization

In a continuous fluidized-bed gas-phase polymerizer, ethylene and 1-hexene were copolymerized at a total pressure of 2.0 MPa-G, a polymerization temperature of 70° C., and a gas linear velocity of 0.8 m/sec. The prepolymerized catalyst component (EYP-5) prepared above was dried and was continuously supplied at a rate of 25 to 30 g/hour. During the polymerization, the gas composition was maintained constant by continuously supplying ethylene, 1-hexene, hydrogen and nitrogen (gas composition: 1-hexene/ethylene=1.1-1.3×10$^{-2}$, ethylene concentration=71.4%). The yield of the ethylene polymer was 5.3 kg/hour.

The ethylene polymer obtained was formulated into specimens in the same manner as in Example M-33. The specimens were used for properties evaluation and extrusion lamination. The results are set forth in Tables 18 and 19.

Comparative Example M-6 resulted in large neck-in and a small MT/η* ratio. The polymer caused take-up surge, and the zero-shear viscosity ($\eta_0$) did not meet Equation (Eq-1).

Comparative Example M-7

Pellets of ethylene/1-octene copolymer obtained by solution polymerization, purchased from The Dow Chemical Company (AFFINITY PF1140), were used as a specimen for properties evaluation. The results are set forth in Table 18.

Comparative Example M-7 resulted in a small MT/η* ratio, and the zero-shear viscosity ($\eta_0$) did not meet Equation (Eq-1). Based on these results, the polymer was assumed to cause large neck-in and take-up surge.

Comparative Example M-8

Preparation of Solid Component (S2)

In a 260 L reactor equipped with a stirrer, 10 kg of silica ($SiO_2$:average particle diameter:12 μm) that had been dried at 250° C. for 10 hours was suspended in 90.5 L of toluene in a nitrogen atmosphere. The suspension was cooled to 0 to 5° C. A toluene solution of methylalumoxane (3.0 mmol/mL in terms of Al atom) in a volume of 45.5 L was added dropwise to the suspension over a period of 30 minutes. During the dropwise addition, the temperature in the system was maintained at 0 to 5° C. After the dropwise addition, the reaction was continuously performed at 0 to 5° C. for 30 minutes. Thereafter, the temperature was increased to 95 to 100° C. in about 1.5 hours, and the reaction was conducted at 95 to 100° C. for 4 hours. The temperature was then lowered to ambient, and the supernatant was removed by decantation. The solid component thus obtained was washed with toluene two times, and toluene was added thereto to a total volume of 129 L, thereby preparing a toluene slurry of the solid component (S2). A portion of the solid component was sampled and the concentrations were determined, resulting in a slurry concentration of 137.5 g/L and an Al concentration of 1.1 mol/L.

Preparation of Solid Catalyst Component (EY-6)

A 114 L reactor equipped with a stirrer was charged in a nitrogen atmosphere with 21.0 L of toluene and 15.8 L of the toluene slurry of the solid component (S2) (2400 g in terms of the solid component). Separately, a 100 L reactor equipped with a stirrer was charged in a nitrogen atmosphere with 31.0 L of toluene. With stirring, 10.0 L of a toluene solution of the metallocene compound (E1) (8.25 mmol/L in terms of Zr atom) was added and subsequently 2.0 L of a toluene solution of the metallocene compound (B2) (2.17 mmol/L in terms of Zr atom) was added, followed by mixing for several minutes ((E1)/(B2) molar ratio=95/5). The mixture solution thus prepared was injected to the reactor containing the toluene slurry of the solid component (S2). After the injection, reaction was performed at an inside temperature of 20 to 25° C. for 1 hour. The supernatant was removed by decantation. The solid catalyst component thus obtained was washed with hexane three times, and hexane was added thereto to a total volume of 56 L. Thus, a hexane slurry of the solid catalyst component (EY-6) was prepared.

Preparation of Prepolymerized Catalyst Component (EYP-6)

The hexane slurry of the solid catalyst component (EY-6) was cooled to 10° C. Ethylene was continuously supplied to the system under atmospheric pressure for several minutes. During the supply, the temperature in the system was maintained at 10 to 15° C. Subsequently, 2.8 mol of triisobutylaluminum (TiBAl) and 157 mL of 1-hexene were added. After the addition of 1-hexene, the supply of ethylene was initiated at 1.8 kg/hour and prepolymerization was initiated. The temperature in the system was increased to 24° C. in 40 minutes after the initiation of the prepolymerization, and was thereafter maintained at 24 to 26° C. After 70 minutes from the initiation of the prepolymerization, 79.0 mL of 1-hexene was added. Another 79.0 mL of 1-hexene was added after the passage of 140 minutes.

After 220 minutes from the initiation of the prepolymerization, the ethylene supply was terminated. The system was purged with nitrogen, and the prepolymerization was terminated. The supernatant was removed by decantation. The prepolymerized catalyst component was washed with hexane six times, and a prepolymerized catalyst component (EYP-6) was obtained which was polymerized with 2.87 g of the polymer per 1 g of the solid catalyst component.

A portion of the prepolymerized catalyst component was dried and analyzed for composition and was found to contain 0.72 mg of Zr atom per 1 g of the solid catalyst component.

Polymerization

An ethylene polymer was produced in a 290 L complete stirring-mixing polymerization reactor using the prepolymerized catalyst component (EYP-6).

To the polymerization tank, there were continuously supplied solvent hexane at 45 L/hour, the prepolymerized catalyst component at 0.32 mmol/hour in terms of Zr atom, triisobutylaluminum at 20.0 mmol/hour, ethylene at 8.0 kg/hour and 1-hexene at 700 g/hour. At the same time, the polymer slurry was continuously discharged from the polymerization tank such that the volume of the solvent in the polymerization tank was constant. The polymerization was carried out at a total pressure of 0.8 MPa-G, a polymerization temperature of 80° C. and a retention time of 2.6 hours. The polymer slurry continuously discharged from the polymerization tank was fed to a flush drum where unreacted ethylene was substantially removed. The hexane in the polymer slurry was removed with a solvent separation apparatus, and the residue was dried to afford an ethylene polymer at 5.6 kg/hour.

The ethylene polymer obtained was formulated into specimens in the same manner as in Example M-33. The specimens were used for properties evaluation and extrusion lamination. The results are set forth in Tables 18 and 19.

Comparative Example M-8 resulted in a low molecular weight at the maximum weight fraction (peak top M) in the molecular weight distribution curve by GPC, and the heat seal strength was low compared to Examples.

Comparative Example M-9

An ethylene/hexene copolymer was produced in the same manner as in Example M-37.

The ethylene polymer obtained was formulated into specimens in the same manner as in Example M-33. The specimens were used for properties evaluation and extrusion lamination. The results are set forth in Tables 18 and 19.

Comparative Example M-10

Pellets of polyethylene obtained by high-pressure radical polymerization, purchased from Prime Polymer Co., Ltd.

(MIRASON 11), were used as a specimen for properties evaluation and extrusion lamination. The results are set forth in Tables 18 and 19.

Comparative Example M-10 resulted in poor heat seal strength. The total of methyl branches [A(/1000 C)] and ethyl branches [B(/1000 C)], (A+B), was large compared to Examples.

Comparative Example M-11

Preparation of Solid Catalyst Component (EY-7)

A 200 mL glass flask purged with nitrogen was charged with 100 mL of toluene and the content was stirred. Further, the toluene slurry of the solid component (S) (2.0 g in terms of the solid component) was added thereto. Furthermore, 32.1 mL of a toluene solution of dimethylsilylene bisindenyl zirconium dichloride (0.0015 mmol/mL in terms of Zr atom) was added dropwise. Reaction was performed at room temperature for 1 hour. The supernatant was removed by decantation. The residue was washed with decane two times and was slurried into 100 mL of a decane slurry (solid catalyst component EY-7). A portion of the decane slurry of the solid catalyst component (EY-7) was sampled and the concentrations were determined, resulting in a Zr concentration of 0.043 mg/mL and an Al concentration of 2.49 mg/mL.

Polymerization

A 1 L SUS autoclave thoroughly purged with nitrogen was charged with 500 mL of purified heptane, and ethylene was passed through the autoclave to saturate the liquid phase and the gas phase with ethylene. Further, the system was purged with hydrogen/ethylene mixture gas (hydrogen concentration: 0.54 vol %). Subsequently, 15 mL of 1-hexene and 0.375 mmol of triisobutylaluminum were added in this order, and 0.5 g of the solid catalyst component (EY-7) was added to the autoclave. The temperature was increased to 80° C., and polymerization was performed at 0.78 MPa·G for 90 minutes. The polymer obtained was dried under vacuum for 10 hours to afford 86.7 g of an ethylene polymer.

The ethylene polymer obtained was formulated into specimens in the same manner as in Example M-1. The specimens were used for properties evaluation. The results are set forth in Table 18.

Comparative Example M-11 resulted in a small MT/$\eta^*$ ratio, and the zero-shear viscosity ($\eta_0$) did not meet Equation (Eq-1). Based on these results, the polymer was assumed to cause large neck-in and take-up surge.

Comparative Example M-12

Preparation of Solid Catalyst Component (EY-8)

A solid catalyst component (EY-8) was prepared in the same manner as for the solid catalyst component (EY-6) in Comparative Example M-8, except that the reaction molar ratio of the metallocene compound (E1) and the metallocene compound (B2) was changed from (E1)/(B2)=95/5 (molar ratio) to (E1)/(B2)=85/15 (molar ratio).

Preparation of Prepolymerized Catalyst Component (EYP-8)

The hexane slurry of the solid catalyst component (EY-8) was cooled to 10° C. Ethylene was continuously supplied to the system under atmospheric pressure for several minutes.

During the supply, the temperature in the system was maintained at 10 to 15° C. Subsequently, 1.6 mol of triisobutylaluminum and 80 mL of 1-hexene were added. After the addition of 1-hexene, the supply of ethylene was initiated at 1.8 kg/hour and prepolymerization was initiated. The temperature in the system reached 24° C. in 25 minutes after the initiation of the prepolymerization. The temperature in the system was thereafter maintained at 24 to 26° C. After 35 minutes from the initiation of the prepolymerization, 39.0 mL of 1-hexene was added. Another 39.0 mL of 1-hexene was added after the passage of 60 minutes.

After 85 minutes from the initiation of the prepolymerization, the ethylene supply was terminated and the system was purged with nitrogen to terminate the prepolymerization. The supernatant was removed by decantation. The prepolymerized catalyst component was washed with hexane four times. Thus, a prepolymerized catalyst component (EYP-8) was obtained which was polymerized with 2.93 g of the polymer per 1 g of the solid catalyst component. A portion of the prepolymerized catalyst component was dried and analyzed for composition and was found to contain 0.72 mg of Zr atom per 1 g of the solid catalyst component.

Polymerization

An ethylene/1-hexene copolymer was produced in the same manner as in Comparative Example M-8, except that the ethylene supply rate and the 1-hexene supply rate were changed from 8.0 kg/hour and 700 g/hour to 5.0 kg/hour and 1900 g/hour, respectively. After the density of the polymer reached below 935 kg/m$^3$, the supernatant of the polymer slurry discharged from the polymerization tank became white turbid. After 8 hours after the polymer's density reached 920 kg/m$^3$, the polymer was no longer separated from the solvent and the slurry properties became very bad. With these results, the continuous operation was cancelled. The ethylene/1-hexene copolymer obtained before the cancellation of the operation was used for properties evaluation and extrusion lamination. The results are set forth in Tables 18 and 19.

TABLE 1

|  |  | Ex. L-1 | Ex. L-2 | Ex. L-3 | Ex. L-4 | Ex. L-5 |
|---|---|---|---|---|---|---|
| Kind of complex |  | A1 | A2 | A3 | A4 | A5 |
| Catalyst amount | mmol-Zr | 0.001 | 0.001 | 0.001 | 0.0003 | 0.001 |
| Polymer amount | g | 2.41 | 2.48 | 1.62 | 0.94 | 0.60 |
| Activity | kg/mmol-Zr/h | 28.8 | 30.0 | 19.2 | 22.8 | 7.2 |
| GPC | Mw × 10$^{-4}$ | 3.48 | 2.81 | 2.82 | 8.25 | 2.72 |
|  | Mn × 10$^{-4}$ | 1.35 | 1.17 | 1.23 | 1.23 | 1.2 |
|  | Mw/Mn | 2.58 | 2.4 | 2.29 | 6.71 | 2.29 |
| $^1$H-NMR | α (branches/1000 C.) | 0.76 | 0.86 | 0.85 | 0.86 | 0.85 |
|  | α × Mn | 10260 | 10062 | 10455 | 10578 | 10200 |

|  |  | Ex. L-6 | Ex. L-7 | Ex. L-8 | Ex. L-9 | Ex. L-10 |
|---|---|---|---|---|---|---|
| Kind of complex |  | A6 | A7 | A8 | A9 | A10 |
| Catalyst amount | mmol-Zr | 0.0003 | 0.001 | 0.001 | 0.001 | 0.005 |
| Polymer amount | g | 2.30 | 0.72 | 6.01 | 2.97 | 0.75 |
| Activity | kg/mmol-Zr/h | 55.2 | 8.4 | 36.0 | 18.0 | 1.2 |
| GPC | Mw × 10$^{-4}$ | 9.68 | 3.87 | 3.7 | 3.07 | 0.31 |
|  | Mn × 10$^{-4}$ | 4.69 | 1.36 | 1.45 | 1.16 | 0.16 |
|  | Mw/Mn | 2.06 | 2.85 | 2.55 | 2.65 | 1.94 |
| $^1$H-NMR | α (branches/1000 C.) | 0.21 | 0.76 | 0.68 | 0.90 | 5.14 |
|  | α × Mn | 9849 | 10336 | 9860 | 10440 | 8224 |

|  |  | Ex. L-11 | Ex. L-12 | Ex. L-13 | Ex. L-14 | Ex. L-15 |
|---|---|---|---|---|---|---|
| Kind of complex |  | A1 | A2 | A3 | A4 | A5 |
| Solid catalyst |  | X-1 | X-2 | X-3 | X-4 | X-5 |
| Solid catalyst amount | G | 0.040 | 0.010 | 0.010 | 0.020 | 0.040 |
| Polymer amount | G | 24.6 | 73.3 | 64.8 | 69.2 | 25.2 |
| Activity | g/g-cat/h | 410 | 4880 | 4320 | 2310 | 630 |
| D |  | 941 | 941 | 938 | 939 | 940 |
| GPC | Mw × 10$^{-4}$ | 5.8 | 2.3 | 2.5 | 2.4 | 3.5 |
|  | Mn × 10$^{-4}$ | 1.7 | 1.3 | 1.4 | 1.3 | 1.5 |
|  | Mw/Mn | 3.4 | 1.8 | 1.8 | 1.9 | 2.3 |
| $^1$H-NMR | α (branches/1000 C.) | 0.33 | 0.40 | 0.40 | 0.55 | 0.43 |
|  | α × Mn | 5610 | 5200 | 5560 | 7040 | 6493 |

|  |  | Ex. L-16 | Ex. L-17 | Ex. L-18 | Ex. L-19 | Ex. L-20 |
|---|---|---|---|---|---|---|
| Kind of complex |  | A6 | A7 | A8 | A9 | A10 |
| Solid catalyst |  | X-6 | X-7 | X-8 | X-9 | X-10 |
| Solid catalyst amount | G | 0.014 | 0.016 | 0.010 | 0.020 | 0.100 |
| Polymer amount | G | 50.8 | 110.7 | 55.6 | 91.0 | 5.8 |
| Activity | g/g-cat/h | 2420 | 4610 | 5560 | 3110 | 40 |
| D |  | 940 | 943 | 938 | 941 | 945 |
| GPC | Mw × 10$^{-4}$ | 3.8 | 2.5 | 2.5 | 2.4 | 1.3 |
|  | Mn × 10$^{-4}$ | 1.8 | 1.2 | 1.4 | 1.3 | 0.5 |
|  | Mw/Mn | 2.2 | 2.0 | 1.8 | 1.8 | 2.8 |

TABLE 1-continued

| $^1$H-NMR | α (branches/1000 C.) | 0.17 | 0.33 | 0.43 | 0.41 | 1.76 |
|---|---|---|---|---|---|---|
| | α × Mn | 2992 | 4059 | 5977 | 5371 | 8272 |

TABLE 2

| | | Ex. L-21 | Ex. L-22 | Ex. L-23 | Ex. L-24 |
|---|---|---|---|---|---|
| Kind of complex | | A2 | A3 | A4 | A6 |
| Solid catalyst | | X-2 | X-3 | X-4 | X-6 |
| Solid catalyst amount | g | 0.025 | 0.028 | 0.05 | 0.04 |
| Polymer amount | g | 39.5 | 112.6 | 55.8 | 54.5 |
| Activity | g/g-cat/h | 1579 | 4021 | 1115 | 1361 |
| D | | 923 | 923 | 924 | 924 |
| GPC | Mw × 10$^{-4}$ | 2.3 | 2.0 | 2.4 | 3.4 |
| | Mn × 10$^{-4}$ | 1.3 | 1.1 | 1.2 | 1.5 |
| | Mw/Mn | 1.8 | 1.8 | 2.0 | 2.2 |
| $^1$H-NMR | α (branches/1000 C) | 0.5 | 0.45 | 0.48 | 0.15 |
| | α × Mn | 6350 | 4905 | 5712 | 2265 |

TABLE 3

| | | Comp. Ex. L-1 | Comp. Ex. L-2 | Comp. Ex. L-3 | Comp. Ex. L-4 | Comp. Ex. L-5 |
|---|---|---|---|---|---|---|
| Kind of complex | | E1 | E2 | E3 | E4 | E5 |
| Catalyst amount | mmol-Zr | 0.001 | 0.0003 | 0.001 | 0.0003 | 0.001 |
| Polymer amount | g | 2.07 | 3.43 | 4.24 | 1.71 | 6.70 |
| Activity | kg/mmol-Zr/h | 12.6 | 68.4 | 25.2 | 40.8 | 80.4 |
| GPC | Mw × 10$^{-4}$ | 1.72 | 4.47 | 9.98 | 16.81 | 15 |
| | Mn × 10$^{-4}$ | 0.69 | 2.29 | 4.29 | 6.87 | 6.28 |
| | Mw/Mn | 2.49 | 1.95 | 2.33 | 2.45 | 2.39 |
| $^1$H-NMR | α (branches/1000 C.) | 1.47 | 0.46 | 0.16 | — | 0.15 |
| | α × Mn | 10143 | 10534 | 6864 | — | 9420 |

| | | Comp. Ex. L-6 | Comp. Ex. L-7 | Comp. Ex. L-8 | Comp. Ex. L-9 | Comp. Ex. L-10 | Comp. Ex. L-11 | Comp. Ex. L-12 |
|---|---|---|---|---|---|---|---|---|
| Kind of complex | | E1 | E2 | E3 | E4 | E5 | E6 | E7 |
| Solid catalyst | | EX-1 | EX-2 | EX-3 | EX-4 | EX-5 | EX-6 | EX-7 |
| Solid catalyst amount | g | 0.100 | 0.013 | 0.020 | 0.020 | 0.060 | 0.100 | 0.013 |
| Polymer amount | g | 9.7 | 115.8 | 6.6 | 33.6 | 144.3 | 45.9 | 71.9 |
| Activity | g/g-cat/h | 64 | 6124 | 220 | 1121 | 1603 | 305 | 3800 |
| D | | 950 | 942 | — | 926 | 926 | 934 | 937 |
| GPC | Mw × 10$^{-4}$ | 3.7 | 2.8 | 11.6 | 15.3 | 16.2 | 20.2 | 7.6 |
| | Mn × 10$^{-4}$ | 1.1 | 1.5 | 3.4 | 4.7 | 4.0 | 4.9 | 3.2 |
| | Mw/Mn | 3.5 | 1.9 | 3.4 | 3.3 | 4.0 | 4.1 | 2.4 |
| $^1$H-NMR | α (branches/1000 C.) | 0.90 | 0.29 | — | 0.06 | 0.10 | 0.05 | 0.06 |
| | α × Mn | 9450 | 4234 | — | 2802 | 4202 | 2445 | 1896 |

TABLE 4

| | | | Example | | | |
|---|---|---|---|---|---|---|
| | | | M-1 | M-2 | M-3 | M-4 |
| Solid catalyst component | No. | | Y-1 | Y-1 | Y-1 | Y-2 |
| | Metallocene compound | Cmpnt. A | A2 | A2 | A2 | A3 |
| | | Cmpnt. B | B1 | B1 | B1 | B1 |
| | Cmpnt. (A)/cmpnt. (B) | Molar ratio | 60/40 | 60/40 | 60/40 | 60/40 |
| Prepolymerized catalyst component | No. | | — | — | — | — |
| Polymerization conditions | Polymer | | Ethylene/ hexene | Ethylene/ hexene | Ethylene/ butene | Ethylene/ hexene |
| | Hydrogen amount | vol % | 0 | 0.1 | 0 | 0 |
| Polymerization results | Solid catalyst component amount | g | 0.02 | 0.02 | 0.04 | 0.015 |

TABLE 4-continued

|  |  |  |  |  |  |  |
|---|---|---|---|---|---|---|
| Polymer analysis results | Yield | g | 76.25 | 75.45 | 68.86 | 60.22 |
|  | Activity | g/g-cat/h | 2540 | 2510 | 1150 | 2680 |
|  | MFR | (g/10 min) | 16.9 | 22.1 | 25.7 | 13.3 |
|  | $[\eta]$ |  | 1.20 | 1.08 | 1.05 | 1.28 |
|  | D |  | 937 | 938 | 921 | 935 |
|  | B.D | g/ml | 0.332 | 0.345 | 0.388 | 0.378 |
|  | GPC | Mw | 86200 | 70100 | 78300 | 76000 |
|  |  | Mn | 15200 | 10600 | 12200 | 14700 |
|  |  | Mw/Mn | 5.7 | 6.6 | 6.4 | 5.2 |
|  | GPC-$[\eta]$ | Mw | 17800 | 13600 | 14800 | 18100 |
|  |  | Mn | 143000 | 134000 | 113400 | 149000 |
|  |  | Mw/Mn | 8.0 | 9.9 | 7.7 | 8.2 |
|  | Log$[\eta]$ |  | 0.0792 | 0.0334 | 0.0212 | 0.1072 |
|  | MT | g | 3.0 | 2.4 | 3.2 | 3.0 |
|  | $\eta^*$ |  | 7883 | 7483 | 5244 | 9483 |
|  | $\eta 0$ |  | 19244 | 19462 | 7657 | 24398 |
|  | MT/$\eta^*$ |  | 0.00038 | 0.00032 | 0.00061 | 0.00031 |
|  | LogM$_{GPC-[\eta]}$ |  | 5.16 | 5.13 | 5.05 | 5.17 |
| GPC peak analysis | Fraction ratio | Cmpnt. A | 82.1 | 80.2 | 78.4 | 75.6 |
|  |  | Cmpnt. B | 9.9 | 12.6 | 15.1 | 16.0 |
|  |  | 3rd cmpnt. | 8.0 | 7.2 | 6.5 | 8.4 |
|  | LogM$_{max}$ |  | 4.34 | 4.24 | 4.28 | 4.36 |
|  | H$_{max}$ |  | 0.022 | 0.021 | 0.021 | 0.021 |
|  | LogM$_{second}$ |  | 5.58 | 5.54 | 5.6 | 5.58 |
|  | H$_{second}$ |  | 0.0027 | 0.0023 | 0.0026 | 0.0035 |
|  | H$_{max}$/H$_{second}$ |  | 8.3 | 9.0 | 8.1 | 6.0 |

|  |  |  | Example | | |
|---|---|---|---|---|---|
|  |  |  | M-5 | M-6 | M-7 |
| Solid catalyst component | No. |  | Y-2 | Y-2 | Y-3 |
|  | Metallocene compound | Cmpnt. A | A3 | A3 | A4 |
|  |  | Cmpnt. B | B1 | B1 | B1 |
|  | Cmpnt. (A)/cmpnt. (B) | Molar ratio | 60/40 | 60/40 | 80/20 |
| Prepolymerized catalyst component | No. |  | — | — | — |
| Polymerization conditions | Polymer |  | Ethylene/ hexene | Ethylene/ butene | Ethylene/ hexene |
|  | Hydrogen amount | vol % | 0.05 | 0 | 0 |
| Polymerization results | Solid catalyst component amount | g | 0.015 | 0.0344 | 0.03 |
|  | Yield | g | 55.09 | 41.59 | 80.02 |
|  | Activity | g/g-cat/h | 2450 | 810 | 1780 |
| Polymer analysis results | MFR | (g/10 min) | 17.7 | 24.5 | 11.4 |
|  | $[\eta]$ |  | 1.16 | 1.04 | 1.23 |
|  | D |  | 936 | 921 | 936 |
|  | B.D | g/ml | 0.386 | 0.313 | 0.342 |
|  | GPC | Mw | 70800 | 67400 | 74600 |
|  |  | Mn | 13800 | 13500 | 14400 |
|  |  | Mw/Mn | 5.1 | 5.0 | 5.2 |
|  | GPC-$[\eta]$ | Mw | 16100 | 16000 | 17800 |
|  |  | Mn | 112500 | 105000 | 132500 |
|  |  | Mw/Mn | 7.0 | 6.6 | 7.4 |
|  | Log$[\eta]$ |  | 0.0645 | 0.0170 | 0.0899 |
|  | MT | g | 2.6 | 2.7 | 3.8 |
|  | $\eta^*$ |  | 6811 | 4131 | 11493 |
|  | $\eta 0$ |  | 16589 | 6896 | 37781 |
|  | MT/$\eta^*$ |  | 0.00038 | 0.00064 | 0.00033 |
|  | LogM$_{GPC-[\eta]}$ |  | 5.05 | 5.02 | 5.12 |
| GPC peak analysis | Fraction ratio | Cmpnt. A | 81.7 | 80.7 | 85.3 |
|  |  | Cmpnt. B | 12.5 | 15.2 | 9.5 |
|  |  | 3rd cmpnt. | 5.7 | 4.1 | 5.2 |
|  | LogM$_{max}$ |  | 4.32 | 4.35 | 4.34 |
|  | H$_{max}$ |  | 0.023 | 0.022 | 0.022 |
|  | LogM$_{second}$ |  | 5.56 | 5.58 | 5.52 |
|  | H$_{second}$ |  | 0.0025 | 0.0023 | 0.0026 |
|  | H$_{max}$/H$_{second}$ |  | 9.2 | 9.6 | 8.6 |

TABLE 5

|  |  |  | Example | | | |
|---|---|---|---|---|---|---|
|  |  |  | M-8 | M-9 | M-10 | M-11 |
| Solid catalyst component | No. |  | Y-3 | Y-4 | Y-4 | Y-4 |
|  | Metallocene compound | Cmpnt. A | A4 | A6 | A6 | A6 |
|  |  | Cmpnt. B | B1 | B1 | B1 | B1 |
|  | Cmpnt. (A)/cmpnt. (B) | Molar ratio | 80/20 | 70/30 | 70/30 | 70/30 |
| Prepolymerized catalyst component | No. |  | — | — | — | — |
| Polymerization conditions | Polymer |  | Ethylene/hexene | Ethylene/hexene | Ethylene/hexene | Ethylene/butene |
|  | Hydrogen amount | vol % | 0.1 | 0 | 0.1 | 0 |
| Polymerization results | Solid catalyst component amount | g | 0.03 | 0.03 | 0.03 | 0.056 |
|  | Yield | g | 84.69 | 76.04 | 80.33 | 51.57 |
|  | Activity | g/g-cat/h | 1880 | 1690 | 1780 | 920 |
| Polymer analysis results | MFR | (g/10 min) | 14.5 | 9.1 | 21.7 | 10.3 |
|  | $[\eta]$ |  | 1.11 | 1.33 | 1.09 | 1.27 |
|  | D |  | 938 | 939 | 943 | 921 |
|  | B.D | g/ml | 0.365 | 0.388 | 0.376 | 0.312 |
|  | GPC | Mw | 68200 | 77500 | 64300 | 67800 |
|  |  | Mn | 11800 | 19400 | 14000 | 17600 |
|  |  | Mw/Mn | 5.8 | 4.0 | 4.6 | 3.9 |
|  | GPC-$[\eta]$ | Mw | 14760 | 22600 | 15400 | 20810 |
|  |  | Mn | 106700 | 112000 | 82300 | 106500 |
|  |  | Mw/Mn | 7.2 | 5.0 | 5.3 | 5.1 |
|  | Log$[\eta]$ |  | 0.0453 | 0.1239 | 0.0374 | 0.1038 |
|  | MT | g | 2.8 | 2.1 | 1.6 | 2.0 |
|  | $\eta^*$ |  | 10247 | 8249 | 5004 | 8837 |
|  | $\eta0$ |  | 29682 | 12940 | 8717 | 14293 |
|  | MT/$\eta^*$ |  | 0.00027 | 0.00025 | 0.00032 | 0.00023 |
|  | LogM$_{GPC-[\eta]}$ |  | 5.03 | 5.05 | 4.92 | 5.03 |
| GPC peak analysis | Fraction ratio | Cmpnt. A | 82.6 | 86.5 | 87.6 | 87.3 |
|  |  | Cmpnt. B | 10.5 | 10.0 | 8.1 | 8.9 |
|  |  | 3rd cmpnt. | 6.9 | 3.5 | 4.3 | 3.8 |
|  | LogM$_{max}$ |  | 4.22 | 4.5 | 4.38 | 4.46 |
|  | H$_{max}$ |  | 0.022 | 0.021 | 0.021 | 0.021 |
|  | LogM$_{second}$ |  | 5.12 | 5.6 | 5.52 | 5.42 |
|  | H$_{second}$ |  | 0.0029 | 0.0018 | 0.0017 | 0.0021 |
|  | H$_{max}$/H$_{second}$ |  | 7.6 | 11.9 | 12.0 | 10.1 |

|  |  |  | Example | | |
|---|---|---|---|---|---|
|  |  |  | M-12 | M-13 | M-14 |
| Solid catalyst component | No. |  | Y-5 | Y-2 | Y-6 |
|  | Metallocene compound | Cmpnt. A | A2 | A3 | A3 |
|  |  | Cmpnt. B | B1 | B1 | B2 |
|  | Cmpnt. (A)/cmpnt. (B) | Molar ratio | 45/55 | 60/40 | 30/70 |
| Prepolymerized catalyst component | No. |  | — | — | — |
| Polymerization conditions | Polymer |  | Ethylene/butene | Ethylene/butene | Ethylene/hexene |
|  | Hydrogen amount | vol % | 0 | 0 | 0 |
| Polymerization results | Solid catalyst component amount | g | 0.056 | 0.039 | 0.045 |
|  | Yield | g | 46.65 | 51.85 | 74.38 |
|  | Activity | g/g-cat/h | 550 | 890 | 1090 |
| Polymer analysis results | MFR | (g/10 min) | 20.6 | 9 | 8.5 |
|  | $[\eta]$ |  | 1.01 | 1.15 | 1.35 |
|  | D |  | 903 | 902 | 935 |
|  | B.D | g/ml | — | — | — |
|  | GPC | Mw | 52800 | 64100 | 102000 |
|  |  | Mn | 13900 | 15500 | 16700 |
|  |  | Mw/Mn | 3.8 | 4.1 | 6.1 |
|  | GPC-$[\eta]$ | Mw | 19000 | 19800 | 156000 |
|  |  | Mn | 87300 | 99860 | 18200 |
|  |  | Mw/Mn | 4.6 | 5.0 | 8.6 |
|  | Log$[\eta]$ |  | 0.0043 | 0.0607 | 0.1303 |

TABLE 5-continued

|  |  |  |  |  |  |
|---|---|---|---|---|---|
|  | MT | g | 1.7 | 3.9 | 3.1 |
|  | $\eta^*$ |  | 3953 | 10726 | 11618 |
|  | $\eta 0$ |  | 6558 | 24168 | 29797 |
|  | MT/$\eta^*$ |  | 0.00043 | 0.00037 | 0.00027 |
|  | $LogM_{GPC\text{-}[\eta]}$ |  | 4.94 | 5.00 | 5.19 |
| GPC peak analysis | Fraction ratio | Cmpnt. A | 65.7 | 64.5 | 85.5 |
|  |  | Cmpnt. B | 31.3 | 32.0 | 12.5 |
|  |  | 3rd cmpnt. | 3.0 | 3.5 | 12.9 |
|  | $LogM_{max}$ |  | 4.32 | 4.34 | — |
|  | $H_{max}$ |  | 0.021 | 0.020 | — |
|  | $LogM_{second}$ |  | 5.5 | 5.46 | — |
|  | $H_{second}$ |  | 0.0021 | 0.0030 | — |
|  | $H_{max}/H_{second}$ |  | 10.2 | 6.7 | — |

TABLE 6

|  |  |  | Example | | | |
|---|---|---|---|---|---|---|
|  |  |  | M-15 | M-16 | M-17 | M-18 |
| Solid catalyst component | No. |  | Y-7 | Y-8 | Y-9 | Y-10 |
|  | Metallocene compound | Cmpnt. A | A3 | A3 | A3 | A3 |
|  |  | Cmpnt. B | B3 | B4 | B5 | B6 |
|  | Cmpnt. (A)/cmpnt. (B) | Molar ratio | 70/30 | 60/40 | 55/45 | 55/45 |
| Prepolymerized catalyst component | No. |  | — | — | — | — |
| Polymerization conditions | Polymer |  | Ethylene/hexene | Ethylene/hexene | Ethylene/hexene | Ethylene/hexene |
|  | Hydrogen amount | vol % | 0 | 0 | 0 | 0 |
| Polymerization results | Solid catalyst component amount | g | 0.030 | 0.030 | 0.045 | 0.030 |
|  | Yield | g | 121.34 | 75.51 | 113.72 | 116.03 |
|  | Activity | g/g-cat/h | 2670 | 1660 | 1670 | 2550 |
| Polymer analysis results | MFR | (g/10 min) | 15.8 | 7.6 | 6.6 | 14.8 |
|  | $[\eta]$ |  | 1.16 | 1.32 | 1.38 | 1.17 |
|  | D |  | 939 | 935 | 938 | 916 |
|  | B.D | g/ml | — | — | — | — |
|  | GPC | Mw | 76100 | 81000 | 82000 | 69300 |
|  |  | Mn | 14200 | 15900 | 16300 | 15900 |
|  |  | Mw/Mn | 5.3 | 5.1 | 5.0 | 4.4 |
|  | GPC-$[\eta]$ | Mw | 120800 | 148900 | 154300 | 92900 |
|  |  | Mn | 16900 | 22000 | 23000 | 21800 |
|  |  | Mw/Mn | 7.1 | 6.8 | 6.7 | 4.3 |
|  | Log[$\eta$] |  | 0.0645 | 0.1206 | 0.1399 | 0.0682 |
|  | MT | g | 2.6 | 4.5 | 4.8 | 1.88 |
|  | $\eta^*$ |  | 8400 | 15000 | 17000 | 6061 |
|  | $\eta 0$ |  | 17666 | 35000 | 40000 | 11634 |
|  | MT/$\eta^*$ |  | 0.00031 | 0.00030 | 0.00028 | 0.00031 |
|  | $LogM_{GPC\text{-}[\eta]}$ |  | 5.08 | 5.17 | 5.19 | 4.97 |
| GPC peak analysis | Fraction ratio | Cmpnt. A | 80.4 | 78.2 | 79.5 | 83.9 |
|  |  | Cmpnt. B | 13.8 | 14.8 | 14.8 | 11.8 |
|  |  | 3rd cmpnt. | 5.8 | 7.0 | 5.7 | 4.3 |
|  | $LogM_{max}$ |  | — | — | — | — |
|  | $H_{max}$ |  | — | — | — | — |
|  | $LogM_{second}$ |  | — | — | — | — |
|  | $H_{second}$ |  | — | — | — | — |
|  | $H_{max}/H_{second}$ |  | — | — | — | — |

|  |  |  | Example | | |
|---|---|---|---|---|---|
|  |  |  | M-19 | M-20 | M-21 |
| Solid catalyst component | No. |  | X-2/X-11 | X-3/X-11 | Y-11 |
|  | Metallocene compound | Cmpnt. A | A2 | A3 | A2 |
|  |  | Cmpnt. B | B1 | B1 | B1 |
|  | Cmpnt. (A)/cmpnt. (B) | Molar ratio | 40/60 | 25/75 | 44/56 |
| Prepolymerized catalyst component | No. |  | — | — | YP-11 |
| Polymerization conditions | Polymer |  | Ethylene/hexene | Ethylene/hexene | Ethylene/hexene |

TABLE 6-continued

|  |  |  |  |  |  |
|---|---|---|---|---|---|
|  | Hydrogen amount | vol % | 0 | 0 | 0 |
| Polymerization results | Solid catalyst component amount | g | 0.020 | 0.020 | 0.019 |
|  | Yield | g | 79.67 | 48.65 | 64.33 |
|  | Activity | g/g-cat/h | 2660 | 1620 | 2210 |
| Polymer analysis results | MFR | (g/10 min) | 21.1 | 7.6 | 7.6 |
|  | [η] |  | 1.07 | 1.28 | 1.36 |
|  | D |  | 937 | 933 | 934 |
|  | B.D | g/ml | 0.330 | 0.335 | 0.405 |
|  | GPC | Mw | 68300 | 83500 | 99800 |
|  |  | Mn | 15700 | 17900 | 15500 |
|  |  | Mw/Mn | 4.4 | 4.7 | 6.4 |
|  | GPC-[η] | Mw | 110400 | 126000 | 18200 |
|  |  | Mn | 20500 | 22200 | 158088 |
|  |  | Mw/Mn | 5.4 | 5.7 | 8.7 |
|  | Log[η] |  | 0.0294 | 0.1072 | 0.1335 |
|  | MT | g | 1.8 | 3.7 | 3.5 |
|  | η* |  | 4458 | 11172 | 16528 |
|  | η0 |  | 6875 | 24115 | 54569 |
|  | MT/η* |  | 0.00041 | 0.00033 | 0.00021 |
|  | LogM$_{GPC-[η]}$ |  | 5.04 | 5.10 | 5.20 |
| GPC peak analysis | Fraction ratio | Cmpnt. A | 83.9 | 76.1 | 75.7 |
|  |  | Cmpnt. B | 12.9 | 20.4 | 18.1 |
|  |  | 3rd cmpnt. | 3.8 | 4.4 | 7.5 |
|  | LogM$_{max}$ |  | 4.38 | 4.4 | 4.34 |
|  | H$_{max}$ |  | 0.023 | 0.022 | 0.021 |
|  | LogM$_{second}$ |  | 5.16 | 5.52 | 5.6 |
|  | H$_{second}$ |  | 0.0023 | 0.0029 | 0.0030 |
|  | H$_{max}$/H$_{second}$ |  | 10.0 | 7.7 | 7.1 |

TABLE 7

|  |  |  | Example | | |
|---|---|---|---|---|---|
|  |  |  | M-22 | M-23 | M-24 |
| Solid catalyst component | No. |  | Y-12 | Y-13 | Y-14 |
|  | Metallocene compound | Cmpnt. A | A2 | A3 | A3 |
|  |  | Cmpnt. B | B1 | B1 | B1 |
|  | Cmpnt. (A)/cmpnt. (B) | Molar ratio | 47/53 | 37/63 | 45/55 |
| Prepolymerized catalyst component | No. |  | YP-12 | YP-13 | YP-14 |
| Polymerization conditions | Polymer |  | Ethylene/ hexene | Ethylene/ hexene | Ethylene/ hexene |
|  | Hydrogen amount | vol % | 0 | 0 | 0 |
| Polymerization results | Solid catalyst component amount | g | 0.022 | 0.020 | 0.023 |
|  | Yield | g | 81.86 | 59.57 | 80.28 |
|  | Activity | g/g-cat/h | 2450 | 1990 | 2320 |
| Polymer analysis results | MFR | (g/10 min) | 11.2 | 2.48 | 4.4 |
|  | [η] |  | 1.30 | 1.59 | 1.58 |
|  | D |  | 936 | 932 | 935 |
|  | B.D | g/ml | 0.393 | 0.408 | 0.375 |
|  | GPC | Mw | 100500 | 119400 | 108300 |
|  |  | Mn | 14700 | 16600 | 16500 |
|  |  | Mw/Mn | 6.8 | 7.2 | 6.6 |
|  | GPC-[η] | Mw | 17900 | 19400 | 19100 |
|  |  | Mn | 153108 | 206043 | 158271 |
|  |  | Mw/Mn | 8.6 | 10.6 | 8.3 |
|  | Log[η] |  | 0.1139 | 0.2014 | 0.1987 |
|  | MT | g | 3.2 | 5.6 | 3.6 |
|  | η* |  | 17125 | 39667 | 27375 |
|  | η0 |  | 55619 | 283897 | 124656 |
|  | MT/η* |  | 0.00019 | 0.00014 | 0.00013 |
|  | LogM$_{GPC-[η]}$ |  | 5.18 | 5.31 | 5.20 |
| GPC peak analysis | Fraction ratio | Cmpnt. A | 77.3 | 67.8 | 71.2 |
|  |  | Cmpnt. B | 15.1 | 23.6 | 20.7 |
|  |  | 3rd cmpnt. | 7.6 | 8.5 | 8.1 |
|  | LogM$_{max}$ |  | 4.32 | 4.36 | 4.36 |

TABLE 7-continued

|  |  |  |  |  |
|---|---|---|---|---|
| $H_{max}$ |  | 0.021 | 0.019 | 0.020 |
| $LogM_{second}$ |  | 5.6 | 5.58 | 5.58 |
| $H_{second}$ |  | 0.0028 | 0.0039 | 0.0037 |
| $H_{max}/H_{second}$ |  | 7.6 | 4.9 | 5.3 |

|  |  |  | Example | |
|---|---|---|---|---|
|  |  |  | M-25 | M-26 |
| Solid catalyst component | No. |  | Y-15 | Y-16 |
|  | Metallocene compound | Cmpnt. A | A3 | A3 |
|  |  | Cmpnt. B | B1 | B1 |
|  | Cmpnt. (A)/cmpnt. (B) | Molar ratio | 49/51 | 55/45 |
| Prepolymerized catalyst component | No. |  | YP-15 | YP-16 |
| Polymerization conditions | Polymer |  | Ethylene/hexene | Ethylene/hexene |
|  | Hydrogen amount | vol % | 0 | 0 |
| Polymerization results | Solid catalyst component amount | g | 0.033 | 0.019 |
|  | Yield | g | 94.11 | 63.63 |
|  | Activity | g/g-cat/h | 1920 | 2240 |
| Polymer analysis results | MFR | (g/10 min) | 9.2 | 14.7 |
|  | [η] |  | 1.30 | 1.23 |
|  | D |  | 937 | 935 |
|  | B.D | g/ml | — | — |
|  | GPC | Mw | 99700 | 90100 |
|  |  | Mn | 16000 | 15200 |
|  |  | Mw/Mn | 6.2 | 5.9 |
|  | GPC-[η] | Mw | 1.81 | 17700 |
|  |  | Mn | 13.58 | 125673 |
|  |  | Mw/Mn | 7.5 | 7.1 |
|  | Log[η] |  | 0.1139 | 0.0899 |
|  | MT | g | 3.3 | 3.4 |
|  | η* |  | 14084 | 9600 |
|  | η0 |  | 43845 | 24693 |
|  | MT/η* |  | 0.00024 | 0.00036 |
|  | $LogM_{GPC-[\eta]}$ |  | 5.13 | 5.10 |
| GPC peak analysis | Fraction ratio | Cmpnt. A | 75.6 | 77.9 |
|  |  | Cmpnt. B | 16.9 | 15.2 |
|  |  | 3rd cmpnt. | 7.5 | 7.0 |
|  | $LogM_{max}$ |  | 4.34 | 4.34 |
|  | $H_{max}$ |  | 0.021 | 0.022 |
|  | $LogM_{second}$ |  | 5.58 | 5.6 |
|  | $H_{second}$ |  | 0.0032 | 0.0027 |
|  | $H_{max}/H_{second}$ |  | 6.7 | 8.0 |

TABLE 8

|  |  |  | Example | | |
|---|---|---|---|---|---|
|  |  |  | M-27 | M-28 | M-29 |
| Solid catalyst component | No. |  | Y-17 | Y-18 | Y-19 |
|  | Metallocene compound | Cmpnt. A | A2 | A2 | A2 |
|  |  | Cmpnt. B | B1 | B1 | B1 |
|  | Cmpnt. (A)/cmpnt. (B) | Molar ratio | 44/56 | 42/58 | 24/76 |
| Prepolymerized catalyst component | No. |  | YP-17 | YP-18 | YP-19 |
| Polymerization conditions | Polymer |  | Ethylene/hexene | Ethylene/hexene | Ethylene/hexene |
|  | Hydrogen amount | vol % | 0 | 0 | 0 |
| Polymerization results | Solid catalyst component amount | g | 0.020 | 0.045 | 0.037 |
|  | Yield | g | 59.62 | 102.2 | 75.86 |
|  | Activity | g/g-cat/h | 1990 | 1500 | 1370 |
| Polymer | MFR | (g/10 min) | 11.2 | 8.6 | 0.8 |

TABLE 8-continued

| | | | | | |
|---|---|---|---|---|---|
| analysis results | $[\eta]$ | | 1.31 | 1.4 | — |
| | D | | 935 | 936 | 935 |
| | B.D | | 0.390 | 0.443 | 0.417 |
| | GPC | Mw | 97100 | 110400 | 133500 |
| | | Mn | 15500 | 16000 | 20400 |
| | | Mw/Mn | 6.3 | 6.9 | 6.5 |
| GPC peak analysis | Fraction ratio | Cmpnt. A | 78.7 | 74.4 | 60.8 |
| | | Cmpnt. B | 14.4 | 16.5 | 30.2 |
| | | 3rd cmpnt. | 6.9 | 9.2 | 9.1 |
| | $LogM_{max}$ | | 4.34 | 4.34 | 4.38 |
| | $H_{max}$ | | 0.022 | 0.021 | 0.018 |
| | $LogM_{second}$ | | 5.6 | 5.58 | 5.08 |
| | $H_{second}$ | | 0.0028 | 0.0035 | 0.0061 |
| | $H_{max}/H_{second}$ | | 7.87 | 5.98 | 2.96 |

| | | | Example | | |
|---|---|---|---|---|---|
| | | | M-30 | M-31 | M-32 |
| Solid catalyst compound | No. | | Y-11 | Y-19 | Y-19 |
| | Metallocene component | Cmpnt. A | A2 | A2 | A2 |
| | | Cmpnt. B | B1 | B1 | B1 |
| | Cmpnt. (A)/cmpnt. (B) | Molar ratio | 44/56 | 24/76 | 24/76 |
| Prepolymerized catalyst component | No. | | YP-11 | YP-19 | YP-19 |
| Polymerization conditions | Polymer | | Ethylene/ hexene | Ethylene/ hexene | Ethylene/ hexene |
| | Hydrogen amount | vol % | 0 | 0 | 0 |
| Polymerization results | Solid catalyst component amount | g | 0.030 | 0.035 | 0.034 |
| | Yield | g | 59.09 | 49.31 | 52.64 |
| | Activity | g/g-cat/h | 1330 | 940 | 1030 |
| Polymer analysis results | MFR | (g/10 min) | 9.3 | 9.4 | 3.5 |
| | $[\eta]$ | | 1.35 | 1.25 | 1.52 |
| | D | | 935 | 934 | 935 |
| | B.D | | 0.445 | 0.389 | 0.404 |
| | GPC | Mw | 85200 | 100400 | 106800 |
| | | Mn | 15500 | 18000 | 17000 |
| | | Mw/Mn | 5.5 | 5.6 | 6.3 |
| GPC peak analysis | Fraction ratio | Cmpnt. A | 78.1 | 76.4 | 72.8 |
| | | Cmpnt. B | 17.2 | 17.8 | 20.4 |
| | | 3rd cmpnt. | 4.7 | 5.8 | 6.8 |
| | $LogM_{max}$ | | 4.36 | 4.38 | 4.4 |
| | $H_{max}$ | | 0.021 | 0.022 | 0.020 |
| | $LogM_{second}$ | | 5.54 | 5.58 | 5.56 |
| | $H_{second}$ | | 0.0027 | 0.0031 | 0.0034 |
| | $H_{max}/H_{second}$ | | 7.93 | 6.99 | 5.85 |

TABLE 9

| | | | Comparative Example | | | |
|---|---|---|---|---|---|---|
| | | | Comp. Ex. M-1 | Comp. Ex. M-2 | Comp. Ex. M-3 | Comp. Ex. M-4 |
| Solid catalyst component | No. | | EY-1 | EY-2 | EY-3 | EY-4 |
| | Metallocene compound | Cmpnt. A | E1 | E5 | E2 | E2 |
| | | Cmpnt. B | B2 | B2 | B2 | B1 |
| | Cmpnt. (A)/cmpnt. (B) | Molar ratio | 80/20 | 35/65 | 10/90 | 30/70 |
| Prepolymerized catalyst component | No. | | — | — | — | — |
| Polymerization conditions | Polymer | | Ethylene/ hexene | Ethylene/ hexene | Ethylene/ butene | Ethylene/ hexene |
| | Hydrogen amount | vol % | 0.45 | 0.65 | 0 | 0 |
| Polymerization results | Solid catalyst component amount | g | 0.5 | 0.06 | 0.04 | 0.02 |
| | Yield | g | 87.44 | 47.9 | 77.81 | 91.57 |

TABLE 9-continued

|  |  |  | Comparative Example | | | |
|---|---|---|---|---|---|---|
|  |  |  | Comp. Ex. M-1 | Comp. Ex. M-2 | Comp. Ex. M-3 | Comp. Ex. M-4 |
| Polymer analysis results | Activity | g/g-cat/h | 120 | 530 | 1300 | 3050 |
|  | MFR | (g/10 min) | 26.3 | 12.6 | 2.52 | 2.87 |
|  | $[\eta]$ |  | 0.91 | 1.06 | 1.67 | 1.59 |
|  | D |  | 949 | 942 | 934 | 935 |
|  | B.D | g/ml | 0.31 | 0.323 | 0.36 | 0.345 |
|  | GPC | Mw | 59300 | 61000 | 114700 | 85600 |
|  |  | Mn | 6300 | 5500 | 18400 | 18000 |
|  |  | Mw/Mn | 9.4 | 11.1 | 6.2 | 4.8 |
|  | GPC-$[\eta]$ | Mw | 79300 | 89000 | 113273 | 189000 |
|  |  | Mn | 4074 | 7620 | 8748 | 21100 |
|  |  | Mw/Mn | 19.5 | 11.7 | 12.9 | 9.0 |
|  | Log$[\eta]$ |  | −0.040958608 | 0.025305865 | 0.222716471 | 0.201397124 |
|  | MT | g | 1.8 | 1.94 | 4.81 | 7.01 |
|  | $\eta^*$ |  | 6288.9 | 14340 | 40321 | 32739 |
|  | $\eta 0$ |  | 11057 | 44290 | 204947 | 215895 |
|  | MT/$\eta^*$ |  | 0.000286 | 0.000135 | 0.000119 | 0.000214 |
|  | Log$M_{GPC-[\eta]}$ |  | 4.8993 | 4.9494 | 5.3032 | 5.2765 |
| GPC peak analysis | Fraction ratio | Cmpnt. A | 67.3 | 70.7 | 70.9 | 78.4 |
|  |  | Cmpnt. B | 26.9 | 17.4 | 15.5 | 14.7 |
|  |  | 3rd cmpnt. | 5.8 | 11.9 | 13.6 | 6.9 |
|  | Log$M_{max}$ |  | 3.98 | 3.98 | 4.42 | 4.42 |
|  | $H_{max}$ |  | 0.016 | 0.015 | 0.019 | 0.021 |
|  | Log$M_{second}$ |  | 4.70 | 4.68 | 5.56 | 5.52 |
|  | $H_{second}$ |  | 0.0062 | 0.0068 | 0.0041 | 0.0031 |
|  | $H_{max}/H_{second}$ |  | 2.7 | 2.2 | 4.7 | 6.8 |

TABLE 10

|  |  |  | Example | |
|---|---|---|---|---|
|  |  |  | M-33 | M-34 |
| Solid catalyst component | No. |  | Y-20 | Y-20 |
|  | Metallocene compound | Cmpnt. A | A2 | A2 |
|  |  | Cmpnt. B | B1 | B1 |
|  | Cmpnt. (A)/Cmpnt (B) | Molar ratio | 47/53 | 47/53 |
| Prepolymerized catalyst component | No. |  | YP-20 | YP-20 |
| Polymerization conditions | Catalyst amount | mol/h | 0.023 | 0.023 |
|  | Ethylene | kg/h | 5.5 | 5.5 |
|  | 1-Butene | g/h | 450 | 500 |
|  | Polymerization temperature | ° C. | 80 | 80 |
|  | Polymerization pressure | MPa · G | 2.0 | 2.0 |
|  | Ethylene partial pressure | MPa · A | 1.2 | 1.2 |
|  | Retention time | hr | 10.1 | 9.5 |
|  | Gas phase: hydrogen/ethylene ratio | m.r. ($\times 10^{-4}$) | 8.45 | 15.7 |
|  | Gas phase: 1-butene/ethylene ratio | m.r. | 0.0314 | 0.0334 |
|  | Polymer yield | kg/h | 2.4 | 2.5 |

TABLE 11

|  |  |  | Example | | | | | |
|---|---|---|---|---|---|---|---|---|
|  |  |  | M-35 | M-36 | M-37 | M-38 | M-39 | M-40 |
| Solid catalyst component | No. |  | Y-23 | Y-20 | Y-20 | Y-21 | Y-21 | Y-21 |
|  | Metallocene compound | Cmpnt. A | A3 | A2 | A2 | A2 | A2 | A2 |
|  |  | Cmpnt. B | B1 | B1 | B1 | B1 | B1 | B1 |
|  | Cmpnt. (A)/Cmpnt (B) | Molar ratio | 45/55 | 47/53 | 47/53 | 42/58 | 42/58 | 42/58 |
| Prepolymerized catalyst component | No. |  | YP-23 | YP-20 | YP-20 | YP-21 | YP-21 | YP-21 |
| Polymerization conditions | Catalyst amount | mol/h | 0.038 | 0.018 | 0.018 | 0.014 | 0.019 | 0.019 |
|  | Ethylene | kg/h | 6.3 | 5.7 | 6.0 | 5.1 | 5.6 | 5.5 |
|  | 1-Hexene | g/h | 500 | 350 | 400 | 240 | 560 | 520 |
|  | Polymerization temperature | ° C. | 80 | 80 | 80 | 80 | 70 | 70 |
|  | Polymerization pressure | MPa · G | 2.0 | 2.0 | 2.0 | 2.0 | 2.0 | 2.0 |
|  | Ethylene partial pressure | MPa · A | 1.2 | 1.2 | 1.2 | 1.2 | 1.2 | 1.2 |
|  | Retention time | hr | 6.9 | 9.6 | 9.6 | 11.4 | 9.7 | 10.6 |

TABLE 11-continued

|  |  | Example |  |  |  |  |  |
|---|---|---|---|---|---|---|---|
|  |  | M-35 | M-36 | M-37 | M-38 | M-39 | M-40 |
| Gas phase: hydrogen/ethylene ratio | m.r. ($\times 10^{-4}$) | 12 | 9.1 | 9.6 | 11.3 | 7.0 | 6.3 |
| Gas phase: 1-hexene/ethylene ratio | m.r. | 0.0080 | 0.0077 | 0.0074 | 0.0076 | 0.0100 | 0.0100 |
| Polymer yield | kg/h | 3.5 | 2.5 | 2.5 | 2.1 | 2.5 | 2.3 |

TABLE 12

|  |  |  | Example |  |  |  |  |  |
|---|---|---|---|---|---|---|---|---|
|  |  |  | M-41 | M-42 | M-43 | M-44 | M-45 | M-46 |
| Solid catalyst component | No. |  | Y-23 | Y-24 | Y-24 | Y-22 | Y-22 | Y-25 |
|  | Metallocene compound | Cmpnt. A | A3 | A3 | A3 | A2 | A2 | A2 |
|  |  | Cmpnt. B | B1 | B1 | B1 | B1 | B1 | B1 |
|  | Cmpnt. (A)/Cmpnt (B) | Molar ratio | 45/55 | 40/60 | 40/60 | 39/61 | 39/61 | 24/76 |
| Prepolymerized catalyst component | No. |  | YP-23 | YP-24 | YP-24 | YP-22 | YP-22 | YP-25 |
| Polymerization conditions | Catalyst amount | mol/h | 0.045 | 0.031 | 0.027 | 0.025 | 0.023 | 0.039 |
|  | Ethylene | kg/h | 6.6 | 5.7 | 5.7 | 5.7 | 5.7 | 7 |
|  | 1-Hexene | g/h | 500 | 0.41 | 0.41 | 0.41 | 0.38 | 0.64 |
|  | Polymerization temperature | °C. | 80 | 80 | 80 | 80 | 80 | 80 |
|  | Polymerization pressure | MPa·G | 2.0 | 2.0 | 2.0 | 2.0 | 2.0 | 2.0 |
|  | Ethylene partial pressure | MPa·A | 1.2 | 1.2 | 1.2 | 1.2 | 1.2 | 1.2 |
|  | Retention time | hr | 6.0 | 6.5 | 6.9 | 6.9 | 7.0 | 4.5 |
|  | Gas phase: hydrogen/ethylene ratio | m.r. ($\times 10^{-4}$) | 13.2 | 12.4 | 16.1 | 12.2 | 16.3 | 15.5 |
|  | Gas phase: 1-hexene/ethylene ratio | m.r. | 0.0073 | 0.0082 | 0.0079 | 0.0081 | 0.0080 | 0.0077 |
| Polymer yield |  | kg/h | 4.0 | 3.7 | 3.5 | 3.5 | 3.4 | 5.3 |

TABLE 13

|  |  | Example |  |  |  |  |  |  |
|---|---|---|---|---|---|---|---|---|
|  |  | M-33 | M-34 | M-3 | M-6 | M-11 | M-12 | M-13 |
| Comonomer |  | 1-butene | 1-butene | 1-butene | 1-butene | 1-butene | 1-butene | 1-butene |
| MFR | g/10 min | 11.5 | 22.3 | 25.7 | 24.5 | 10.3 | 20.6 | 9.0 |
| D | kg/m$^3$ | 919 | 920 | 921 | 921 | 921 | 903 | 902 |
| [η] | dl/g | 1.32 | 1.11 | 1.05 | 1.04 | 1.27 | 1.01 | 1.15 |
| MT | g | 2.86 | 2.05 | 2.60 | 2.14 | 1.59 | 1.35 | 3.22 |
| η* | P | 11449 | 5800 | 5244 | 4131 | 8837 | 3953 | 10726 |
| MT/η* × 10$^4$ | g/P | 2.50 | 3.54 | 4.96 | 5.17 | 1.80 | 3.41 | 3.00 |
| $M_{Me+Et}/M_{all}$ | — | 1.00 | 1.00 | 1.00 | 1.00 | 1.00 | 1.00 | 1.00 |
| η0 | P | 28462 | 10384 | 7657 | 6896 | 14293 | 6558 | 24168 |
| GPC | Mn | 19500 | 16400 | 14800 | 16000 | 20810 | 19000 | 19800 |
|  | Mw | 187000 | 144440 | 113400 | 105000 | 106500 | 87300 | 99860 |
|  | Mz | 1980000 | 1820000 | 1190000 | 1100000 | 918000 | 693000 | 580000 |
|  | Mw/Mn | 9.59 | 8.81 | 7.66 | 6.56 | 5.12 | 4.59 | 5.04 |
|  | Mz/Mw | 10.59 | 12.60 | 10.49 | 10.48 | 8.62 | 7.94 | 5.81 |
| *1 |  | 378000 | 157100 | 69000 | 53100 | 55700 | 28400 | 44800 |
| *2 |  | 840 | 350 | 150 | 120 | 120 | 60 | 100 |
| Peak top M |  | $1.0 \times 10^{4.38}$ | $1.0 \times 10^{4.34}$ | $1.0 \times 10^{4.26}$ | $1.0 \times 10^{4.32}$ | $1.0 \times 10^{4.34}$ | $1.0 \times 10^{4.30}$ | $1.0 \times 10^{4.32}$ |

*1: $4.5 \times 10^{-13} \times Mw^{3.4}$
*2: $0.01 \times 10^{-13} \times Mw^{3.4}$

TABLE 14

|  |  |  | Example | |
|---|---|---|---|---|
|  |  |  | M-33 | M-34 |
| Neck-in | Take-up speed 50 m/min | mm | 45 | 43 |
|  | Take-up speed 80 m/min | mm |  | 42 |
|  | Take-up speed 120 m/min | mm |  |  |
|  | Take-up speed 200 m/min | mm |  |  |
| Take-up surge |  | m/min | Did not occur | Did not occur |

TABLE 14-continued

|  |  |  | Example | |
|---|---|---|---|---|
|  |  |  | M-33 | M-34 |
| Take-up speed at break |  | m/min | 70 | 80 |
| Resin pressure |  | MPa | 8.3 | 5.1 |
| Heat seal strength | 100° C. | N/15 mm width |  |  |
|  | 110° C. | N/15 mm width |  | 0.3 |
|  | 120° C. | N/15 mm width |  | 2.7 |
|  | 130° C. | N/15 mm width |  | 30.3 |
|  | 140° C. | N/15 mm width |  | 31.7 |
|  | 150° C. | N/15 mm width |  | 32.5 |
|  | 160° C. | N/15 mm width |  | 33.2 |

TABLE 15

|  |  | Example | | | | | | |
|---|---|---|---|---|---|---|---|---|
|  |  | M-35 | M-36 | M-37 | M-38 | M-39 | M-40 | M-41 |
| Comonomer |  | 1-hexene | 1-hexene | 1-hexene | 1-hexene | 1-hexene | 1-hexene | 1-hexene |
| MFR | g/10 min | 24.1 | 10.2 | 23.0 | 11.2 | 17.7 | 19.7 | 19.5 |
| D | kg/m³ | 919 | 919 | 918 | 920 | 908 | 904 | 920 |
| [η] | dl/g | 1.06 | 1.26 | 1.09 | 1.24 | 1.08 | 1.05 | 1.09 |
| MT | g | 1.30 | 3.11 | 1.64 | 2.78 | 1.61 | 1.41 | 2.28 |
| η* | P | 4100 | 9500 | 4100 | 9300 | 5000 | 4500 | 6500 |
| MT/η* × 10⁴ | g/P | 3.18 | 3.26 | 3.97 | 2.98 | 3.25 | 3.14 | 3.52 |
| Total of Me branches and Et branches (A + B) | branches/1000 C. | 0.5 | 0.4 | 0.5 | 0.4 | 0.5 | 0.5 | 0.5 |
| η0 | P | 6370 | 19900 | 6300 | 20500 | 7630 | 6560 | 11600 |
| GPC Mn |  | 19800 | 19700 | 18300 | 18400 | 19300 | 18900 | 18000 |
| Mw |  | 118000 | 146000 | 117000 | 148000 | 100000 | 94100 | 120000 |
| Mz |  | 1230000 | 1190000 | 1120000 | 1330000 | 79100 | 596000 | 1405000 |
| Mw/Mn |  | 5.98 | 7.41 | 6.38 | 8.08 | 5.19 | 4.98 | 6.67 |
| Mz/Mw |  | 10.42 | 8.11 | 9.61 | 8.98 | 7.88 | 6.33 | 11.71 |
| *2 |  | 79000 | 162900 | 76700 | 170600 | 45000 | 36600 | 83600 |
| *3 |  | 180 | 360 | 170 | 380 | 100 | 80 | 190 |
| Peak top M |  | $1.0 \times 10^{4.36}$ | $1.0 \times 10^{4.38}$ | $1.0 \times 10^{4.34}$ | $1.0 \times 10^{4.38}$ | $1.0 \times 10^{4.34}$ | $1.0 \times 10^{4.34}$ | $1.0 \times 10^{4.38}$ |

*1: below detection lower limit (0.02/1000 C.)
*2: $4.5 \times 10^{-13} \times Mw^{3.4}$
*3: $0.01 \times 10^{-13} \times Mw^{3.4}$

TABLE 16

|  |  | Example | | | | | | |
|---|---|---|---|---|---|---|---|---|
|  |  | M-42 | M-43 | M-44 | M-45 | M-46 | M-4 | M-5 |
| Comonomer |  | 1-hexene | 1-hexene | 1-hexene | 1-hexene | 1-hexene | 1-hexene | 1-hexene |
| MFR | g/10 min | 4.3 | 8.9 | 5.7 | 8.4 | 2.3 | 13.3 | 17.7 |
| D | kg/m³ | 920 | 918 | 917 | 919 | 917 | 935 | 936 |
| [η] | dl/g | 1.38 | 1.18 | 1.28 | 1.21 | 1.46 | 1.28 | 1.16 |
| MT | g | 7.61 | 6.18 | 7.49 | 6.26 | 9.30 | 2.41 | 2.10 |
| η* | P | 27000 | 13000 | 19000 | 12000 | 43000 | 9500 | 6800 |
| MT/η* × 10⁴ | g/P | 2.86 | 4.59 | 3.88 | 5.21 | 2.15 | 2.55 | 3.09 |
| Total of Me branches and Et branches (A + B) | branches/1000 C. | 0.3 | 0.5 | 0.4 | 0.5 | 0.5 | 0.3 | 0.4 |
| η0 | P | 98600 | 34600 | 62500 | 32000 | 294000 | 24400 | 16600 |
| GPC Mn |  | 21600 | 19400 | 20200 | 18875 | 20260 | 18100 | 16100 |
| Mw |  | 163000 | 133000 | 150000 | 144199 | 181919 | 149000 | 112500 |
| Mz |  | 1230000 | 963000 | 1130000 | 1239340 | 1323547 | 1530000 | 1070000 |
| Mw/Mn |  | 7.52 | 6.88 | 7.43 | 7.64 | 8.98 | 8.23 | 6.99 |
| Mz/Mw |  | 7.55 | 7.22 | 7.43 | 8.59 | 7.28 | 10.27 | 9.51 |
| *2 |  | 236900 | 118700 | 178600 | 156200 | 344200 | 174600 | 67200 |
| *3 |  | 530 | 260 | 400 | 350 | 760 | 390 | 150 |
| Peak top M |  | $1.0 \times 10^{4.38}$ | $1.0 \times 10^{4.36}$ | $1.0 \times 10^{4.36}$ | $1.0 \times 10^{4.36}$ | $1.0 \times 10^{4.36}$ | $1.0 \times 10^{4.36}$ | $1.0 \times 10^{4.30}$ |

*1: below detection lower limit (0.02/1000 C.)
*2: $4.5 \times 10^{-13} \times Mw^{3.4}$
*3: $0.01 \times 10^{-13} \times Mw^{3.4}$

TABLE 17

| | | | Example | | | | | | | | |
|---|---|---|---|---|---|---|---|---|---|---|---|
| | | | M-35 | M-36 | M-37 | M-38 | M-39 | M-40 | M-41 | M-43 | M-45 |
| Neck-in | Take-up speed 50 m/min | mm | | 46 | | 49 | | | 46 | 47 | 50 |
| | Take-up speed 80 m/min | mm | 51 | | 49 | | 66 | 71 | 43 | | |
| | Take-up speed 120 m/min | mm | 47 | | 44 | | 62 | 66 | | | |
| | Take-up speed 200 m/min | mm | | | | | 58 | 62 | | | |
| Take-up surge | | m/min | Did not occur | Did not occur | Did not occur | Did not occur | Did not occur | Did not occur | Did not occur | Did not occur | Did not occur |
| Take-up speed at break | | m/min | 190 | 60 | 110 | 60 | 200 | 210 | 70 | 50 | 50 |
| Resin pressure | | MPa | 4.6 | 8.2 | 4.8 | 7.7 | 5.5 | 4.9 | 5.3 | | |
| Heat seal strength | 100° C. | N/15 mm width | | | | 0.2 | 26.7 | 39.1 | | | |
| | 110° C. | N/15 mm width | 0.5 | 1.0 | 0.9 | 3.6 | 45.7 | 46.9 | | | |
| | 120° C. | N/15 mm width | 31.0 | 34.3 | 35.0 | 39.0 | 50.4 | 51.4 | | | |
| | 130° C. | N/15 mm width | 49.4 | 43.8 | 49.8 | 52.7 | 52.7 | 53.2 | | | |
| | 140° C. | N/15 mm width | 47.8 | 44.7 | 49.1 | 57.1 | 55.3 | 55.3 | | | |
| | 150° C. | N/15 mm width | 47.0 | 46.3 | 50.4 | 58.0 | 56.0 | 55.7 | | | |
| | 160° C. | N/15 mm width | 47.7 | 46.7 | 51.3 | | | | | | |

*4: Unmeasurable because of heavy take-up surge.

TABLE 18

| | | Comp. Ex. M-5 | Comp. Ex. M-6 | Comp. Ex. M-7 | Comp. Ex. M-8 | Comp. Ex. M-9 | Comp. Ex. M-10 | Comp. Ex. M-11 | Comp. Ex. M-12 |
|---|---|---|---|---|---|---|---|---|---|
| Comonomer | | 4-methyl-1-pentene | 1-hexene | 1-octene | 1-hexene | 1-hexene | — | 1-hexene | 1-hexene |
| MFR | g/10 min | 8.7 | 13.3 | 1.7 | 32.0 | 23.0 | 7.1 | 7.1 | 11.5 |
| D | kg/m$^3$ | 918 | 913 | 899 | 941 | 918 | 918 | 931 | 920 |
| [η] | dl/g | 1.35 | 1.00 | 1.53 | 0.98 | 1.09 | 1.14 | 1.18 | 1.09 |
| MT | g | 0.23 | 1.00 | 1.96 | 1.00 | 1.64 | 3.60 | 1.60 | 2.52 |
| η* | P | 8280 | 7400 | 44700 | 2500 | 4100 | 13200 | 20800 | 11200 |
| MT/η* × 10$^4$ | g/P | 0.28 | 1.35 | 0.44 | 4.02 | 3.97 | 2.73 | 0.77 | 2.25 |
| $M_{Me+Et}/M_{all}$ | — | 0.00 | 0.00 | 0.00 | 0.16 | 0.03 | — | — | — |
| Total of Me branches and Et branches | branches/1000 C. | *3 | *3 | *3 | 0.7 | — | 9.4 | *1 | 0.4 |
| η0 | P | 8620 | 10700 | 68200 | 3240 | 6300 | 19600 | 46000 | 24300 |
| GPC Mn | | 19000 | 7600 | 28700 | 13200 | 18300 | 16000 | 9000 | 11300 |
| Mw | | 64000 | 64000 | 85300 | 117000 | 117000 | 470000 | 91500 | 141000 |
| Mz | | 146000 | 280000 | 164000 | 1190000 | 1120000 | 3700000 | 652000 | 1250000 |
| Mw/Mn | | 3.37 | 8.42 | 2.97 | 8.87 | 6.38 | 29.38 | 10.17 | 12.48 |
| Mz/Mw | | 2.28 | 4.38 | 1.92 | 10.18 | 9.61 | 7.87 | 7.13 | 8.87 |
| *1 | | 9900 | 9900 | 26200 | 76700 | 76700 | 8676500 | 33300 | 144700 |
| *2 | | 20 | 20 | 60 | 170 | 170 | 19300 | 70 | 320 |
| Peak top M | | 1.0 × 10$^{4.50}$ | 1.0 × 10$^{4.38}$ | 1.0 × 10$^{4.74}$ | 1.0 × 10$^{4.26}$ | 1.0 × 10$^{4.34}$ | 1.0 × 10$^{4.36}$ | 1.0 × 10$^{4.36}$ | 1.0 × 10$^{4.14}$ |

*1: $4.5 \times 10^{-13} \times Mw^{3.4}$
*2: $0.01 \times 10^{-13} \times Mw^{3.4}$
*3: below detection lower limit (0.02/1000 C.)

TABLE 19

| | | | Comp. Ex. M-5 | Comp. Ex. M-6 | Comp. Ex. M-8 | Comp. Ex. M-9 | Comp. Ex. M-10 | Comp. Ex. M-12 |
|---|---|---|---|---|---|---|---|---|
| Neck-in | Take-up speed 50 m/min | mm | | | | | | |
| | Take-up speed 80 m/min | mm | 185 | 106 | 68 | 49 | 40 | 54 |
| | Take-up speed 120 m/min | mm | *4 | *4 | 59 | 44 | | |
| | Take-up speed 200 m/min | mm | *4 | *4 | 53 | | | |

TABLE 19-continued

|  |  | Comp. Ex. M-5 | Comp. Ex. M-6 | Comp. Ex. M-8 | Comp. Ex. M-9 | Comp. Ex. M-10 | Comp. Ex. M-12 |
|---|---|---|---|---|---|---|---|
| Take-up surge | m/min | 30 | 50 | Did not occur | Did not occur | Did not occur | Did not occur |
| Take-up speed at break | m/min | >350 | 240 | 210 | 110 | 110 | 100 |
| Resin pressure | MPa | 10.8 | 5.1 | 2.0 | 4.8 | 5.9 | 3.4 |
| Heat seal strength 100° C. | N/15 mm width |  |  |  |  |  |  |
| 110° C. | N/15 mm width |  |  |  | 0.9 |  |  |
| 120° C. | N/15 mm width | 20.8 | 36.8 | 0.9 | 35.0 | 30.8 | 43.5 |
| 130° C. | N/15 mm width | 47.5 | 46.2 | 11.1 | 49.8 | 32.8 | 44.8 |
| 140° C. | N/15 mm width | 48.9 | 48.8 | 29.5 | 49.1 | 34.7 | 44.1 |
| 150° C. | N/15 mm width | 49.5 | 49.7 | 38.0 | 50.4 | 33.6 | 44.6 |
| 160° C. | N/15 mm width | 50.5 | 49.9 | 40.8 | 51.3 | 34.8 | 43.8 |

*4: Unmeasurable because of heavy take-up surge.

INDUSTRIAL APPLICABILITY

The olefin polymerization catalysts (b) containing the bridged metallocene compound of Formula [1] and the bridged metallocene compound of Formula [14] can catalyze olefin polymerization to afford ethylene polymers having excellent processability and a large number of long-chain branches. According to the polymerization processes using the catalysts, such ethylene polymers are produced efficiently.

The ethylene polymers according to the present invention have sufficiently high melt tension compared to conventional ethylene polymers produced with Ziegler-Natta catalysts or metallocene catalysts, and can give shaped articles excellent in mechanical strength. The ethylene polymers of the invention are suitably used to manufacture plastic shaped articles having sufficient mechanical strength and uniform quality. The ethylene polymers of the invention have appropriate heat seal strength and are suitably used to produce plastic shaped articles having easy-opening properties and uniform quality.

The invention claimed is:

1. A process for producing olefin polymers, comprising polymerizing one or more monomers selected from ethylene and C3-20 olefins and at least one of the monomers is ethylene or propylene, in the presence of an olefin polymerization catalyst (b) comprising the following components (A), (B) and (C):

Component (A): a bridged metallocene compound of Formula (1) described below;

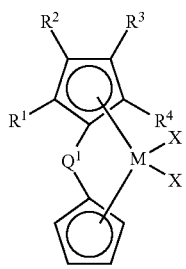

[1]

wherein $R^1$, $R^2$, $R^3$ and $R^4$ are selected from a hydrogen atom, hydrocarbon groups, and halogen-containing hydrocarbon groups and are the same or different from one another; and at least one of these groups is an ethyl group or a group represented by Formula [6] below; neighboring substituent groups among $R^1$ to $R^4$ may be linked together to form an aliphatic ring; $Q^1$ is selected from C1-20 hydrocarbon groups, halogen-containing groups, silicon-containing groups, germanium-containing groups and tin-containing groups; X independently at each occurrence is a group selected from a hydrogen atom, halogen atoms, hydrocarbon groups, halogen-containing groups, silicon-containing groups, oxygen-containing groups, sulfur-containing groups, nitrogen-containing groups and phosphorus-containing groups; and M is a titanium atom, a zirconium atom or a hafnium atom;

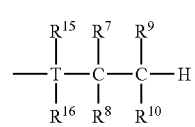

[6]

wherein $R^7$ to $R^{16}$ are selected from a hydrogen atom, hydrocarbon groups, and halogen-containing hydrocarbon groups and are the same or different from one another, but they are not aryl groups; and T represents a carbon atom;

Component (B): a bridged metallocene compound represented by Formula [14] below;

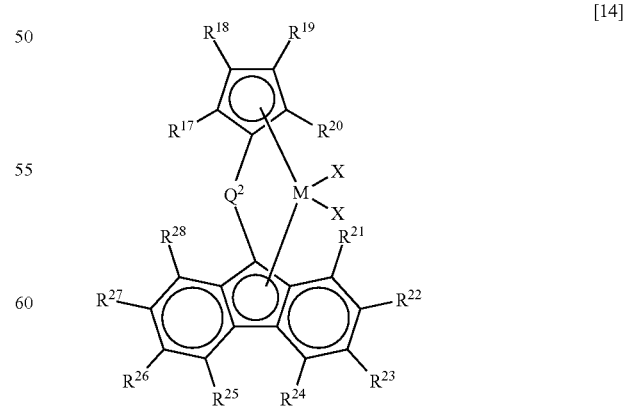

[14]

wherein $R^{17}$ to $R^{20}$, and $R^{21}$ to $R^{28}$ are selected from a hydrogen atom, hydrocarbon groups, halogen-containing groups, oxygen-containing groups, nitrogen-containing groups, boron-containing groups, sulfur-containing groups, phosphorus-containing groups, silicon-containing groups, germanium-containing groups and tin-containing groups and are the same or different from one another; neighboring substituent groups among these groups may be linked together to form a ring; $Q^2$ is selected from C1-20 hydrocarbon groups, halogen-containing groups, silicon-containing groups, germanium-containing groups and tin-containing groups; M is selected from a titanium atom, a zirconium atom and a hafnium atom; and X independently at each occurrence is a group selected from a hydrogen atom, halogen atoms, hydrocarbon groups, halogen-containing groups, silicon-containing groups, oxygen-containing groups, sulfur-containing groups, nitrogen-containing groups and phosphorus-containing groups;

Component (C): at least one compound selected from the group consisting of:
(c-1) organometallic compounds represented by Formulae [18], [19] and [20] below;
(c-2) organoaluminum oxy-compounds; and
(c-4) compounds that react with components (A) and (B) to form an ion pair;

  [18]

wherein $R^a$ and $R^b$ are each a C1-15 hydrocarbon group and are the same or different from each other; X is a halogen atom; $0 \leq m \leq 3$, $0 \leq n < 3$, $0 \leq p < 3$, $0 \leq q < 3$ and $m+n+p+q=3$;

  [19]

wherein $M^a$ is Li, Na or K; and $R^a$ is a C1-15 hydrocarbon group;

  [20]

wherein $R^a$ and $R^b$ are each a C1-15 hydrocarbon group and are the same or different from each other; $M^b$ is selected from Mg, Zn and Cd; X is a halogen atom; $0 < r \leq 2$, $0 \leq s < 1$, $0 \leq t \leq 1$ and $r+s+t=2$, wherein the olefin polymers satisfy the following requirements [3] and [6]

[3] the ratio [MT/η*(g/P)] is in the range of $2.50 \times 10^{-4}$ to $9.00 \times 10^{-4}$ wherein [MT (g)] is the melt tension at 190° C. and [η*(P)] is the shear viscosity at 200° C. and an angular velocity of 1.0 rad/sec;

[6] a molecular weight distribution curve obtained by GPC shows a molecular weight at a maximum weight fraction (peak top M) in the range of $1.0 \times 10^{4.30}$ to $1.0 \times 10^{4.50}$.

2. The process for producing olefin polymers according to claim 1, wherein the olefin polymerization catalyst (b) comprises a solid catalyst component (K1) comprising a solid carrier (S), component (C) and component (A), and a solid catalyst component (K2) comprising a solid carrier (S), component (C) and component (B).

3. The process for producing olefin polymers according to claim 1, wherein the olefin polymerization catalyst (b) comprises a solid catalyst component (K3) comprising a solid carrier (S), component (A), component (B) and the component (C).

4. The process for producing olefin polymers according to claim 1, wherein in Formula [1], at least one of $R^1$, $R^2$, $R^3$ and $R^4$ is a hydrocarbon group.

5. The process for producing olefin polymers according to claim 1, wherein the component (C) is an organoaluminum oxy-compound (c-2).

6. The process for producing olefin polymers according to claim 2, wherein the solid carrier (S) is a porous oxide.

7. The process for producing olefin polymers according to claim 1, wherein the olefin polymers are ethylene polymers, comprising homopolymerising ethylene or copolymerizing ethylene and C3-20 olefins.

8. The process for producing olefin polymers according to claim 7, wherein the olefin polymerization catalyst (b) comprises a solid catalyst component (K1) comprising a solid carrier (S), component (C) and component (A), and a solid catalyst component (K2) comprising a solid carrier (S), component (C) and component (B).

9. The process for producing olefin polymers according to claim 7, wherein the olefin polymerization catalyst (b) comprises a solid catalyst component (K3) comprising a solid carrier (S), component (A), component (B) and component (C).

10. The process for producing olefin polymers according to claim 7, wherein in Formula [1], at least one of $R^1$, $R^2$, $R^3$ and $R^4$ is a hydrocarbon group.

11. The process for producing olefin polymers according to claim 7, wherein component (C) is an organoaluminum oxy-compound (c-2).

12. The process for producing olefin polymers according to claim 7, wherein the solid carrier (S) is a porous oxide.

* * * * *